(12) United States Patent
Szesko et al.

(10) Patent No.: US 8,262,842 B2
(45) Date of Patent: Sep. 11, 2012

(54) AUTOMATED LABEL VERIFY SYSTEMS AND METHODS FOR DISPENSING PHARMACEUTICALS

(75) Inventors: Michael J. Szesko, Freehold, NJ (US);
Bradley Carson, Maumee, OH (US);
Kevin R. Fearon, Fairlawn, OH (US);
Robert A. Smith, Stevenson, MD (US);
Thomas P. Bonkenburg, York, PA (US);
Jonathan M. Herring, Cambridge (CA)

(73) Assignee: Omnicare, Inc., Cincinnati, OH (US)

( * ) Notice: Subject to any disclaimer, the term of this patent is extended or adjusted under 35 U.S.C. 154(b) by 965 days.

(21) Appl. No.: 12/234,985

(22) Filed: Sep. 22, 2008

(65) Prior Publication Data

US 2009/0179072 A1 Jul. 16, 2009

Related U.S. Application Data

(60) Provisional application No. 60/974,181, filed on Sep. 21, 2007, provisional application No. 61/076,905, filed on Jun. 30, 2008.

(51) Int. Cl.
| | |
|---|---|
| *B29C 65/56* | (2006.01) |
| *B29C 65/72* | (2006.01) |
| *B29C 65/78* | (2006.01) |
| *B32B 38/14* | (2006.01) |
| *B32B 38/18* | (2006.01) |
| *B32B 41/02* | (2006.01) |
| *B65C 9/02* | (2006.01) |
| *B65C 9/06* | (2006.01) |
| *B65C 9/26* | (2006.01) |
| *B65C 9/40* | (2006.01) |
| *B65C 9/46* | (2006.01) |
| *B32B 37/10* | (2006.01) |
| *B32B 38/04* | (2006.01) |
| *B32B 38/06* | (2006.01) |

(52) U.S. Cl. ......... 156/297; 156/277; 156/378; 156/379
(58) Field of Classification Search .................. 156/378, 156/379, 277, 297
See application file for complete search history.

(56) References Cited

U.S. PATENT DOCUMENTS

| | | |
|---|---|---|
| 3,606,014 A | 9/1971 | Linn |
| 3,656,616 A | 4/1972 | Wallington |
| 3,882,316 A | 5/1975 | Garris et al. |

(Continued)

FOREIGN PATENT DOCUMENTS

CA 2509120 A1 2/2006

(Continued)

OTHER PUBLICATIONS

European Patent Office, International Search Report issued in corresponding PCT Application serial No. PCT/US2008/077184 dated Jan. 9, 2009.

(Continued)

*Primary Examiner* — Sonya Mazumdar
(74) *Attorney, Agent, or Firm* — Wood, Herron & Evans, LLP

(57) ABSTRACT

Apparatus and methods for filling a prescription order with plurality of products each containing a pharmaceutical. The apparatus and method verifying a barcode on each of the products and printing and applying a patient label with a verified barcode to each of the products. After the patient label is applied, the barcodes are independently verified before the products are released.

25 Claims, 39 Drawing Sheets

U.S. PATENT DOCUMENTS

| | | | |
|---|---|---|---|
| 4,011,155 A | | 3/1977 | Feurstein et al. |
| 4,053,056 A | | 10/1977 | Day |
| 4,351,679 A | * | 9/1982 | Dreher ..................... 156/70 |
| 4,530,199 A | | 7/1985 | Manservisi et al. |
| 5,101,609 A | | 4/1992 | Cook |
| 5,406,770 A | | 4/1995 | Fikacek |
| 5,414,974 A | * | 5/1995 | Van de Ven et al. ............ 53/399 |
| 5,568,715 A | | 10/1996 | Ebel et al. |
| 5,593,267 A | | 1/1997 | McDonald et al. |
| 5,660,305 A | | 8/1997 | Lasher et al. |
| 5,720,154 A | | 2/1998 | Lasher et al. |
| 5,771,657 A | * | 6/1998 | Lasher et al. ..................... 53/55 |
| 5,880,443 A | | 3/1999 | McDonald et al. |
| 5,883,370 A | | 3/1999 | Walker et al. |
| 5,963,453 A | | 10/1999 | East |
| 6,158,193 A | | 12/2000 | Focke et al. |
| 6,179,030 B1 | * | 1/2001 | Rietheimer .................. 156/360 |
| 6,317,648 B1 | * | 11/2001 | Sleep et al. .................. 700/216 |
| 6,373,520 B1 | | 4/2002 | Cadieux, Jr. et al. |
| 6,522,945 B2 | * | 2/2003 | Sleep et al. .................. 700/225 |
| 6,575,216 B2 | * | 6/2003 | Yang ............................. 156/351 |
| 6,655,015 B2 | | 12/2003 | Kraenzle |
| 6,892,512 B2 | | 5/2005 | Rice et al. |
| 6,970,769 B2 | | 11/2005 | Rice et al. |
| 6,971,213 B2 | | 12/2005 | Battisti |
| 6,983,579 B2 | | 1/2006 | Rice et al. |
| 7,006,893 B2 | | 2/2006 | Hart et al. |
| 7,010,899 B2 | | 3/2006 | McErlean et al. |
| 7,047,706 B2 | | 5/2006 | Kraenzle |
| 7,185,477 B2 | | 3/2007 | Rice et al. |
| 7,386,965 B2 | | 6/2008 | McErlean et al. |
| RE40,453 E | | 8/2008 | Lasher et al. |
| 7,409,977 B2 | | 8/2008 | Rice et al. |
| 7,412,814 B2 | | 8/2008 | Rice et al. |
| RE40,510 E | | 9/2008 | Lasher et al. |
| 7,427,002 B2 | | 9/2008 | Liff et al. |
| 7,430,838 B2 | | 10/2008 | Rice et al. |
| 2002/0026768 A1 | * | 3/2002 | Duncan et al. ..................... 53/52 |
| 2002/0117405 A1 | * | 8/2002 | Wang et al. ..................... 206/5.1 |
| 2003/0176492 A1 | * | 9/2003 | Takeuchi et al. .............. 514/451 |
| 2003/0176942 A1 | | 9/2003 | Sleep et al. |
| 2004/0040975 A1 | | 3/2004 | Hunter et al. |
| 2004/0123564 A1 | * | 7/2004 | McErlean et al. .............. 53/411 |
| 2004/0123567 A1 | * | 7/2004 | McErlean et al. .............. 53/445 |
| 2004/0215486 A1 | | 10/2004 | Braverman |
| 2006/0161294 A1 | | 7/2006 | DiMaggio |
| 2006/0161298 A1 | | 7/2006 | DiMaggio |
| 2006/0185322 A1 | | 8/2006 | Kraenzle |
| 2006/0191239 A1 | | 8/2006 | Moodley |
| 2006/0277269 A1 | * | 12/2006 | Dent et al. ..................... 709/217 |
| 2007/0084150 A1 | | 4/2007 | Siegel et al. |
| 2007/0093935 A1 | * | 4/2007 | Fu ................................. 700/237 |
| 2007/0102109 A1 | | 5/2007 | Katritzky et al. |
| 2007/0125442 A1 | | 6/2007 | Tribble et al. |
| 2009/0048712 A1 | | 2/2009 | Rosenblum |
| 2009/0173779 A1 | * | 7/2009 | Szesko et al. ................. 235/375 |
| 2009/0179072 A1 | | 7/2009 | Szesko et al. |

FOREIGN PATENT DOCUMENTS

| | | |
|---|---|---|
| EP | 1388336 A1 | 11/2004 |
| EP | 1889802 A2 | 2/2008 |

OTHER PUBLICATIONS

USPTO, Office Action issued in related U.S. Appl. No. 12/235,173 dated Jan. 28, 2011.

European Patent Office, International Search Report issued in corresponding PCT Application serial No. PCT/US2008/077200 dated Jan. 29, 2009.

USPTO, Office Action issued in related U.S. Appl. No. 12/640,065 dated Mar. 12, 2012.

USPTO, Office Action issued in related U.S. Appl. No. 12/640,065 dated Nov. 16, 2011.

USPTO, Office Action issued in related U.S. Appl. No. 12/235,173 dated Jan. 4, 2012.

USPTO, Search Report and Written Opinion issued in related international application No. PCT/US10/60968 dated Apr. 19, 2011.

USPTO, Office Action issued in related U.S. Appl. No. 12/235,173 dated Jul. 7, 2011.

U.S. Patent and Trademark Office, Notice of Allowance issued in corresponding U.S. Appl. No. 12/640,065 mailed May 16, 2012, 8 pages.

U.S. Patent and Trademark Office, Notice of Allowance issued in corresponding U.S. Appl. No. 12/235,173 mailed May 15, 2012, 7 pages.

* cited by examiner

AUTOMATED LABEL VERIFY SYSTEMS AND METHODS FOR DISPENSING PHARMACEUTICALS

CROSS-REFERENCE TO RELATED APPLICATIONS

The present application claims the benefit of U.S. Provisional Patent Application Ser. No. 60/974,181, filed Sep. 21, 2007, and U.S. Provisional Patent Application Ser. No. 61/076,905, filed Jun. 30, 2008, the disclosures of which are hereby incorporated by reference herein in their entireties. The present application is also related to co-pending U.S. application Ser. No. 12/235,173, filed Sep. 22, 2008 and entitled "AUTOMATED LABEL VERIFY SYSTEMS AND METHODS FOR DISPENSING PHARMACEUTICALS," the disclosure of which is hereby incorporated by reference herein in its entirety.

BACKGROUND

This disclosure relates to systems and methods for dispensing pharmaceuticals and, in particular, to automated systems and dispensing methods for filling pharmaceutical orders.

Historically, pharmacies have filled large quantities of customer orders for skilled nursing facilities, assisted living facilities, independent living facilities, group homes, hospice facilities and other configurations of the nursing home industry and institutionalized long term care industry with a labor-intensive, pharmacist-based assembly line method. The customer orders are comprised of patient prescriptions, issued by a physician and fulfilled under close pharmacist supervision. The filling of prescriptions consists of executing the customer order by associating the correct pharmaceutical product with the correct prescription label. This is done by pharmacists, technicians, or combinations of these individuals. Products, in the form of a variety of packages (e.g., 7-day, 14-day, 15-day, 30-day dosages, and individually by form and strength), are removed from bulk inventory and, thereafter, a prescription label is printed and manually applied to the appropriate product.

This act of application may then be verified in one of many ways. It can be checked against a master order sheet (MAR), visually checked by the technician, pharmacist, or a combination of these individuals, or can be verified by manually scanning the information on the prescription label with that of the product label. Once each product is labeled, then the labeled products are grouped and presorted into containers. The presorted containers are broken down in a sortation area where the products are individually scanned and placed into the shipping containers (e.g., boxes, bags, bins, or totes). Typically at this point, the label application is re-verified and the product's association with the particular shipping container is checked. This is a barcode-scanning step where the package label, the prescription label, and the shipping tote (or a combination of any number of these items) are confirmed to be correct.

By the time a labeled and verified product is correctly placed in a shipping tote, it has typically been handled, or touched, by an individual approximately 1-13 times. The large number of touches required to process products represents inefficiencies and increases the potential for human error. Therefore, there remains significant room for improvement in the methodologies used by pharmacies to fill prescriptions against customer orders. What is needed are improved systems and methods for automatically labeling, verifying, and handling products that constitute the customer orders.

SUMMARY

An apparatus and method for filling a customer order with plurality of products each containing a pharmaceutical are described below. In one embodiment, each of the products is marked with a product barcode. The apparatus comprises a conveyor configured to move the products along a workflow path and a first verification station, a label application station, and a second verification station in the workflow path. The first verification station is configured to verify that the product barcode belongs in the prescription order being filled. The label application station is configured to print and apply a patient label onto each of the products. The second verification station is configured to independently verify that the product barcode on each of the products matches a patient barcode on the patient label (i.e., that the product barcode is associated with the proper patient barcode) after application to the product.

In another embodiment, the apparatus comprises a product loading station configured to receive batches of the products. The product loading station is also configured to singulate the products for subsequent processing along the workflow path. In this embodiment, the first verification station includes a bar code reader configured to read the product barcode on each of the products and a transfer arm configured to selectively remove the products from the workflow path. The label printing station includes a label printer configured to print the patient labels and an applicator configured to apply each patent label on one of the products. The second verification station includes a bar code reader configured to read the product barcode on each of the products and a patient barcode on each of the patient labels. The second verification station also includes a transfer arm configured to remove the products from the workflow path.

In yet a further embodiment, the product loading station, the first verification station, the labeling station, and the second verification station of the apparatus are configured to process products shaped with different form factors.

A method of filling a customer order with a plurality of the products, with the products loaded into a machine for processing, is also provided. The method comprises moving the products along a workflow path defined by a conveyor, automatically verifying a product barcode on each of the products at a first verification station in the workflow path of the conveyor, printing a patient label for each of the products verified by the first verification station, applying the patient labels to at least some of the products, and, thereafter, independently verifying that the product barcode matches a patient barcode on the patient label (i.e., that the product barcode is associated with the proper patient barcode) at a second verification station in the workflow path of the conveyor. In one specific embodiment, the method further comprises singulating batches of the products loaded into the machine so that the products can be individually processed by the machine, and automatically loading the individual products onto the conveyor.

DETAILED DESCRIPTION

Figure 3:
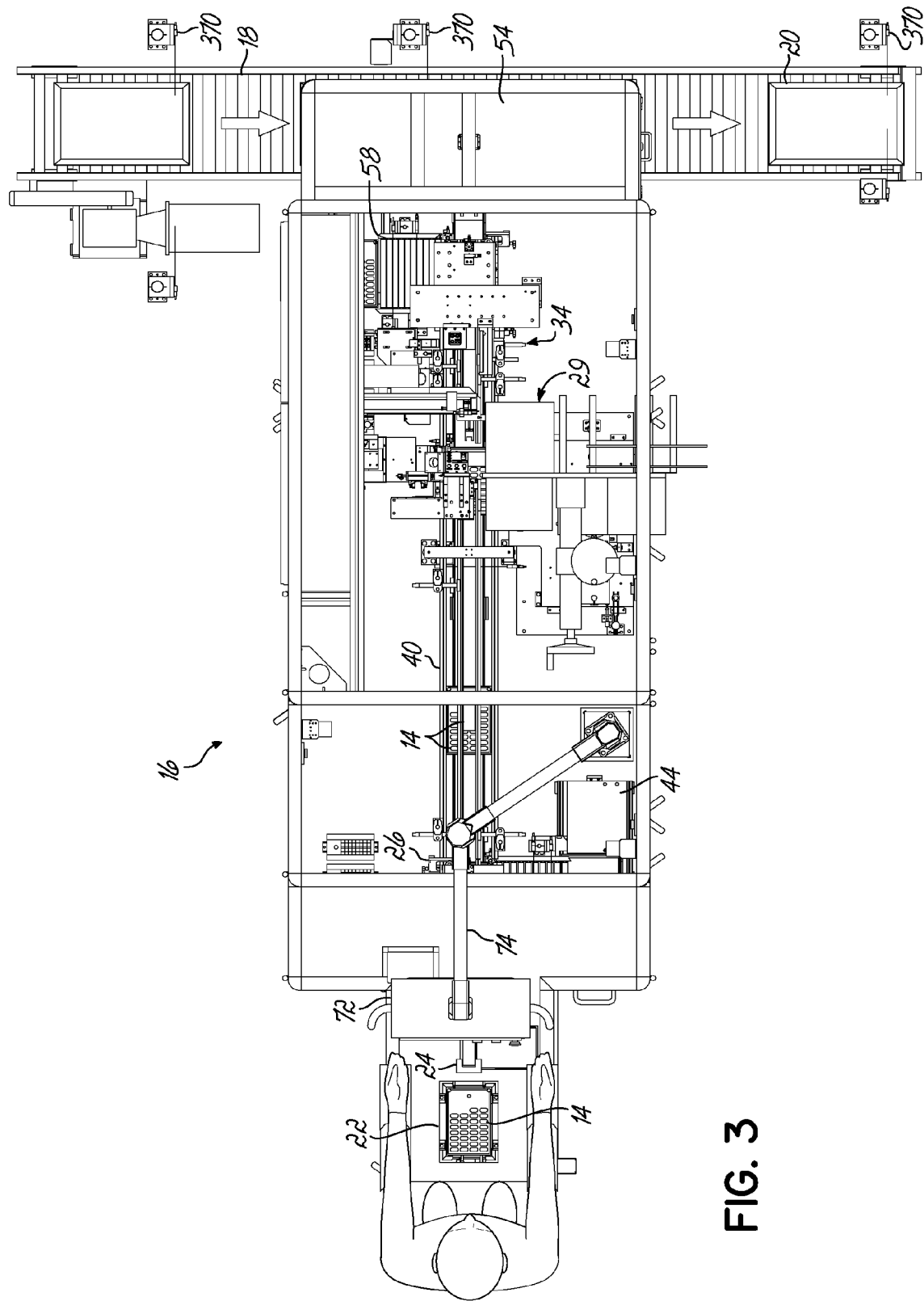
FIGS. 3, 4, and 5 are respective top plan, end elevation, and side elevation views of an ALV machine in the ALV system of FIG. 1.
Figure 4:
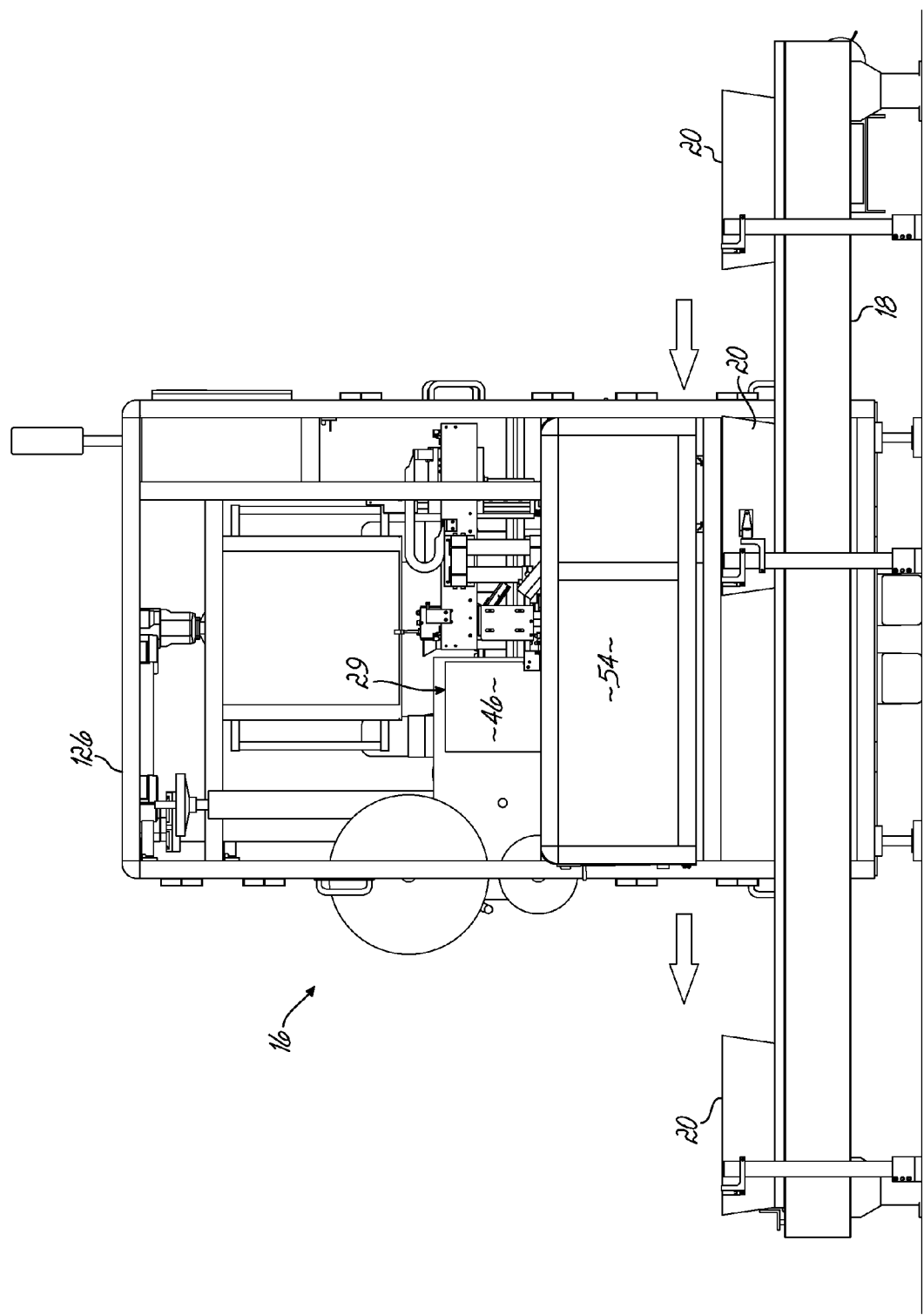
Figure 5:
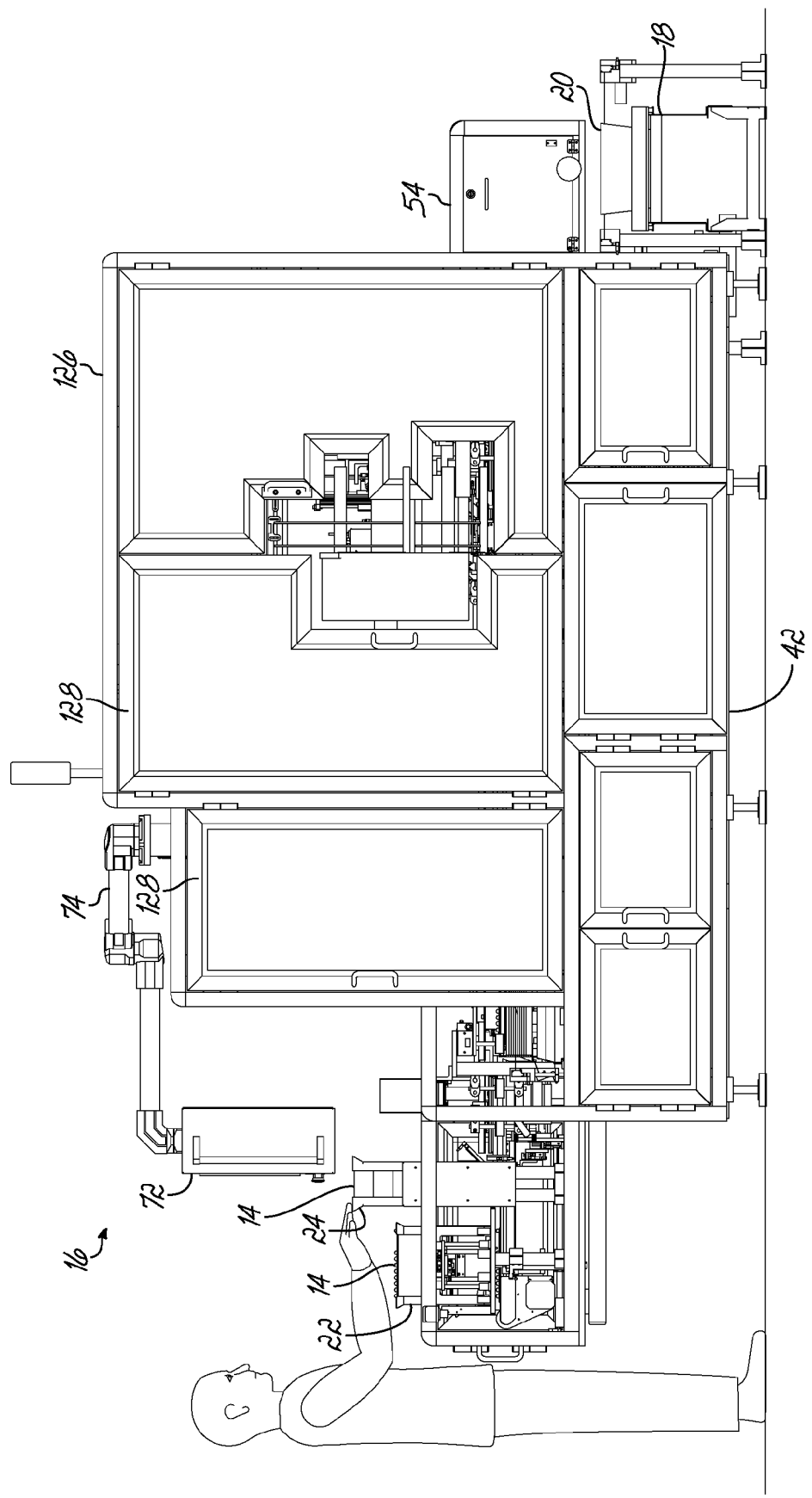
Figure 37:
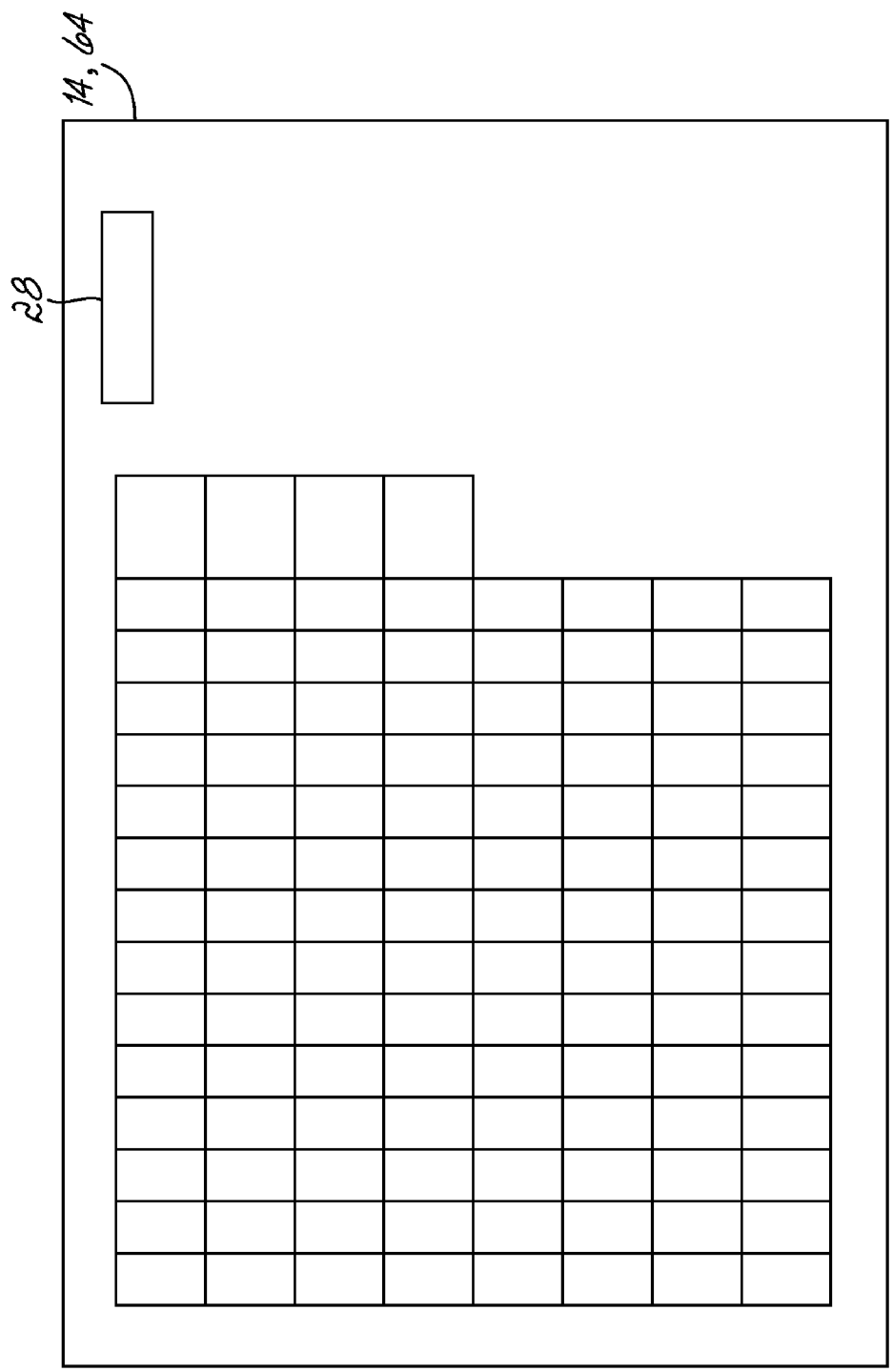
FIG. 37 is a schematic to plan view of a product shaped with the blister card form factor that is labeled and verified by the ALV machine.
Figure 38:
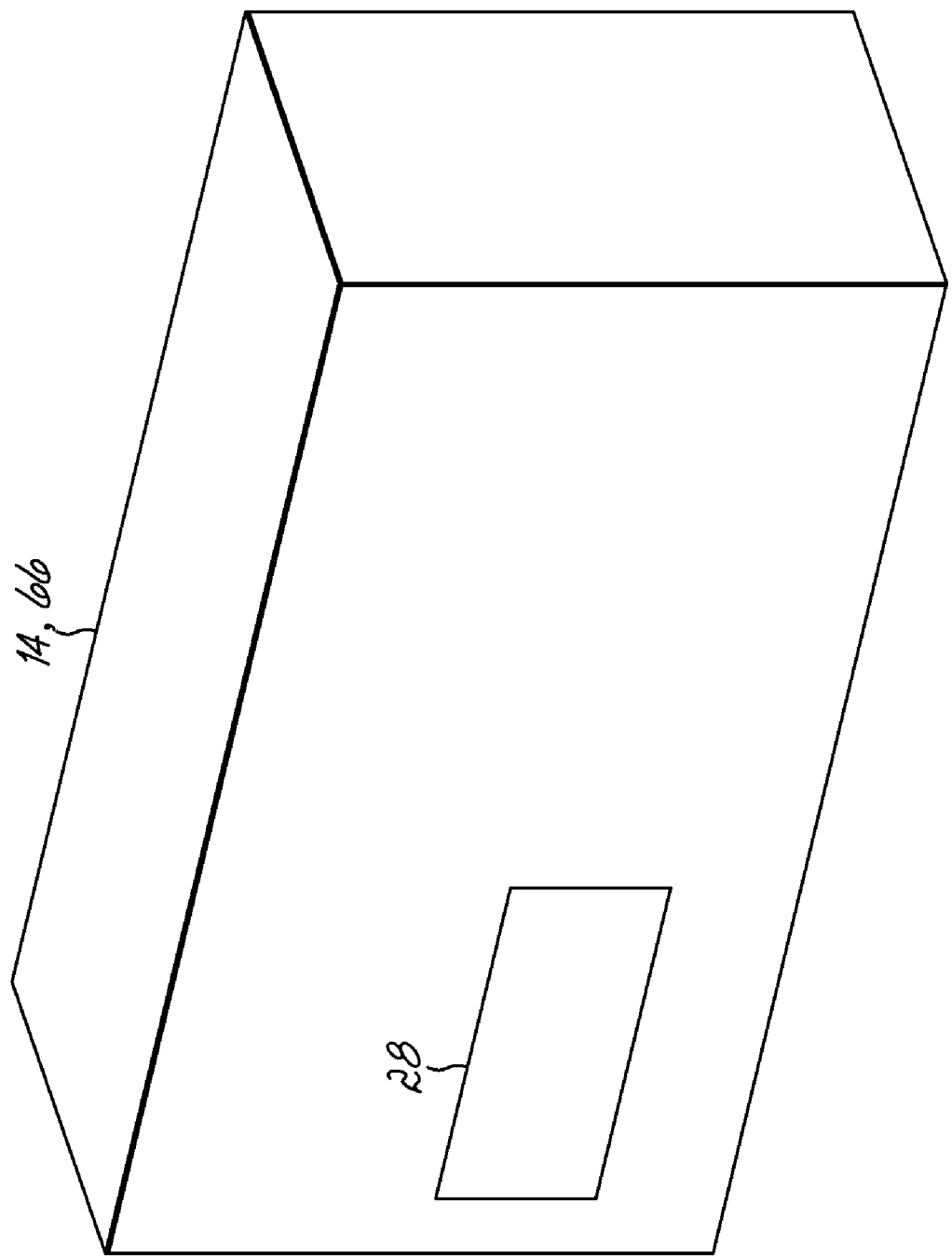
FIG. 38 is a schematic perspective view of a product shaped with the box form factor that is labeled and verified by the ALV machine.

With reference to FIGS. 1-5, an ALV station or system 10 includes a pick-to-light system, generally indicated by reference numeral 11, having pick-to-light racks 12 that hold bulk shipper cases containing products 14, an ALV Order Manager (AOM), an ALV (auto label verify) machine 16 that processes the products 14, and a tote handling system, in the representative form of a conveyor 18, that handles containers 20 receiving products 14 processed by the ALV machine 16. As best shown in FIGS. 3-5, the ALV machine 16 includes a product loading station in the form of product feed or induction magazines 22, 24, which are used to automatically induct products 14 pulled by an operator from the racks 12 of the pick-to-light system 11, and a first product verification and rejection (PVR1) station 26 configured to read a product barcode 28 (FIGS. 37 and 38) on each product 14 for verification of the inducted products 14 prior to labeling. The ALV machine 16 also includes a label print, verify, and apply (LPVA) station 29 used to print patient labels 30 (FIG. 36), verify a patient barcode 32 printed on each patient label 30, and apply each successfully-verified patient label 30 to the corresponding product 14. A second product verification and rejection (PVR2) station 34 of the ALV machine 16 re-verifies both the barcode 32 printed on the patient label 30 and the barcode 32 on the product 14, and checks that these barcodes 28, 32 match and correlate with known product tracking data before loading the labeled products 14 from the ALV machine 16 into one of the containers 20.

The tote handling system, which is tightly integrated with the operation of the ALV machine 16, continues the tracking of the verified and labeled products 14 to the final point of engagement by a technician or operator. In an alternative embodiment, the tote handling system may be robotic, instead of the representative conveyor 18.

Figure 23:
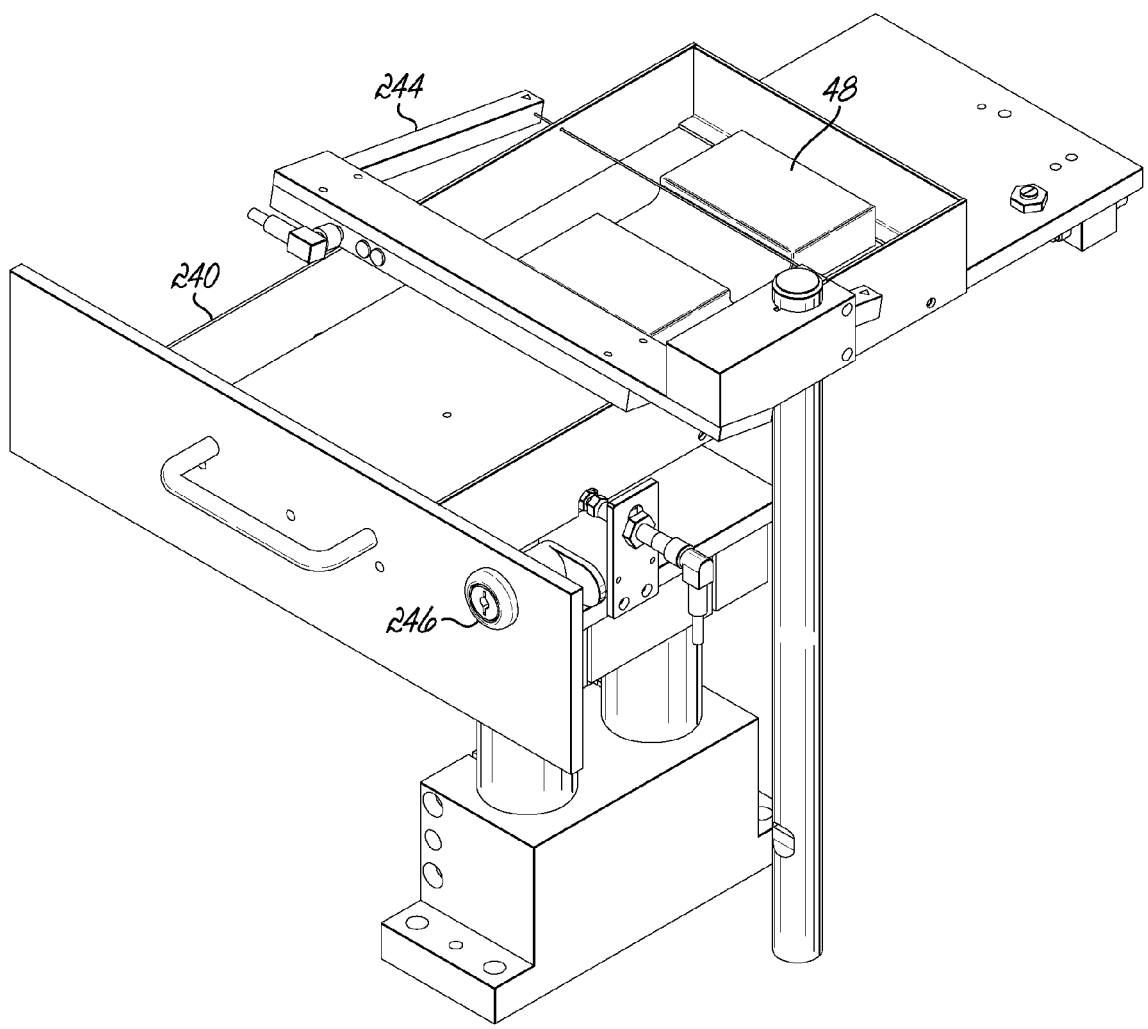
FIG. 23 is a perspective view of a faulty label platen associated with the label print, verify, and apply station of the ALV machine.
Figure 24:
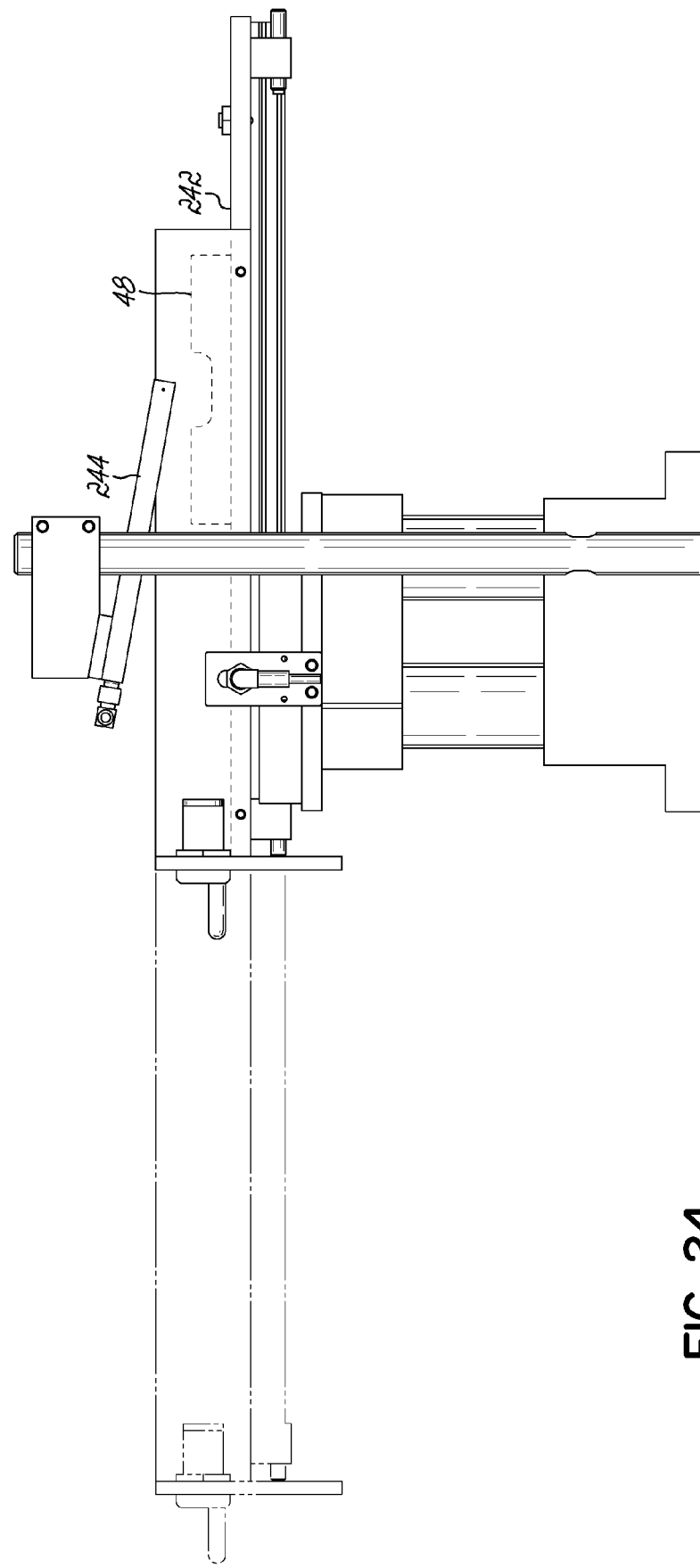
FIG. 24 is a side elevation view of the faulty label platen of FIG. 23.
Figure 25:
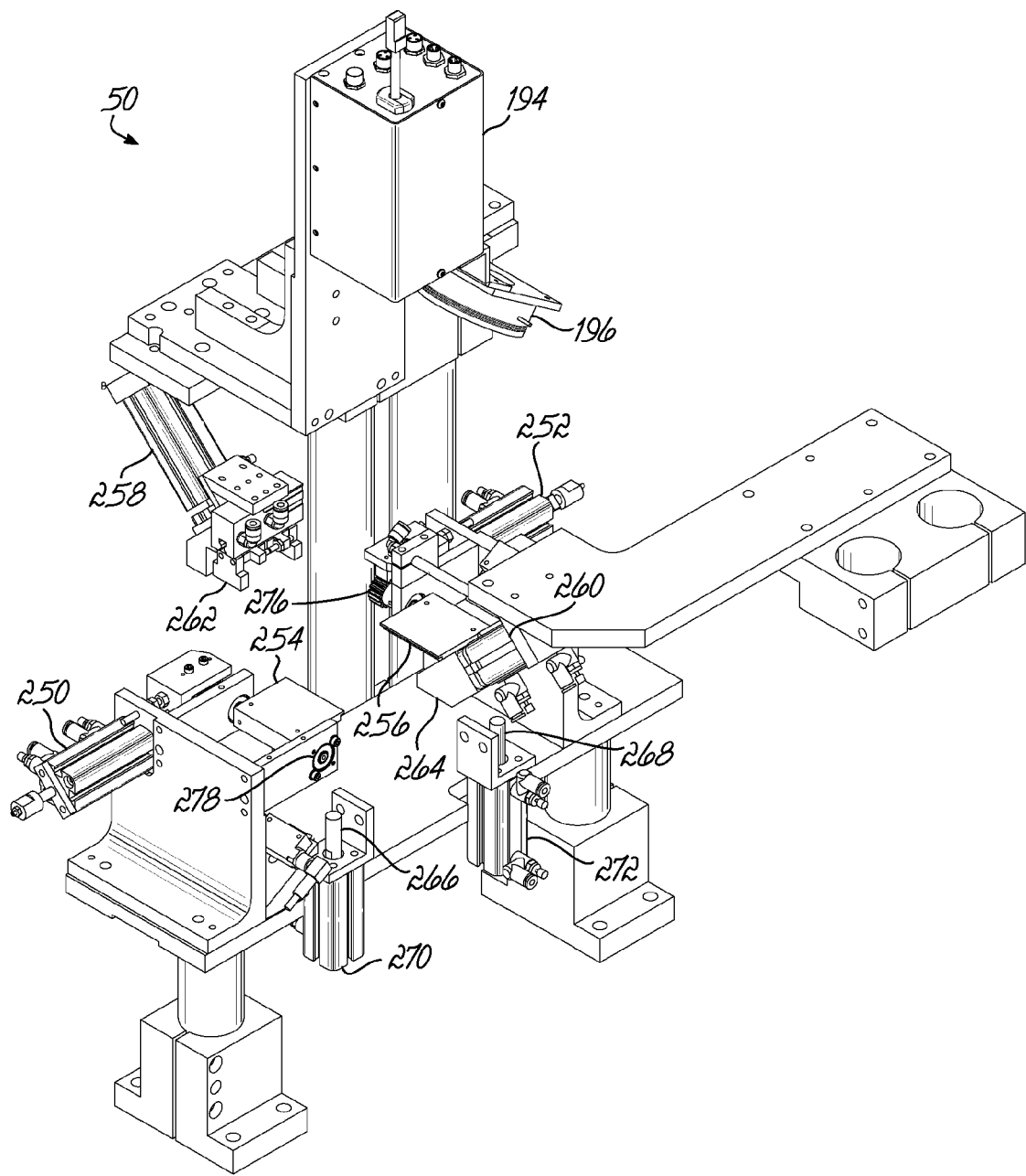
FIG. 25 is a perspective view of guide tooling associated with the label print, verify, and apply station of the ALV machine.
Figure 26:
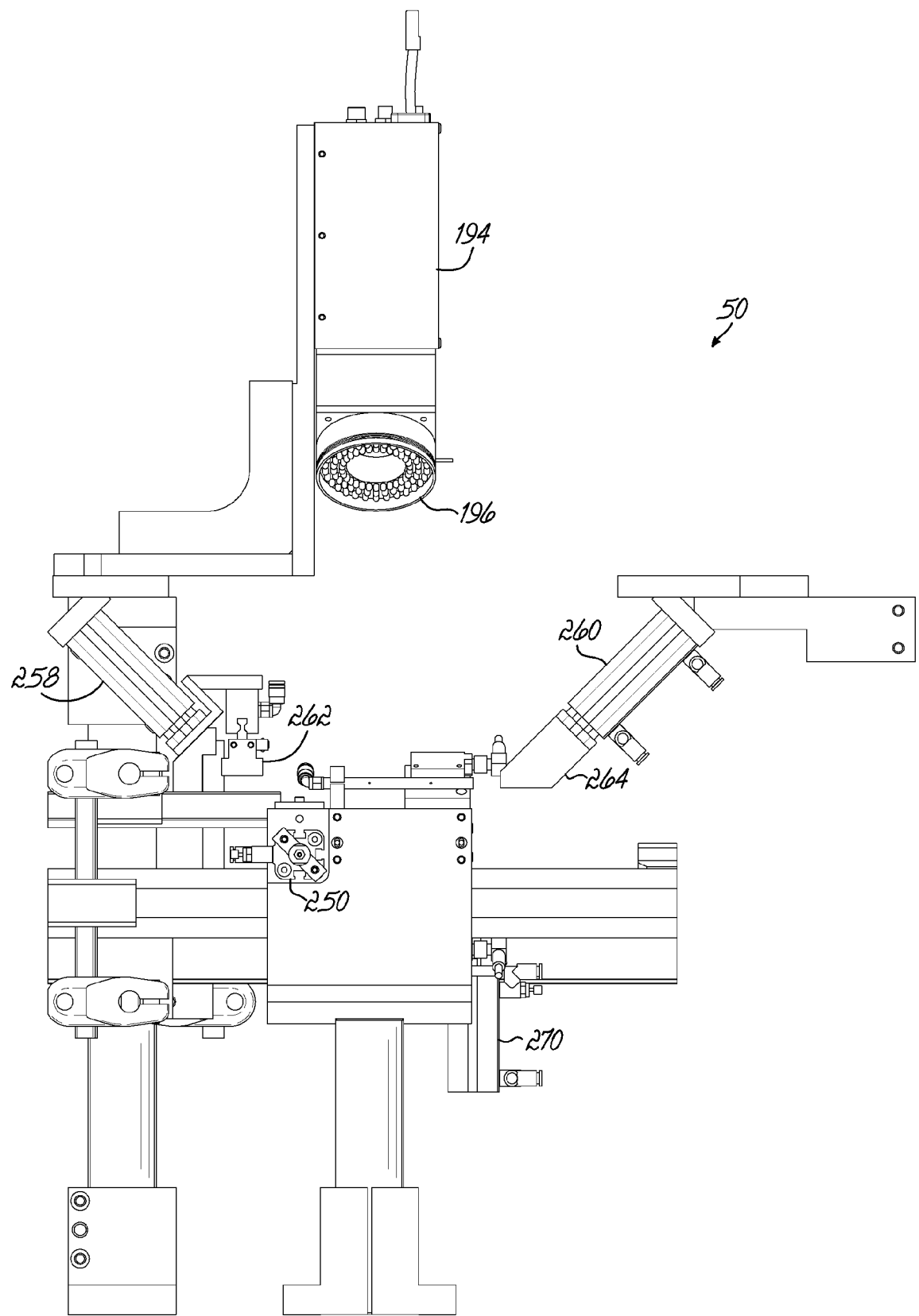
FIGS. 26 and 27 are side elevation and end elevation views, respectively, of the guide tooling of FIG. 25.
Figure 27:
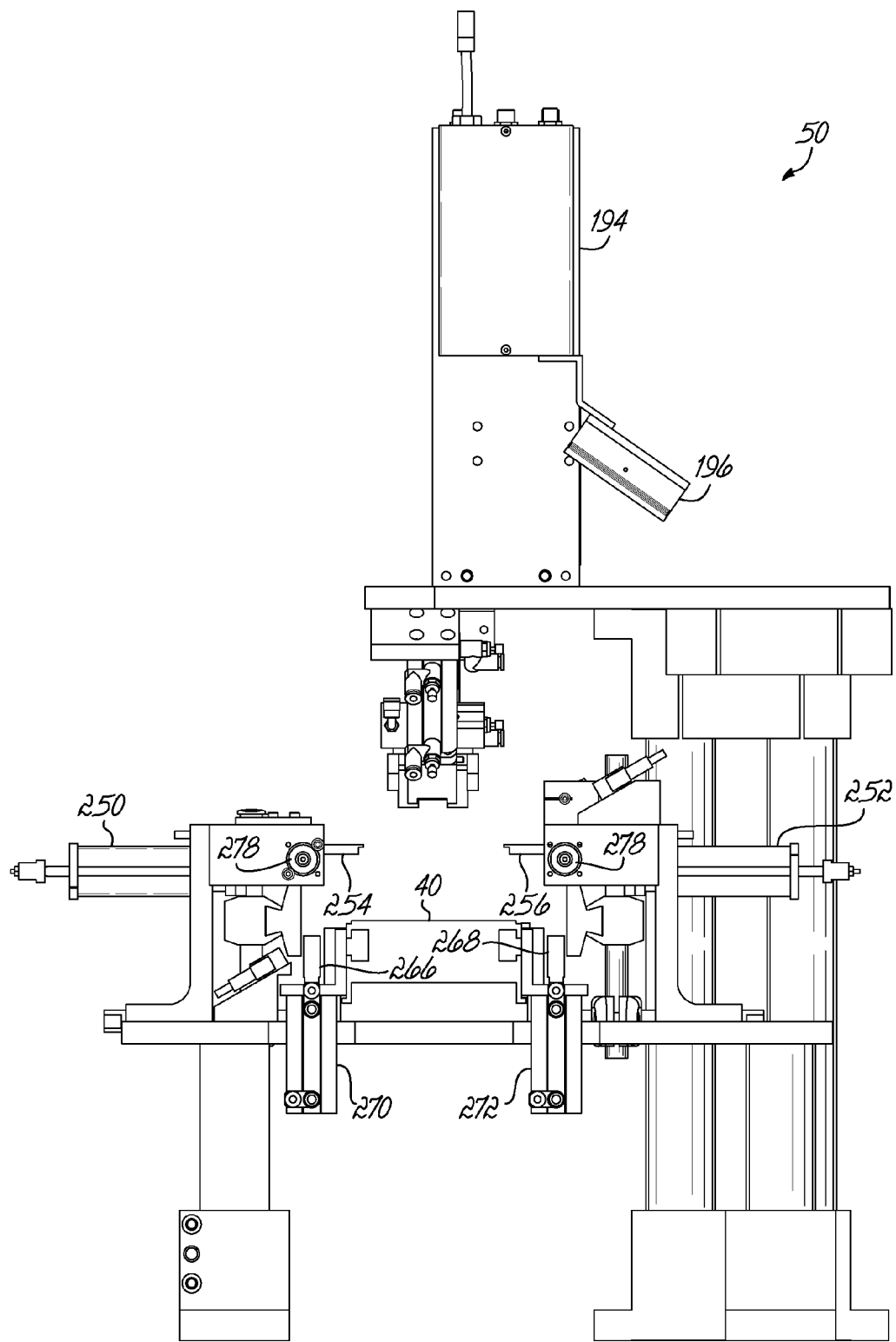

The product induction magazines 22, 24, PVR1 station 26, LPVA station 29, and PVR2 station 34 of the ALV machine 16 are arranged along the length of a product conveyor 40, which defines a linear workflow path for processing the products 14. The ALV machine 16 is supported above the pharmacy floor on a table 42. A reject bin 44, which represents a first reject station associated with the PVR1 station 26, receives products 14 that fail verification for one reason or another and, because of the failed verification, that are laterally displaced from the product conveyor 40 into the reject bin 44. The LPVA station 29 includes a label printer 46 used to print patient-specific information, including the patient bar code 32, onto patient labels 30 for the products 14 and a faulty label platen 48 (FIGS. 23, 24). The faulty label platen 48 receives those patient labels 30 printed by the label printer 46 but rejected as defective by vision inspection, because of an unreadable or unexpected barcode 32, before application at the LPVA station 29 to a product 14. Guide tooling 50 (FIGS. 25-27) is provided to secure the products 14 at the LPVA station 29 for the process applying one of the printed patient labels 30.

Figure 32:
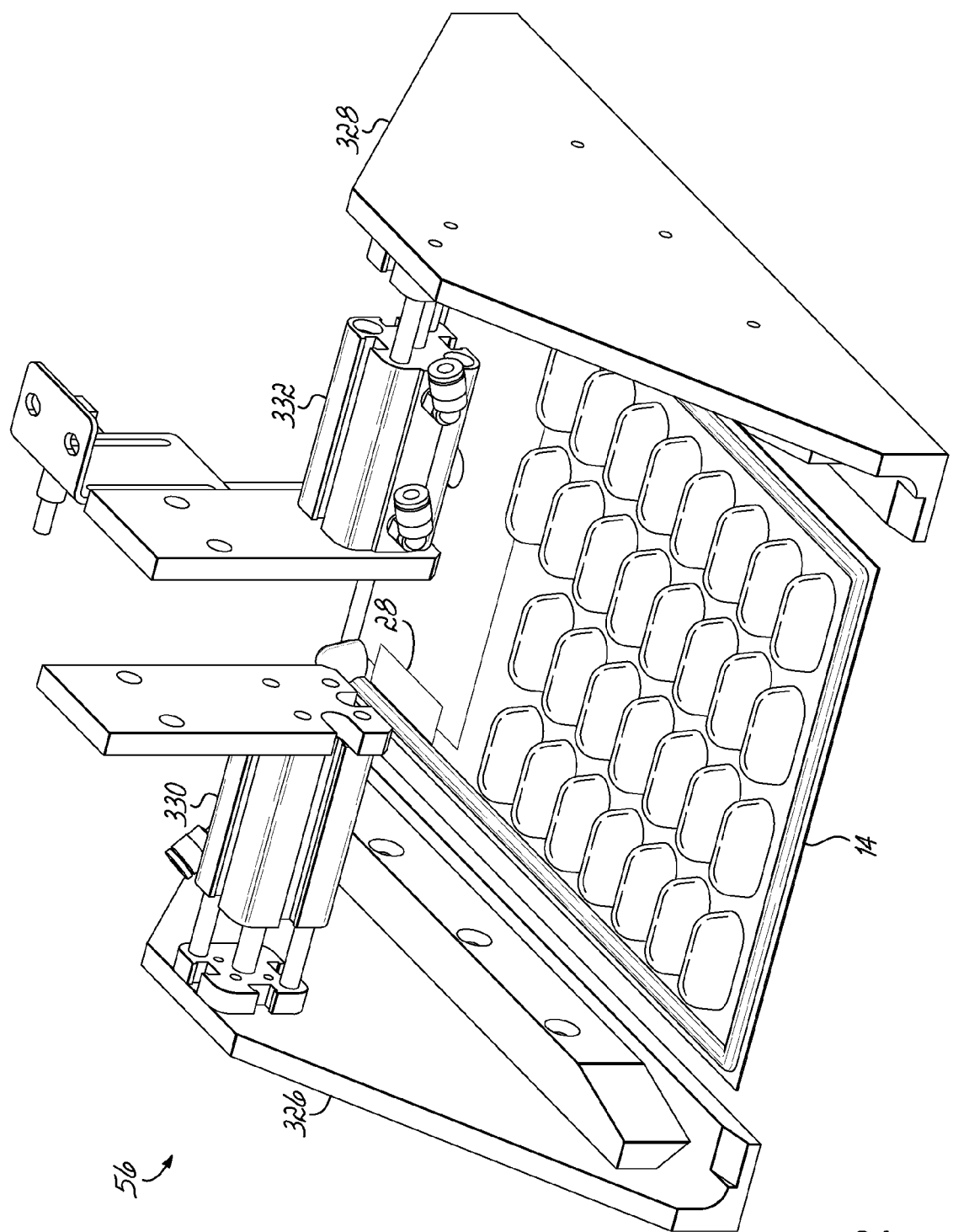
FIG. 32 is a perspective view of the package drop of the reject bin of FIG. 30.

A reject bin 54 representing a second reject station is located at the end of the product conveyor 40 for receiving products 14 that are labeled with one of the patient labels 30, but fail verification of either the product barcode 28 the patient barcode 32 at the PVR2 station 34. A package drop 56 (FIG. 32) is arranged at the terminal end of the product conveyor 40 that assists with the orderly drop of rejected products 14 into the reject bin 54. Labeled and verified products 14 are diverted from the PVR2 station 34 to an escape 58, which transfers labeled and verified products 14 into one of the containers 20 on the conveyor 18. One aspect of the ALV machine 16 is its ability to interchangeably handle products 14 of different form factors, as explained hereinafter, without any reconfiguration or alteration to the ALV machine 16.

In an alternative embodiment, a pharmacy can house multiple ALV systems (not shown) each identical or substantially similar to ALV system 10. The ALV systems 10 may constitute stand-alone stations in a non-integrated pharmacy, which is characterized by manual tote induction and removal, or components of an integrated (i.e., automated) pharmacy in which the individual systems 10 are linked together by a shared tote routing or conveyor system. In the latter instance, multiple ALV systems 10 inside the same pharmacy may be logically connected to one of the ALV systems 10, which is designated as the primary ALV system 10, via a communications channel, such as an Ethernet communications channel, and physically connected to the tote conveyor system shared by the multiple systems 10. The AOM of the primary ALV system 10 may be used to control one or more of the additional ALV systems 10 housed in the pharmacy.

The ALV system 10 represents an automated order dispensing system situated within the pharmacy that is used to dispense and fulfill drugs and prescriptions specified by customer orders. A customer order represents prescriptions delivered to a customer location (e.g., nursing station or unit) in a particular shipment from the pharmacy. Each patient order may be composed of one or more prescriptions and each individual prescription may include one or more products 14 of the card or box form factor. Each prescription represents a subset of a patient order and, in particular, represents a unique drug stock keeping unit (SKU) for one or more products 14 contained within a patient order. Each individual drug SKU may represent a unique medication or pharmaceutical type, strength, form factor for the product packaging, etc. Drug SKUs are assigned and serialized for inventory management at the source of the products 14. The products 14 may also include printed or labeled human-readable information, such as the manufacturer or supplier name, medication type, medication strength and description, lot number, expiration date, etc.

A patient order represents all products 14 destined for a particular patient. After the individual products 14 are verified and labeled by the ALV machine 16 and if the container 20 is not a shipping tote, each patient order is ultimately transferred from the container 20 into a shipping tote (not shown) that departs the pharmacy and is delivered to the customer location. Products 14 may be intermittently added to the customer order assembled in the shipping tote.

The containers 20 used by the ALV system 10 may constitute containers that perpetually remain inside the pharmacy (i.e., work-in-process totes), shipping totes used to deliver products 14 to a customer and representing or more sorted data attributes, or aisle (or section) totes representing one or more sorted data attributes. For example, during certain periods of a working day, products 14 may be placed directly into shipping totes. This may be an appropriate mode of operation for the ALV machine 16 to, for example, initiate automatic re-fills of prescriptions during overnight hours. Orders are picked on-demand by destination and processed by the ALV machine 16 directly into shipping totes. During other periods of a working day, products 14 processed by the ALV machine 16 may be placed into aisle (or section) totes instead of work-in-process totes and shipping totes. For example, during afternoon and early evening hours, orders can be picked on-demand by SKU and processed into aisle (or section) totes. As orders accumulate during the morning hours toward a peak work queue, products 14 processed by the ALV machine 16 may be picked by destination and processed into work-in-process totes. Multiple work-in-process totes are assigned to a destination.

In the representative embodiment, the ALV system 10 may be used to dispense and fulfill prescriptions in products 14 of at least two different form factors (in some Figures, the products 14 of two different form factors are depicted as overlapping to facilitate understanding). Products 14 of different form factors are generally characterized by different geometrical shapes. Irrespective of the particular form factor, the products 14 hold solid dosages of medications or pharmaceuticals that comprise a supply of a specific drug for an individual patient and constitutes a single prescription.

In one specific embodiment, the products 14 have exactly two different form factors. One form factor consists of prepackaged flat blister cards 64 (FIG. 37) holding dosages of pharmaceuticals in oral solid form. Another form factor for the products 14 consists of prepackaged cartons or boxes 66 (FIG. 38) containing individual thermoformed blister strips (not shown) holding dosages of pharmaceuticals in oral solid form. The blister cards 64 and the strips inside boxes 66 incorporate individual thermoformed blisters that have a hangable, punch-through backing or tab to aid removal of the pill or tablet (i.e., solid dosage) held in each blister.

The product barcode 28 on each product 14 reflects the contents of the package. Groups of products 14 in a common bulk shipper case typically share the same mutual product barcode 28. The product barcode 28 may be printed directly on a surface of the product 14 or, alternatively, may be printed on a label that is affixed to a surface of the product 14. The product barcode 28 is positioned on the product 14 so that, within the normal imprecision associated with its application, it is reproducible for purposes of the field of view of readers used by the ALV machine 16 to read the product barcode 28. To that end, the product barcode 28 on each of the products 14 of the card form factor may be positioned near one corner of the card 64 and inset slightly from the card perimeter. Similarly, the product barcode 28 on each of the products 14 of the box form factor may be positioned on a side wall of the box 66 at a specified set of distances from the box side edges. In any event, the positioning of the product barcode 28 on the products 14 is chosen such that the product barcode 28 is not obscured or obstructed after the application of the patient label 30 to the product 14.

When traveling on the product conveyor 40, the product barcode 28 on products 14 having the box form factor is visible on the right side of the box 66 (viewed from a perspective in the direction of product travel on the product conveyor 40). When traveling on the product conveyor 40, the product barcode 28 on products 14 characterized by the card form factor is visible on the front of the blister card 64 (viewed from a perspective above the card as the card travels along the product conveyor 40).

Figure 36:
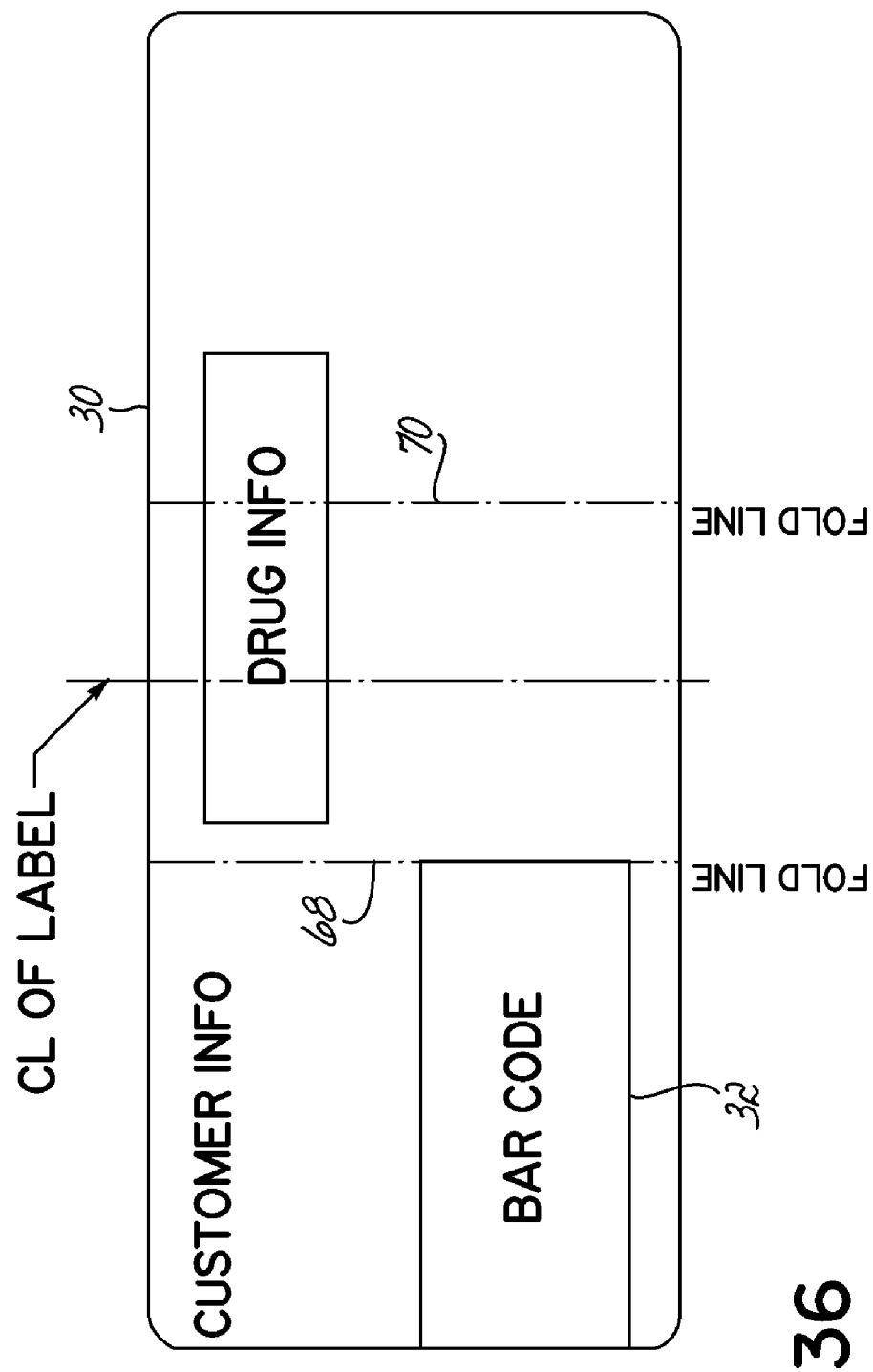
FIG. 36 is a schematic view of a patient label that is applied to the products by the ALV machine.

With reference to FIG. 36, the patient label 30, which is printed on conventional label stock, includes an adhesive backing for adhesively bonding the patient label 30 to the product 14. The patient barcode 32, which encodes information relating the prescription, is situated within a given spatial window or footprint inside the perimeter of the patient label 30. The ALV machine 16 is tolerant of slight inaccuracies in the precise location of the patient barcode 32 on the products 14 and on the patient label 30 for purposes of reading the patient barcode 32. The positioning of the patient barcode 32 on the labeled products 14 is reproducible to an extent necessary for purposes of the field of view of readers used by the ALV machine 16 to read the patient barcode 32. The patient label 30 may further include human-readable information relating to the drug or pharmaceutical contained in the product 14 and/or the customer for the pharmaceutical contained in the product 14.

The patient label 30 includes a pair of fold lines 68, 70 that are disposed on opposite sides of, and parallel with, the label centerline. The patient label 30 is applied with a folded arrangement on products 14 of the box form factor. Specifically, the patient barcode 32 and fold lines 68, 70 are disposed on the patient label 30 such that, when applied to products 14 of the box form factor, the patient barcode 32 is resides on one side wall of box 66 and the portion of the patient label 30 between the fold lines 68, 70 is applied to the top of box 66. The same patient label 30 can be applied to a landing zone near a leading edge of the products 14 having the card form factor with a planar arrangement in which the patient label 30 is not folded about the fold lines 68, 70.

In operation, the ALV system 10 is designed to ensure that a correct patient label 30 is applied to a correct product 14 and that the labeled product 14 placed by the ALV machine 16 into one of the containers 20. The ALV system 10 is designed to avoid causing physical damage (i.e., physical damage to the contained solid drug dosages, the drug packaging, the packaging integrity, or the package markings) to products 14 processed by the ALV machine 16.

Figure 6:
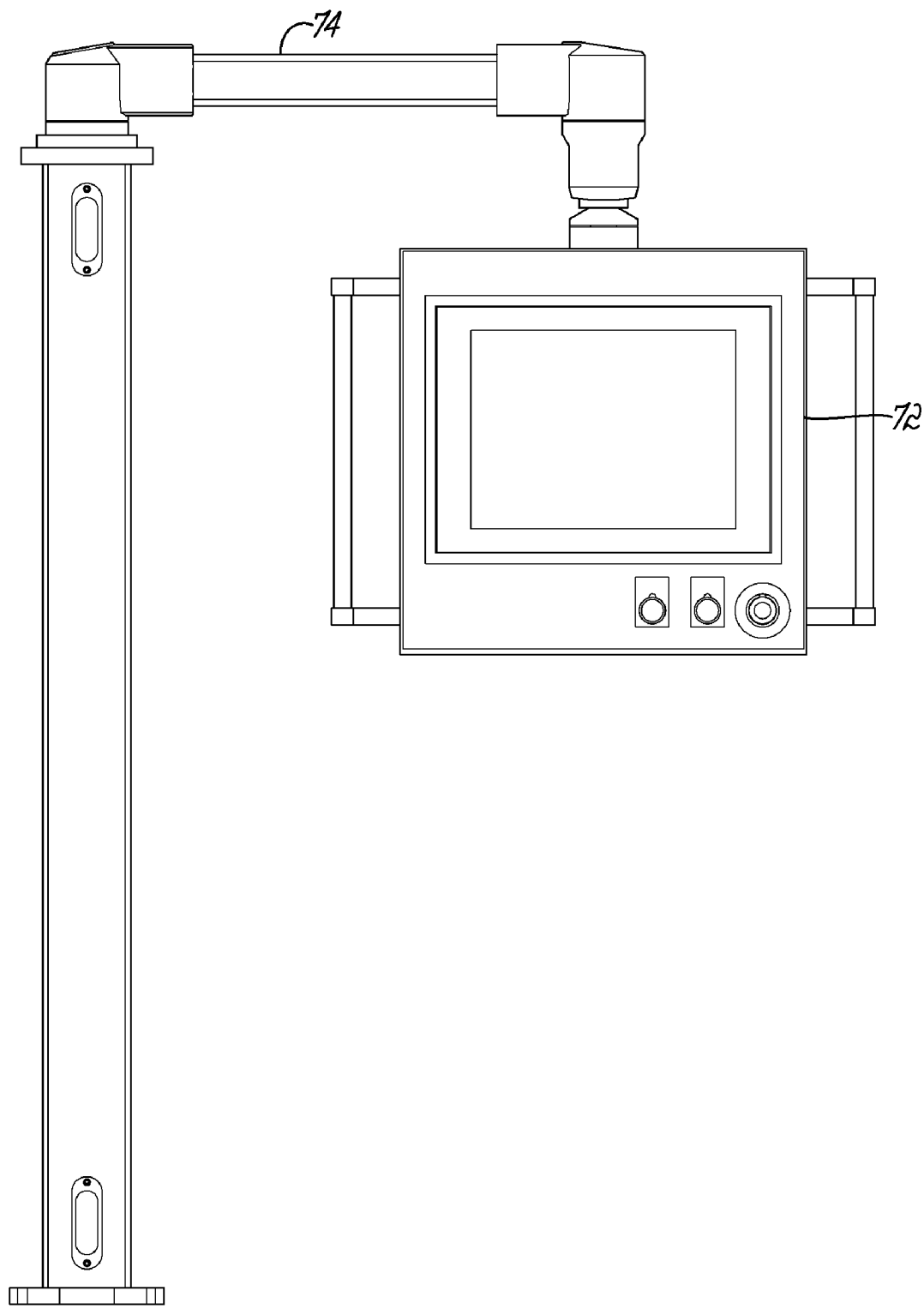
FIG. 6 is a front elevation view of an HMI computer of the ALV machine and a swing arm supporting the HMI computer.

The ALV machine 16 of the ALV system 10 is controlled by a controller 15 (FIG. 2), such as a programmable logic controller (PLC) or, in a specific embodiment, an Allen-Bradley CompactLogix PLC. The controller 15 may include one or more central processing units (CPUs) for processing programmable components contained in a memory card or extendable memory, a power supply unit, an input/output control module, and other components recognized by a person having ordinary skill in the art. The controller 15 is programmed with a series of program components having a series of algorithms for controlling the mechanical functions of the ALV machine 16, as well as operating as an input/output interface to the various barcode readers, motors, and product stops contained in ALV machine 16 and an input/output interface to a human machine interface (HMI) computer 72 (FIG. 6). These program components may be stored in memory and executed by one of the CPUs within the controller 15.

The controller 15 is used to coordinate and orchestrate the mechanical functions of the ALV machine 16. The communications interface(s) may comprise any common communications channel technology recognized by a person having ordinary skill in the art, including but not limited to Ethernet, Fieldbus (CAN/CAN OPEN), or Serial (RS-232) protocols. The controller 15 tracks product data associated with each of the products 14 inducted by the product induction magazines 22, 24 into the ALV machine 16 and subsequently processed at the PVR1 station 26, LPVA station 29, and PVR2 station 34. Product information and status from the tracking data can be displayed and updated on demand at the HMI computer 72.

With reference to FIG. 6, the HMI computer 72 may run any conventional operating system and may execute different software applications that cooperate with the operation of the controller 15 for controlling the processing of products 14 in the ALV machine 16. The HMI computer 72, which permits the operator to interact with the ALV machine 16, may comprise a touch sensitive display or computer screen that promotes operator interactions. The HMI computer 72 may implement a Graphical User Interface (GUI) on the computer screen that features frames and panes with buttons and specific interface components for operator interaction in connection with test, set up, and run procedures of the ALV system 10.

The HMI computer 72 is suspended from one end of an articulated swing arm 74 at an elevated location near product induction magazines 22, 24 of the ALV machine 16. By manipulating the swing arm 74, the operator can swing the HMI computer 72 into a position that permits the operator to setup and control the ALV machine 16.

The HMI computer 72 communicates over a communications channel, such as Ethernet, with a pharmacy host. The pharmacy host is a computer system that communicates with, and gives tasks to, the ALV system 10. The pharmacy host may be, for example, a warehouse management system or a warehouse control system. This pharmacy host tracks inventory in the pharmacy and tracks and directs orders through the pharmacy.

The AOM of the ALV system 10 includes multiple processors (not shown) that implement software applications and collectively process orders and pick requests received from the pharmacy host. The computers, which are coupled together by a communications channel such as Ethernet, include a pick server, a real time pick-to-light computer (PickPC), a statistics computer (StatPC), and an order reconciliation computer. The PickServer, PickPC, and StatPC may be rack mounted servers physically mounted in the ALV machine 16 or housed in the pharmacy, as appropriate. The PickServer, PickPC, and StatPC may be constructed with fault tolerant redundant power supplies and hot swappable Redundant Array of Independent Disks (RAID) drives. The order reconciliation computer may comprise a desktop personal computer and an interfaced hand-held barcode scanner that can be mounted anywhere in the pharmacy. The operation of the AOM is described below.

Orders in the form of pick request data are communicated from the pharmacy host to the ALV system 10. The pick requests are stored in an AOM database for logical grouping based on user-defined parameters and retrieval. The logical grouping process results in pick batches for the operator to pick from the pick-to-light racks 12. Each pick batch can contain one or more products 14 destined for a placement into one of the containers 20.

Each of the pick-to-light racks 12 in the pick-to-light system 11 includes a bay controller (not shown) and multiple shelves 80 (FIG. 2) arranged in levels. Each of the shelves 80 is partitioned by dividers 82 to define multiple bins or inventory locations that are within arms-reach of a technician and stocked with one or more bulk shipper cases or containers. Each bulk shipper case holds products 14 characterized by a unique drug SKU. More than one inventory location, typically adjacent inventory locations, in the pick-to-light racks 12 can hold bulk shipper cases holding products 14 with the same drug SKU, which are managed as a single unit by the ALV system 10. Most drug SKUs have a single inventory location on the shelves 80 of the pick-to-light racks 12, although products with faster moving drug SKUs can be assigned to multiple inventory locations.

Figure 1:
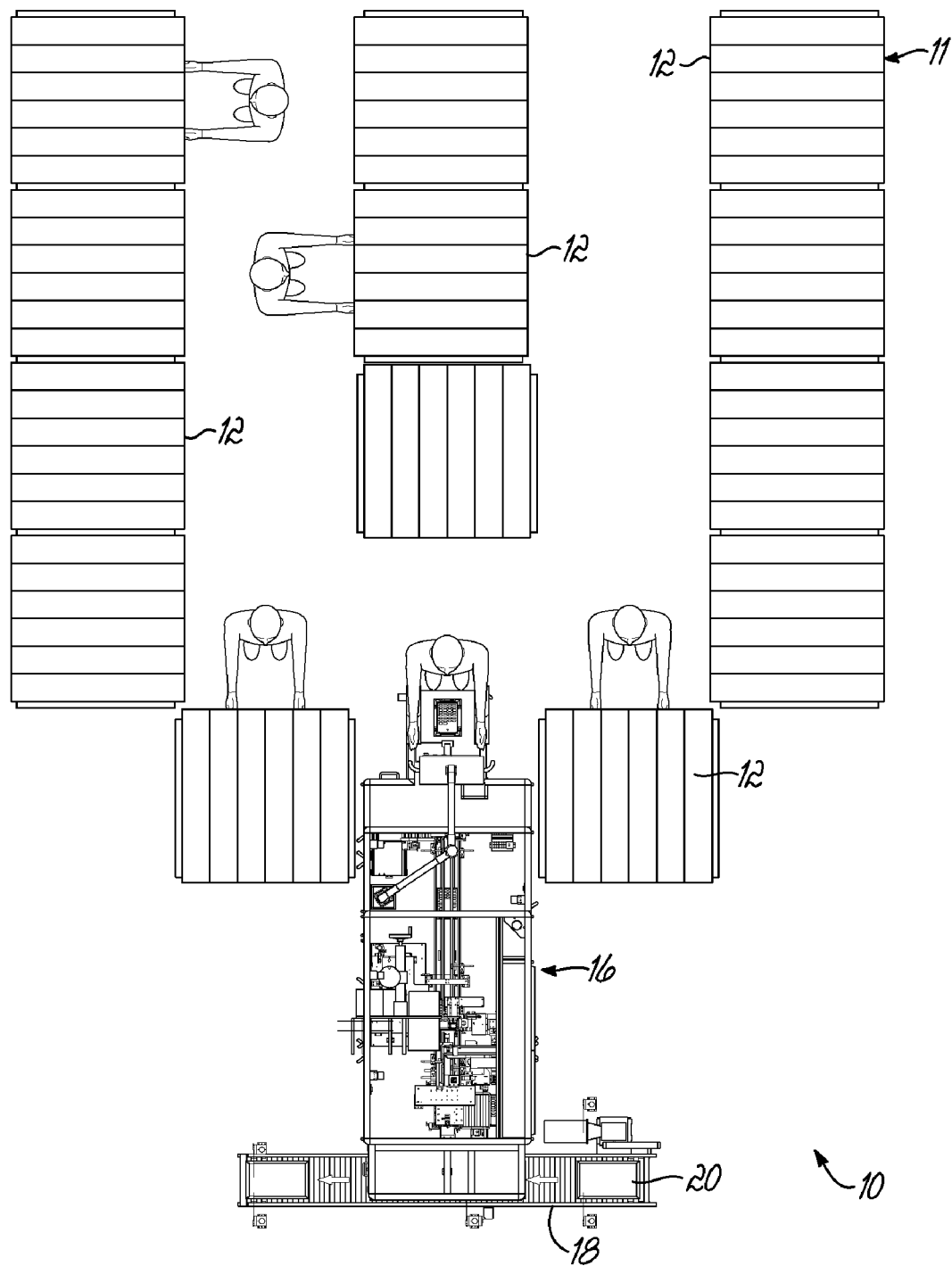
FIGS. 1 and 2 are top plan and side elevation views, respectively, of an embodiment of an ALV system.

As shown in FIG. 1, the pick-to-light racks 12 surround the operator in a configurable arrangement, along with central stand-alone racks 12. Some or all of the individual racks 12 of the pick-to-light system 11 may be supported on castors that ease re-configuration of the arrangement relative to the ALV machine 16. The peripheral pick-to-light racks 12 may be arranged in, for example, a U-shape to minimize and optimize the walking distance along the aisles from the inventory locations of the pick-to-light system 11 to the ALV machine 16. However, the pick-to-light racks 12 may have another configuration may be chosen to accommodate spatial constraints in the pharmacy or a design choice. The vertical position and inclination angle of the shelves 80 in the pick-to-light racks 12 may be adjustable. The pick-to-light racks 12 may be arranged to locate specific inventory locations for products 14 of faster moving drug SKUs closer to the product induction magazines 22, 24 of the ALV machine 16.

Each inventory location in the pick-to-light racks 12 has a dedicated pick-to-light module (not shown) with a pick face that includes an indication light, one or more buttons, and an alphanumeric display module. The alphanumeric display indicates to the operator the number of products to be picked for an order, and the buttons permit the operator to adjust the quantity up, or down, if there are inventory issues. The adjustments provide a means for the operator to update the AOM database with real-time accurate inventory counts of products 14. Each of the pick-to-light racks 12 may include other types of pick-to-light modules, such as an order control module, that are operated under the control of the bay controller.

In the workflow sequence for the ALV system 10, an operator is instructed to pick individual products 14 from the pick-to-light system 11 with visual queues supplied by the indication lights associated with the inventory locations. The indication lights on the pick-to-light modules assist the operator to quickly and accurately identify the inventory locations in the pick-to-light racks 12 for each pick batch. The operator picks products 14 from the lighted inventory locations, adjusts for any inventory if needed using the buttons on the pick face, and presses a pick complete button on the pick face of the inventory locations. The operator repeats this process until all lighted inventory locations in the pick-to-light racks 12 are acknowledged, which indicates to the controller 15 that the operator has completed the pick batch.

Figure 7:
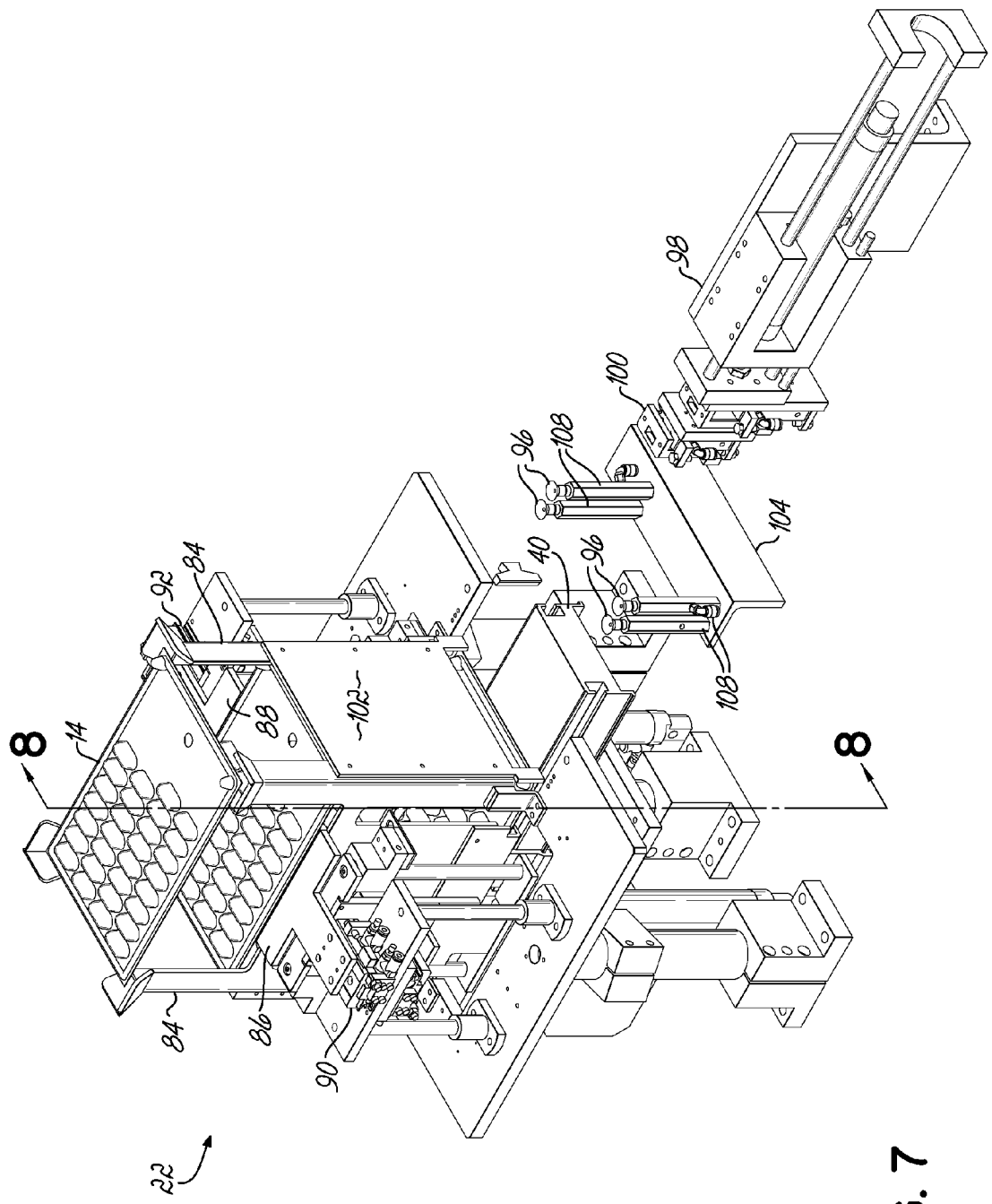
FIG. 7 is a perspective view of a card induction magazine and the card singulator of the ALV machine.
Figure 8:
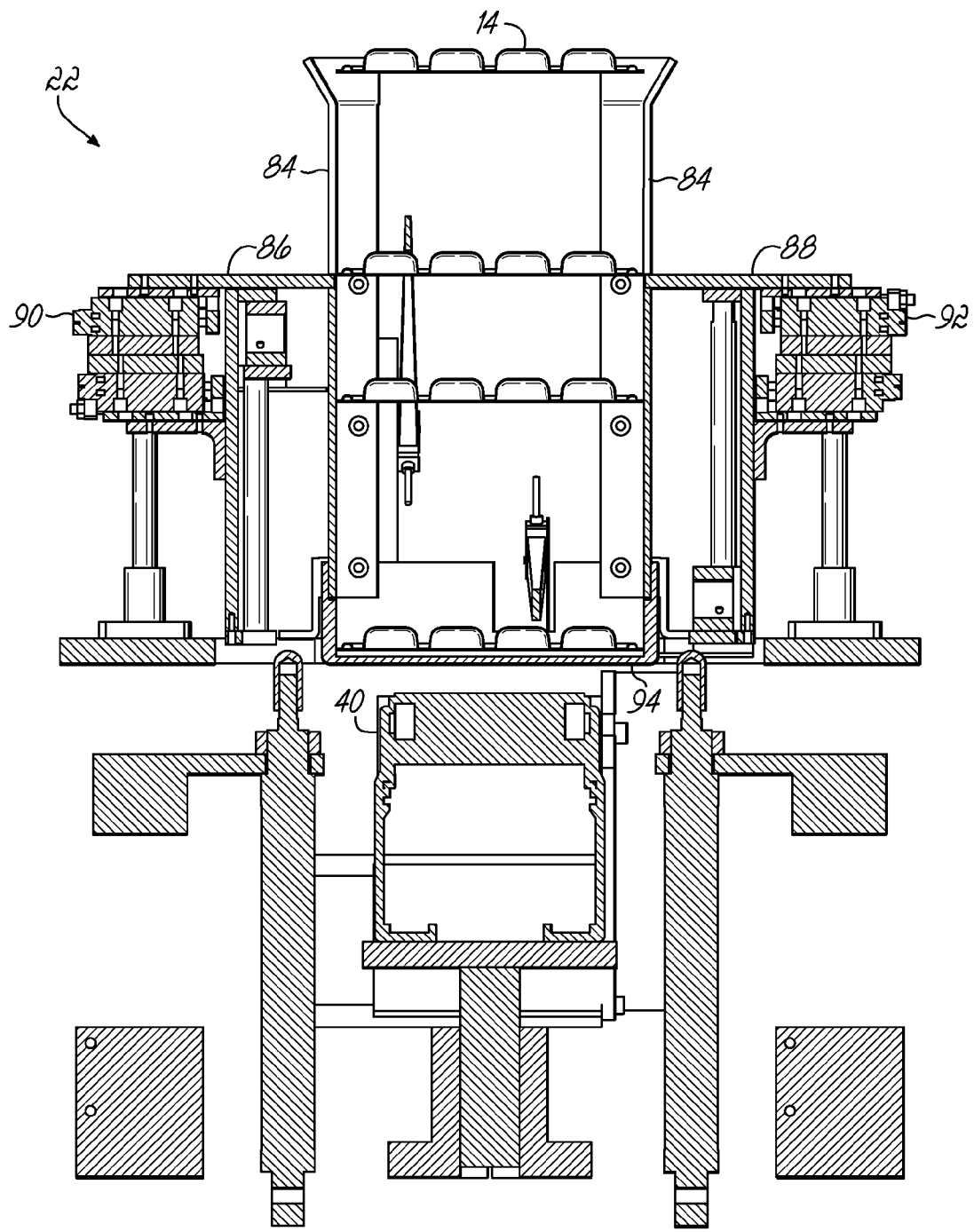
FIG. 8 is a cross-sectional view taken generally along line 8-8 in FIG. 7.
Figure 9:
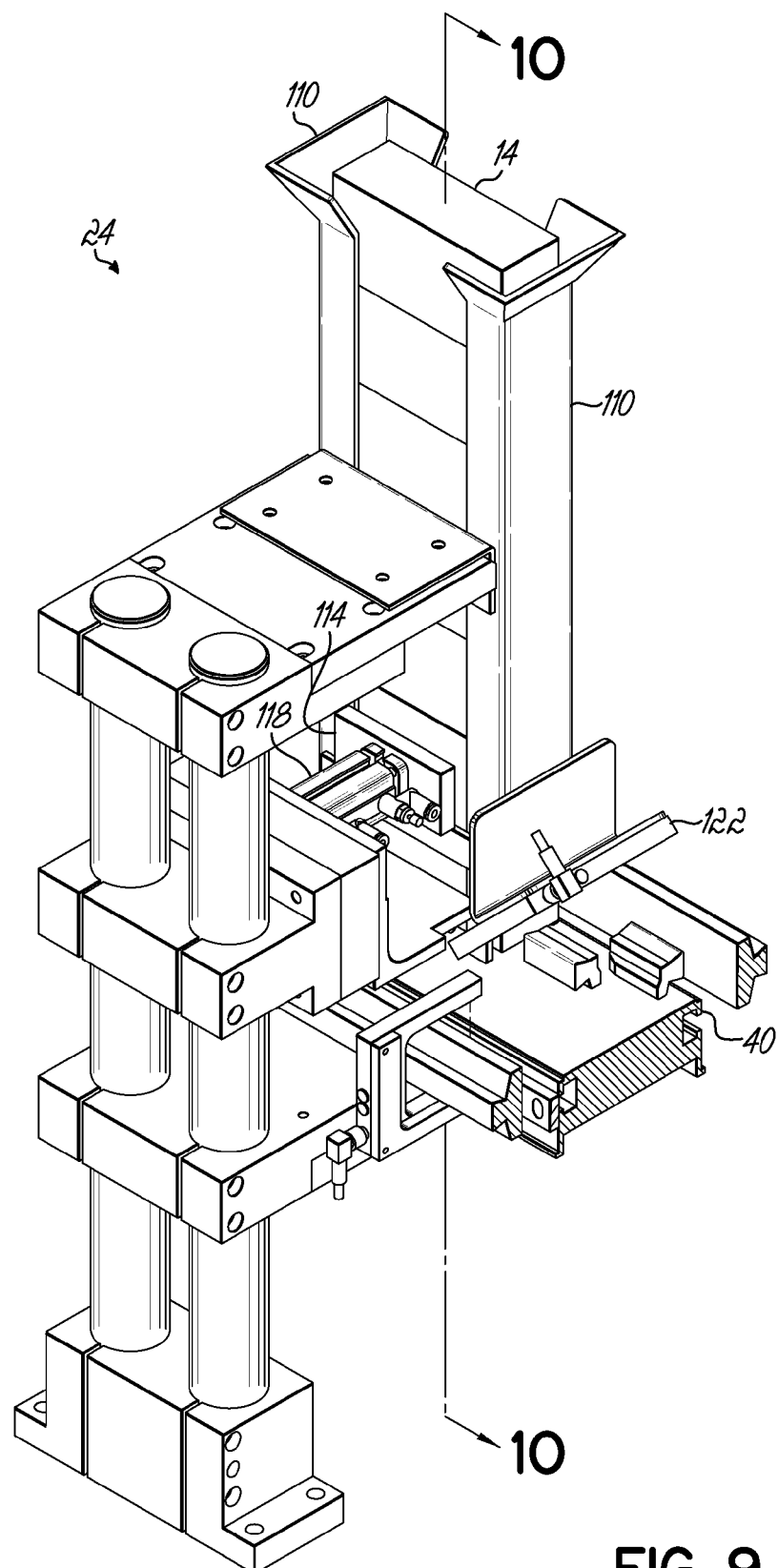
FIG. 9 is a perspective view of a box induction magazine of the ALV machine.
Figure 10:
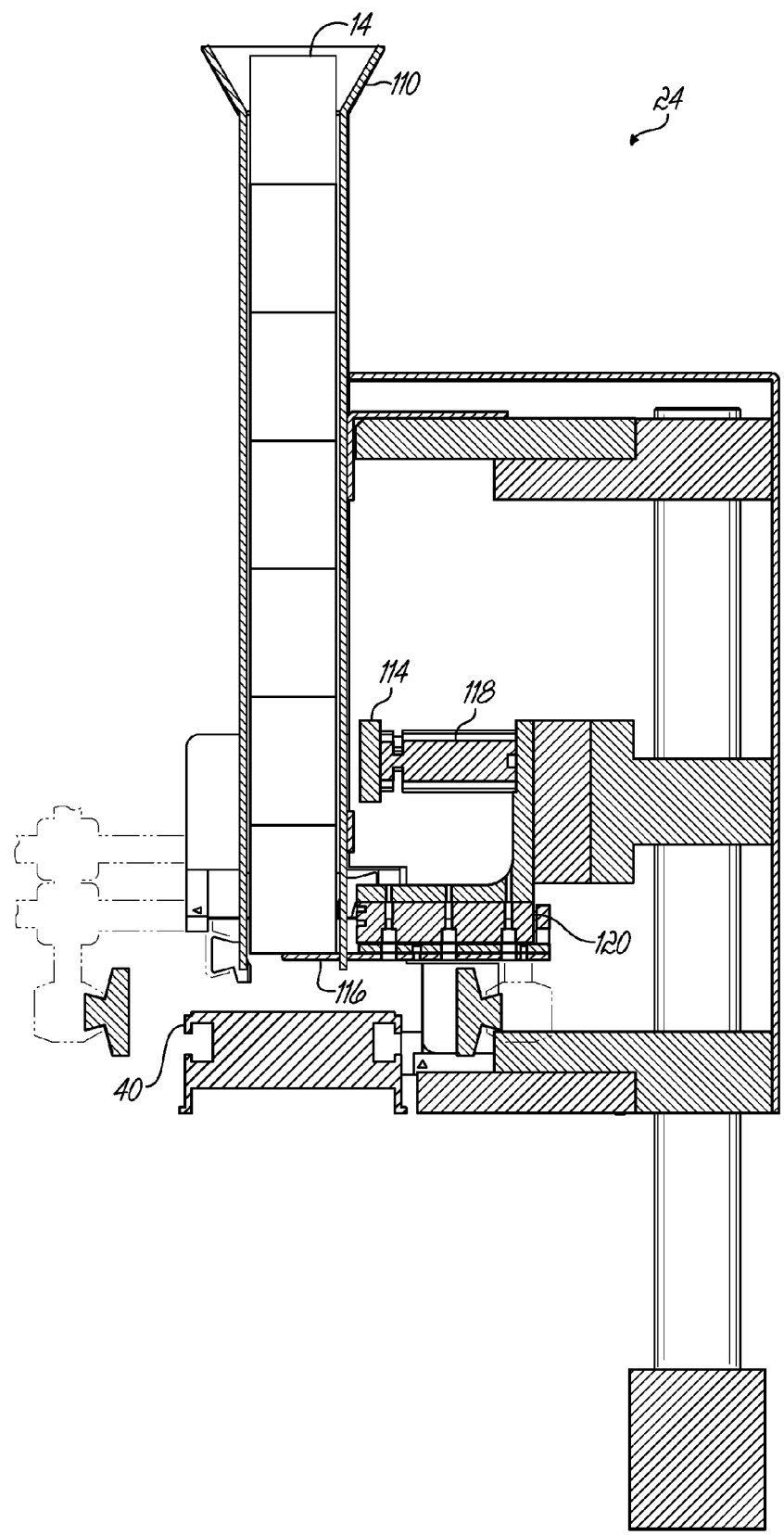
FIG. 10 is a cross-sectional view taken generally along line 10-10 in FIG. 9.

With reference to FIGS. 7-10, the product induction magazines 22, 24 are used to feed products 14 to the ALV machine 16 from either a completed or partially completed pick batch. The product induction magazines 22, 24 may be configured to handle different form factors of products 14. In particular, and as best shown in FIGS. 7 and 8, one product induction magazine 22 may be configured for feeding picked products 14 in the representative form of the flat blister cards 64 (FIG. 37) shaped with the card form factor into the ALV machine 16. As best shown in FIGS. 9 and 10, the other product induction magazine 24 may be configured for inducting picked products 14 in the representative form of the cartons or boxes 66 (FIG. 38) shaped with the carton or box form factor into the ALV machine 16. The chutes of each of the product induction magazines 22, 24 are dimensioned to permit the operator to load the appropriate products 14 in the correct orientation with a single hand through the use of lead-ins and tapers, which minimizes the requirement for precise positioning. As a consequence of having two distinct product induction magazines 22, 24, the ALV machine 16 is endowed with an ability to interchangeably handle products 14 of the different form factors without any reconfiguration or alteration to the machine 16.

With reference to FIGS. 7 and 8, the product induction magazine 22 for products 14 shaped with the card form factor (for example, flat blister cards 64 (FIG. 37)) includes a set of columnar guide posts 84 that collectively define a feed chute and a pair of movable arms 86, 88 that are arranged to extend and retract through respective gaps between an adjacent pair of guide posts 84 into the space inside the chute. The guide posts 84, which are formed from right angle bar stock, have concave L-shaped vertical channels arranged relative to each other to correlate with the shape of products 14 having the card form factor so that one outside corner of the card projects into an inside corner represented by the concave vertical channel of the nearest guide post 84. At the top entrance of the chute, the channel of each of the guide posts 84 is flared outwardly to increase the cross-sectional area available to receive the product 14, which eases introduction of products 14 dropped by the operator into the chute.

Each of the arms 86, 88 is coupled mechanically with a respective linear motion mechanism in the form of a linear actuator 90, 92 for movement relative to the chute between extended and retracted positions. When the arms 86, 88 are placed in the extended position, a portion of each of the arms 86, 88 contacts and supports opposite sides of the bottom product 14 in a stack of products 14 manually dropped by the operator into the chute of the product induction magazine 22. The channels in the guide posts 84 collectively guide the vertical movement of the products 14 from the top of the feed chute downward so that the bottom product 14 in the stack rests on the arms 86, 88. When the controller 15 instructs both linear actuators 90, 92 to withdraw the arms 86, 88 outwardly to the retracted position, the group of products 14 is no longer supported and falls under the influence of gravity. The bottom product 14 in the stack rests on a platen 94 of the product induction magazine 22 that is located beneath the arms 86, 88. The landing zone for the products 14 on platen 94 is located centrally between the guide posts 84, which collectively guide the downward movement of the products 14 onto the platen 94. The stack of products 14 resting on the landing zone of the platen 94 is then singulated by the product induction magazine 22, as described below.

The product induction magazine 22 further includes a set of suction devices 96, a linear motion mechanism 98, a vertical motion mechanism 100, and a blocking plate 102 that cooperate to singulate products 14 of the card form factor to the product conveyor 40. The suction devices 96 are carried on a head 104 mounted to one end of the linear motion mechanism 98, which has the form of a linear actuator like a slide table with an output coupled with the head 104. The blocking plate 102 is supported between two of the guide posts 84 of the chute with a gap between a bottom edge of the blocking plate 102 and the nearest edge of the platen 94. When supported on the platen 94, the underside of the leading end (i.e., the end on which the patient label 30 is subsequently placed) of the bottom product 14 of the card form factor is accessible through this gap.

The suction devices 96 are situated on respective vertical fingers 108 projecting from the head 104. The fingers 108 have a spaced arrangement such that suction devices 96 straddle the width of the product conveyor 40. As a result, the linear motion mechanism 98 can be actuated by the controller 15 to an extended position, without contacting the product conveyor 40, in which the suction devices 96 are positioned in the gap to underlie the leading end of the product 14 and a retracted position in which the bottom product 14 of the stack is extracted from the chute. When the controller 15 is ready to place another product 14 of the card form factor on the product conveyor 40, the linear motion mechanism 98 moves the head 104 so that the suction devices 96 underlie the leading end of the product 14 resting on the platen 94. The suction devices 96 are moved vertically toward this leading end by the vertical motion mechanism 100, which has the form of a linear actuator, like a slide table, in the representative embodiment.

Suction is supplied to the suction devices 96 from a vacuum source (not shown) so that the suction devices 96 aspirate the air from the space between the suction device 96 and the product 14 to apply an attractive force that engages the leading end of the product 14 with the head 104. With the product 14 so grasped, the vertical motion mechanism 100 moves the head 104 and suction devices 96 downward by a distance sufficient for the leading end of the product 14 to clear the bottom edge of the blocking plate 102. The linear motion mechanism 98 then retracts the head 104 by a distance sufficient to withdraw and release the product 14 from the chute. The suction devices 96 are then vented, which releases the attractive force applied to the singulated product 14, and the vertical motion mechanism 100 moves the head 104 downwardly so that the product 14 is deposited onto a belt 106 (FIG. 11) of the product conveyor 40.

The solenoid valves for the linear actuators 90, 92 and vacuum source for the suction devices 96 are electrically coupled with, and controlled by, the controller 15. Sensors are provided that detect the presence of one or more products 14 captured by the arms 86, 88 and one of the products 14 residing on the platen 94. These sensors supply feedback to the controller 15 for operating the solenoid valves for the linear actuators 90, 92 and vacuum source for the suction devices 96.

These actions by the product induction magazine 22 serve to singulate the products 14 of the card form factor one at a time onto the product conveyor 40, which carries the singulated products 14 with a spaced relationship away from the product induction magazine 22 and downstream toward to a first product stop of the PVR1 station 26. When the card clears a sensor that detects the presence of the product 14 at product conveyor 40, the product 14 of the card form factor is added to the conveyor tracking data.

As described hereinabove, the product induction magazine 22 includes a first stage that accumulates one stack of products 14 and a second stage that singulates a different stack of products 14. This permits the operator to "work ahead" to pick a second stack of products 14 as instructed by the controller 15 via the pick-to-light system 11 while an initial stack of products 14 is singulated onto the product conveyor 40. The second stack may comprise part of the same pick order or a different pick order.

With reference to FIGS. 9 and 10, the product induction magazine 24 is constructed to release one product 14 of the box form factor (for example, boxes 66 (FIG. 38)), as required, onto the product conveyor 40 for processing in, and transport through, the ALV machine 16. The product induction magazine 24 includes a feed chute defined by a pair of guide posts 110, an upper movable arm 114, and a lower movable arm 116 spaced vertically below the upper movable arm 114. The guide posts 110 have concave U-shaped vertical channels arranged relative to face each other and dimensions to correlate with the shape of products 14 having the box form factor. At the entrance of the chute, the guide posts 110 are flared outwardly to ease introduction of products 14 into the chute.

The upper movable arm 114 is arranged and oriented to extend and retract through a gap between the guide posts 110 into the space inside the chute. The stroke of the upper movable arm 114 is sufficient to contact a side wall of one of the products 14 sitting in the chute. The lower movable arm 116 is configured to extend and retract to a location between the bottom of the chute and the top of the belt 106 (FIG. 11) of the product conveyor 40. The stroke of the lower movable arm 116 is sufficient to underlie and support the bottom product 14, when extended, in a suspended state above the belt 106 of the product conveyor 40. When retracted, the lower movable arm 116 releases the bottom product 14 to drop onto the product conveyor 40. The upper and lower movable arms 114, 116 are each coupled mechanically with a respective linear motion mechanism in the form of a linear actuator 118, 120, such as a slide table, for movement relative to the chute between extended and retracted positions. The linear actuators 118, 120 are electrically coupled with, and controlled by, the controller 15. Sensors are provided that detect the presence of products 14 supported by upper and lower movable arms 114, 116 and supply electrical signals as feedback to the controller 15 for use in controlling the operation of the linear actuators 118, 120.

In use, the operator introduces a stack of products 14 shaped with the box form factor between the guide posts 110 defining the chute. When a sensor detects the presence of products 14, the controller 15 instructs the linear actuator 120 to extend the lower movable arm 116. The bottom product 14 contacts and is supported by the lower movable arm 116, which suspends the bottom product 14 above the belt 106 of the product conveyor 40. The upper movable arm 114 operates as a box hold back that contacts the nearest-neighbor product 14, if any, adjacent to the bottom product 14 in the stack and, thereby, presses this product 14 against the opposite one of the guide posts 110. This restrains the vertical movement of this product 14. The controller 15 instructs the upper movable arm 114 to move to the extended position to contact product 14, if any, adjacent to the bottom product 14 in the stack.

The operation of the upper and lower movable arms 114, 116 is coordinated to singulate the products 14 onto the product conveyor 40. Consequently, the controller 15 instructs the lower movable arm 116 to periodically move to the retracted position, as needed, to release the bottom one of the products 14 in the stack within the chute onto the product conveyor 40. Sensor 122, which is located downstream from the chute of the product induction magazine 24, is configured to detect the presence of one of the products 14 in the box form factor on the product conveyor 40. Once the product 14 of the box form factor clears the sensor 122, the product 14 is added to the conveyor tracking data. After release, the controller 15 instructs the linear actuator 120 to extend the lower movable arm 116, which returns the lower movable arm 116 to its initial location within the chute, and instructs the linear actuator 118 to retract the upper movable arm 114. This releases the next product 14, which falls onto and is caught by the lower movable arm 116 where it is supported until the controller 15 instructs the linear actuator 120 to move the lower movable arm 116 for releasing this product 14 onto the product conveyor 40.

When singulating products 14, the ALV machine 16 loads tracking data received from the AOM for all picked products 14 to a queue. The ALV system 10 then waits for the operator to retrieve the appropriate products 14 from the pick-to-light system 11 and load these products 14 into the product induction magazines 22, 24. When all products 14 within the pick batch are placed into one of the product induction magazines 22, 24, the operator presses a pick batch induction complete button on the HMI computer 72. This action prompts the AOM to light the indication lights of the subsequent pick batch for the operator to initiate collection of the appropriate products 14 from the various inventory locations in the pick-to-light racks 12 while the ALV machine concurrently begins processing the previous batch's products.

The controller 15 adds products 14 to the conveyor tracking data when each specific product 14 clears the singulator of one of the product induction magazines 22, 24. Subsequent products 14 remain in the magazine queues maintained by the PLC until the product 14 currently on the product conveyor 40 is verified at PVR1 station 26. This permits the operator to pick ahead, while allowing the product induction magazines 22, 24 to continue to singulate and feed products 14 individually to the product conveyor 40.

The product induction magazines 22, 24 of the ALV machine 16 individually induct the products 14 within the pick batch without operator intervention and feed them to the conveyor 18 in a singulated fashion. The products 14 are individually transported through the ALV machine 16 with temporal and spatial separations between adjacent products 14. Specifically, the ALV machine 16 singulates the products 14 from the appropriate one of the product induction magazines 22, 24 based on the form factor of the first product 14 in the product queue and the form factor of the product 14 currently on the product conveyor 40. If the next product 14 in the queue has the box form factor and there is no product 14 at, or released to, first product stop of the PVR1 station 26, product induction magazine 24 is signaled to release another product 14 having the box form factor. If the next product 14 in the queue has the card form factor and there is no product 14 at or released to the first product stop of the PVR1 station 26, product induction magazine 22 is signaled to release another product 14 having the card form factor.

The ALV machine 16 is housed within guarding in the form of an enclosure 126 (FIG. 5) that restricts access to the constituent machinery and shields the operator from the moving components of the ALV machine 16. The enclosure 126 may include transparent or translucent panels that permit the operator to view the operation of the ALV machine 16 and guard doors 128. The guard doors 128 may be opened, or even removed, to access moving components of the ALV machine 16 without moving the pick-to-light racks 12. For safety purposes, the guard doors 128 may be secured by locking interlock switches that remain locked when the ALV machine 16 is powered. Opening of any one of the guard doors 128, or use of a manual override, designates all in-process products 14 inside the ALV machine 16 as rejects and tracks the rejected packages 14 into reject bins. Of course, the chutes of the product induction magazines 22, 24 are accessible to the operator from the outside of the enclosure 126 for inducting products 14. If the enclosure 126 is violated by an unauthorized entry, all assessable products 14 may be flagged for immediate rejection as to maintain the highest integrity.

Figure 11:
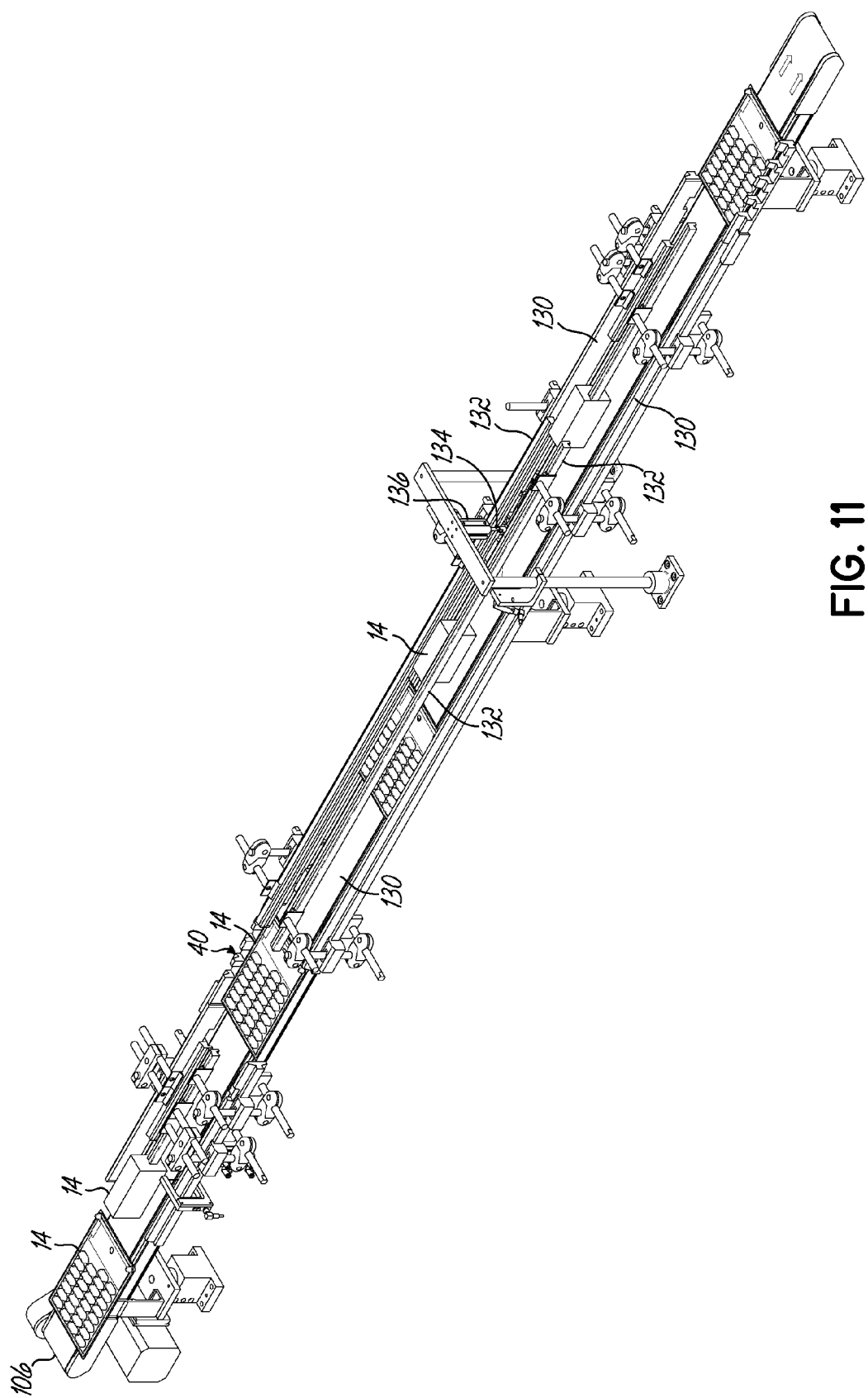
FIG. 11 is a perspective view of a product conveyor of the ALV machine.
Figure 12:
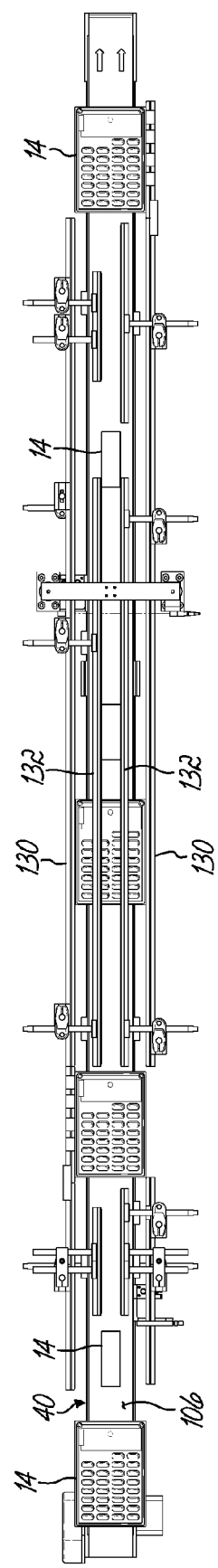
FIGS. 12 and 13 are top plan and end elevation views, respectively, of the product conveyor of FIG. 11.
Figure 13:
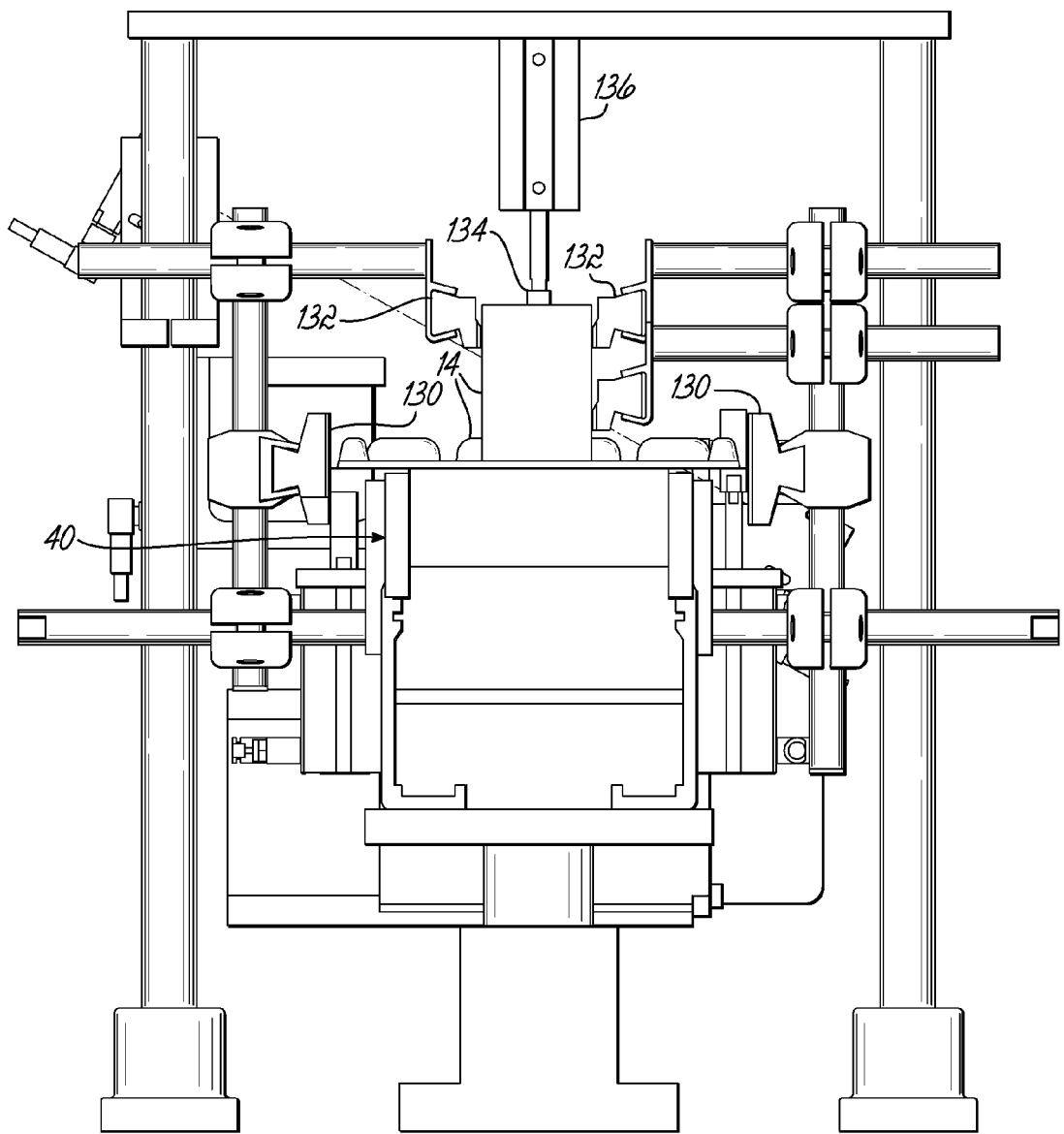

With reference to FIGS. 11-13, the product conveyor 40 serially transports the singulated products 14 to the different constituent components in the ALV machine 16. The product conveyor 40 generally includes a belt 106 looped about a pair of spaced apart pulleys, an electric drive motor, and a transmission, such as a gear box, that transfers motive power from the drive motor to one of the pulleys for moving the belt 106 about the pulleys. The product conveyor 40 is equipped to transport products 14 of both form factors through the ALV machine 16 without any reconfiguration or alteration to the machine 16, which promotes flexibility in the machine's capabilities in filling customer orders.

The products 14 are guided during the verification and labeling process in the ALV machine 16 between rails that straddle the belt 106 of product conveyor 40. More specifically, the ALV machine 16 utilizes a set of rails 130 for products 14 having the blister card form factor and another set of rails 132 for products 14 having the box form factor. The rails 130, 132, which have the form of parallel bars or strips extending along substantially the entire length of the product conveyor 40, are configured to positively control and track the products 14 at all times as they pass through the ALV machine 16. The rails 132 for products 14 having the box form factor are in a plane elevated above a plane containing the rails 130 for products 14 having the card form factor. This difference in elevation is required as the products 14 having the box form factor project a greater height above the top surface of the belt 106 of the product conveyor 40 than products 14 of the card form factor.

The bars of the rails 130, 132 are segmented to incorporate discontinuities or gaps adequate in length for moving rejected products 14 from the product conveyor 40 into the reject bin 44 (FIG. 3) or for moving labeled and verified products 14 from the product conveyor 40 onto the escape 58. The rails 130, 132 are configured to minimize the potential for damage, marking, or other harm to the products 14, and operate to prevent the products 14 of both form factors from jamming, hanging up, popping out, or changing orientation while being transported by the product conveyor 40.

A product stop 134 is used under the control of the controller 15 to temporarily block the transport of specific products 14 on the continuously moving belt 106 for staged delivery to the LPVA station 29. The product stop 134 is mechanically coupled with a linear actuator 136 in the form of a pneumatic cylinder that actuates an output to move the product stop 134 between an extended position in which the product 14 is contacted and held stationary and a retracted position out of the travel path of products 14 on the product conveyor 40. The linear actuator 136 is controlled by a solenoid valve electrically coupled with the controller 15 for actuation by applying and venting air pressure as understood by a person having ordinary skill in the art.

Figure 14:
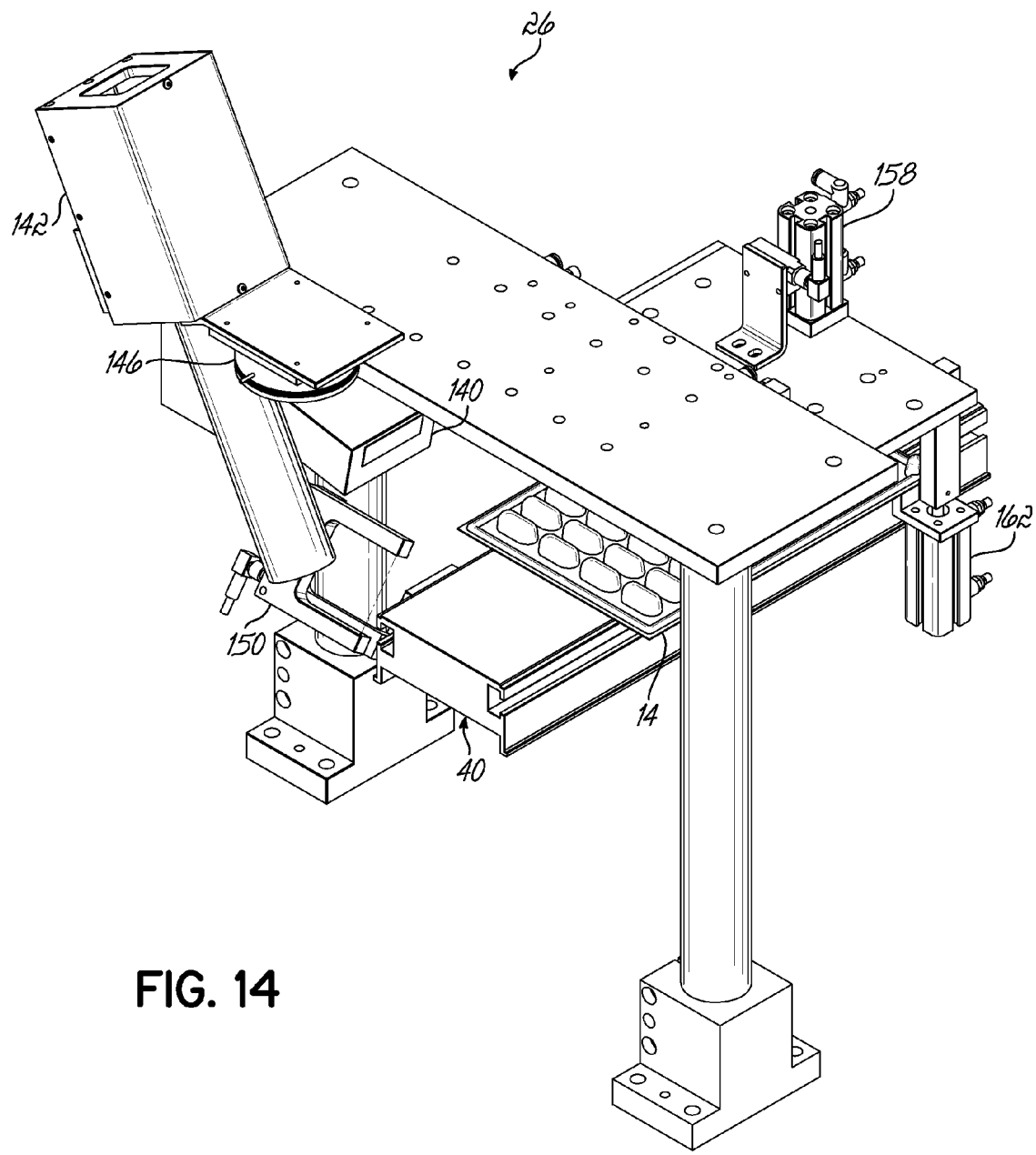
FIG. 14 is a perspective view of a first product verification and rejection station of the ALV machine.
Figure 15:
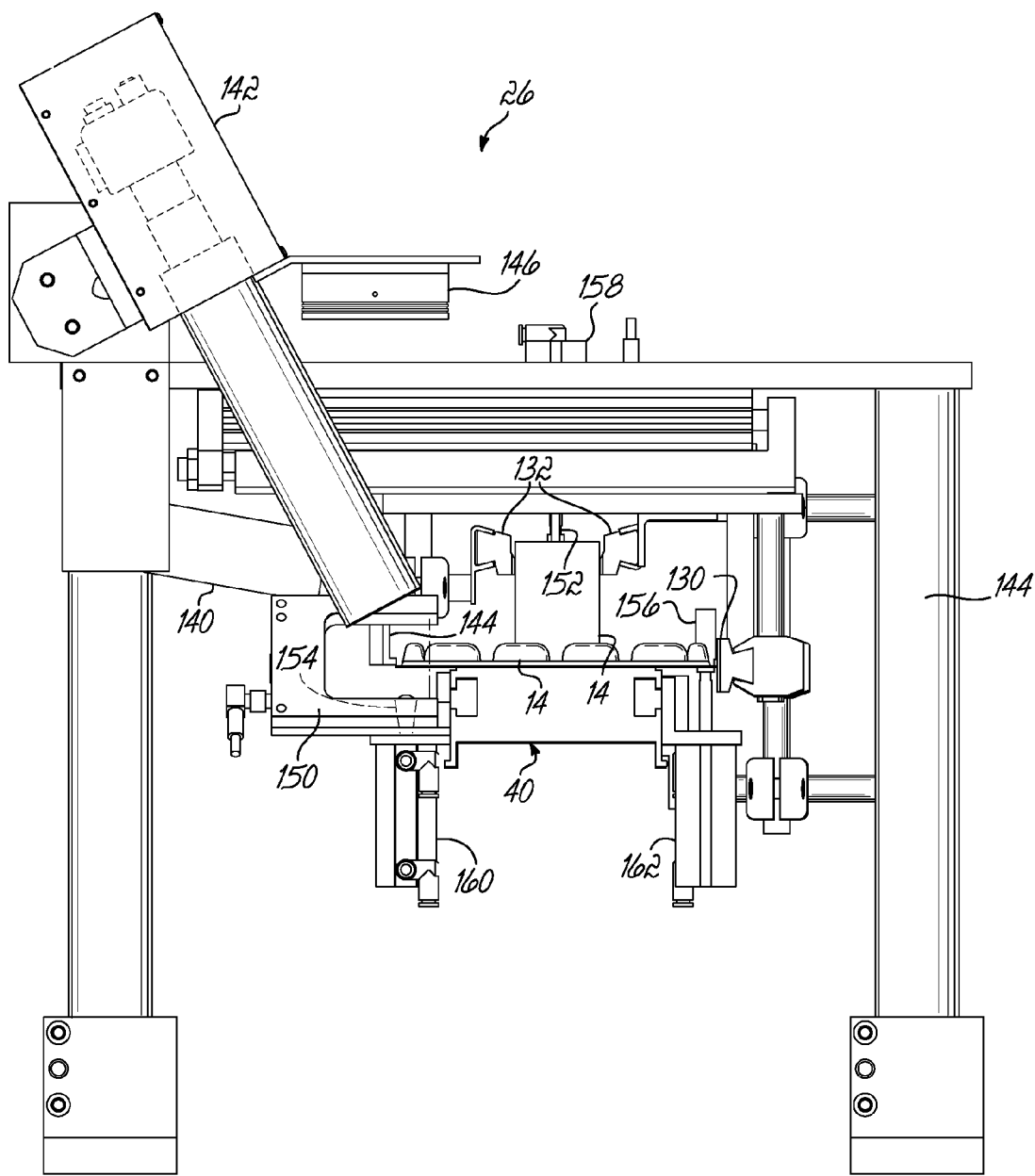
FIG. 15 is an end elevation view of the first product verification and rejection station of FIG. 14.

With reference to FIGS. 3, 14, and 15, the PVR1 station 26 is located downstream in the direction of product transport by the product conveyor 40 from the product induction magazines 22, 24 and generally upstream from the reject bin 44. The PVR1 station 26 includes a first barcode reader 140 electrically coupled with the controller 15, a second barcode reader 142 electrically coupled with the controller 15, and a side shift arm 144. Under the command of the controller 15, side shift arm 144 shifts or pushes rejected products 14 laterally from the product conveyor 40 to the reject bin 44. A lighting device 146, which is suspended from a support bracket over the product conveyor 40, is oriented to illuminate products 14 to supplement ambient lighting to promote the ability of at least the second barcode reader 142 to read the product barcode 28 on each product 14.

The first barcode reader 140 is configured to read the product barcode 28 on products 14 having the box form factor and to communicate electrical signals representing the read product barcode 28 to the controller 15. Accordingly, the first barcode reader 140 is aimed laterally relative to the product conveyor 40 with a field of view that can view the product barcode 28 on products 14 of the box form factor. The second barcode reader 142, which is suspended above the product conveyor 40, is configured to read the product barcode 28 on products 14 having the card form factor and to communicate electrical signals representing the read product barcode 28 to the controller 15. Accordingly, the second barcode reader 142 is aimed with a field of view that can view the product barcode 28 on products 14 of the card form factor.

The barcode readers 140, 142 may comprise either cameras or laser scanners. In the former embodiment, the controller 15 may implement machine vision software to analyze one or more images of the product barcode 28 communicated from one or both of the barcode readers 140, 142. In the latter embodiment, the controller 15 analyzes electrical signals encoding a string of characters contained in the product barcode 28 communicated from one or both of the barcode readers 140, 142. In the representative embodiment of the PVR1 station 26, barcode reader 140 is a laser scanner and barcode reader 142 is a machine vision camera. The controller 15 of the ALV machine 16 individually verifies the read product barcode 28 of the product 14 against the expected pick requests from the pharmacy host. This aids in ensuring that each of the products 14 loaded by the product induction magazines 22, 24 onto the product conveyor 40 matches any one of the expected products 14 in the tracking data for the pick batch introduced into the product induction magazines 22, 24.

The PVR1 station 26 includes a pair of sensors, of which sensor 150 is visible in the drawings, located relative to the product conveyor 40 for detecting the arrival of one of the products 14 at a location appropriate for triggering either the first barcode reader 140 or the second barcode reader 142 to read the product barcode 28 carried on the arriving product 14. The PVR1 station 26 also includes product stops 152, 154, 156 each mechanically coupled with a respective linear actuator 158, 160, 162, such as a pneumatic cylinder, having an output that moves each of the product stops 152, 154, 156 between extended and retracted positions relative to the product conveyor 40. In the extended position, the product stops 152, 154, 156 are positioned to contact the arriving product 14, which temporarily fixes the arriving product 14 in a stationary position. In the retracted position, the product stops 152, 154, 156 are withdrawn by the respective linear actuator 158, 160, 162 out of the path of the products 14 on the product conveyor 40.

In the representative embodiment, barcode reader 142 is a machine vision camera. Product stops 152, 154, 156 are used to temporarily halt the forward motion of each arriving product 14 of the card form factor at a location appropriate for using the side shift arm 144 to move rejected products 14 of the card form factor into the reject bin 44. If the controller 15 verifies the identity of the product 14, the product stops 152, 154, 156 are withdrawn to release the product 14 for transport on the product conveyor 40 to the LPVA station 29.

In the representative embodiment, barcode reader 140 is a laser scanner so that the product barcode 28 is read on the fly as the product 14 of the box form factor is transported by the product conveyor 40 through the field of view of the barcode reader 140. Product stop 152 is used to halt the forward motion of each arriving product 14 of the box form factor at a location appropriate for using the side shift arm 144 to move rejected products 14 of the box form factor into the reject bin 44. If the controller 15 verifies the identity of the product 14, the product stop 152 is withdrawn to release the product 14 for continued transport on the product conveyor 40 to the LPVA station 29.

The side shift arm 144 is coupled with a linear motion mechanism, which has the form of linear actuator (not shown) like a slide table as understood by a person having ordinary skill in the art. When appropriate electrical signals are communicated from the controller 15 to the linear actuator 160, the linear actuator 160 extends the side shift arm 144 by a distance sufficient to displace products 14 from the product conveyor 40 to the reject bin 44 and then retracts the side shift arm 144 out of the travel path of the products 14 on the product conveyor 40. The side shift arm 144 is located at a height relative to the product conveyor 40, and moves in a plane relative to the product conveyor 40, that promotes contact with the product 14 and ensuing movement of the contacted product 14 as the side shift arm 144 moves toward a fully extended position.

In use, products 14 entering the PVR1 station 26 break the detection plane of one of the presence sensors, which generates and sends an electrical signal to the controller 15. The controller 15 responds by communicating electrical signals containing instructions to read the associated product barcode 28 to an appropriate one of the barcode readers 140, 142. As a result, the controller 15 triggers either barcode reader 140 or barcode reader 142 based on the product tracking data for the appropriate form factor of the arriving product 14. The barcode readers 140, 142 attempt to read the product barcode 28 on the product 14. In the representative embodiment, barcode reader 140 reads the product barcode 28 as the product 14 of the box form factor is transported by the product conveyor 40 through the field of view of the barcode reader 140.

After the product barcode 28 is read, the controller 15 actuates the linear actuators 160, 162 to extend the product stops 154, 156 to catch the arriving product 14 of the card form factor that was released by product stop 154. For products 14 of the box form factor and after the product barcode 28 is read, the controller 15 actuates the linear actuator 158 to extend the product stop 152 to catch the arriving product 14 of the box form factor. The products 14 are held by product stops 152, 154, 156 while the controller 15 validates or qualifies the product barcode 28 for purposes of making a decision as to whether to reject the product 14 or to permit the product 14 to proceed onward in a downstream direction on the product conveyor 40 to the LPVA station 29.

If the product barcode 28 is not read within the specified time interval, then the product barcode 28 is considered to be missed or unreadable and a reject product flag is set. If the barcode readers 140, 142 fail to successfully read the product barcode 28 on three consecutive products 14, the ALV machine 16 halts with an alarm sounded and/or displayed at the HMI computer 72.

If the product barcode 28 is successfully read from the product 14 within a specified time interval, then the controller 15 records the product barcode 28. The controller 15 compares the product barcode 28 communicated from the barcode readers 140, 142 against the list of products 14 in the product magazine queue and loaded by the operator into one of the product induction magazines 22, 24 to determine which product 14 was scanned. If a match is found, the product 14 is considered to be loaded, and the pick batch data is then associated with the product 14. Only products 14 within the expected pick batch data are then released from the PVR1 station 26 to the downstream LPVA station 29. Each of the barcode readers 140, 142 in the PVR1 station 26 is set such that the product barcode 28 is not readable in the event that the product 14 is incorrectly loaded to the product induction magazines 22, 24.

The product 14 is considered a reject if the product barcode 28 was not read, or the product barcode 28 fails to match the anticipated product barcode 28 for one of the expected products 14. As described above, rejected products 14, while constrained in a stationary state relative to the moving product conveyor 40 by either product stop 152 or product stop 156, are side shifted by the side shift arm 144 from the product conveyor 40 into the reject bin 44. The controller 15 provides a control signal to the linear actuator 163 coupled with the side shift arm 144. The product 14 is considered a reject if the scanned barcode 28 fails to match any of the products 14 expected in the respective pick batch and is rejected by being removed from the product conveyor 40. Among the reasons for the mismatch may be that the product barcode 28 was not successfully read (e.g., no product barcode 28 was read, the product 14 was loaded with an incorrect orientation into the corresponding product induction magazine, etc.), the product barcode 28 is smudged, or the product barcode 28 was successfully read but fails to match any of the products 14 expected in the respective pick batch.

The controller 15 also confirms that products 14 identified as rejects are permanently removed from the product conveyor 40 at the PVR1 station 26. To that end, the side shift arm 144 extends and waits in the extended position for the product 14 to be detected entering the reject bin 44. If the rejected product 14 is not detected, the side shift arm 144 remains in the extended position and the ALV machine 16 stops with an alarm indicating that the rejected product 14 was not detected entering the reject bin 44. The side shift arm 144 retracts when the rejected product 14 is detected by sensors 170 or 172 (FIGS. 16, 17) as entering the reject bin 44.

Figure 16:
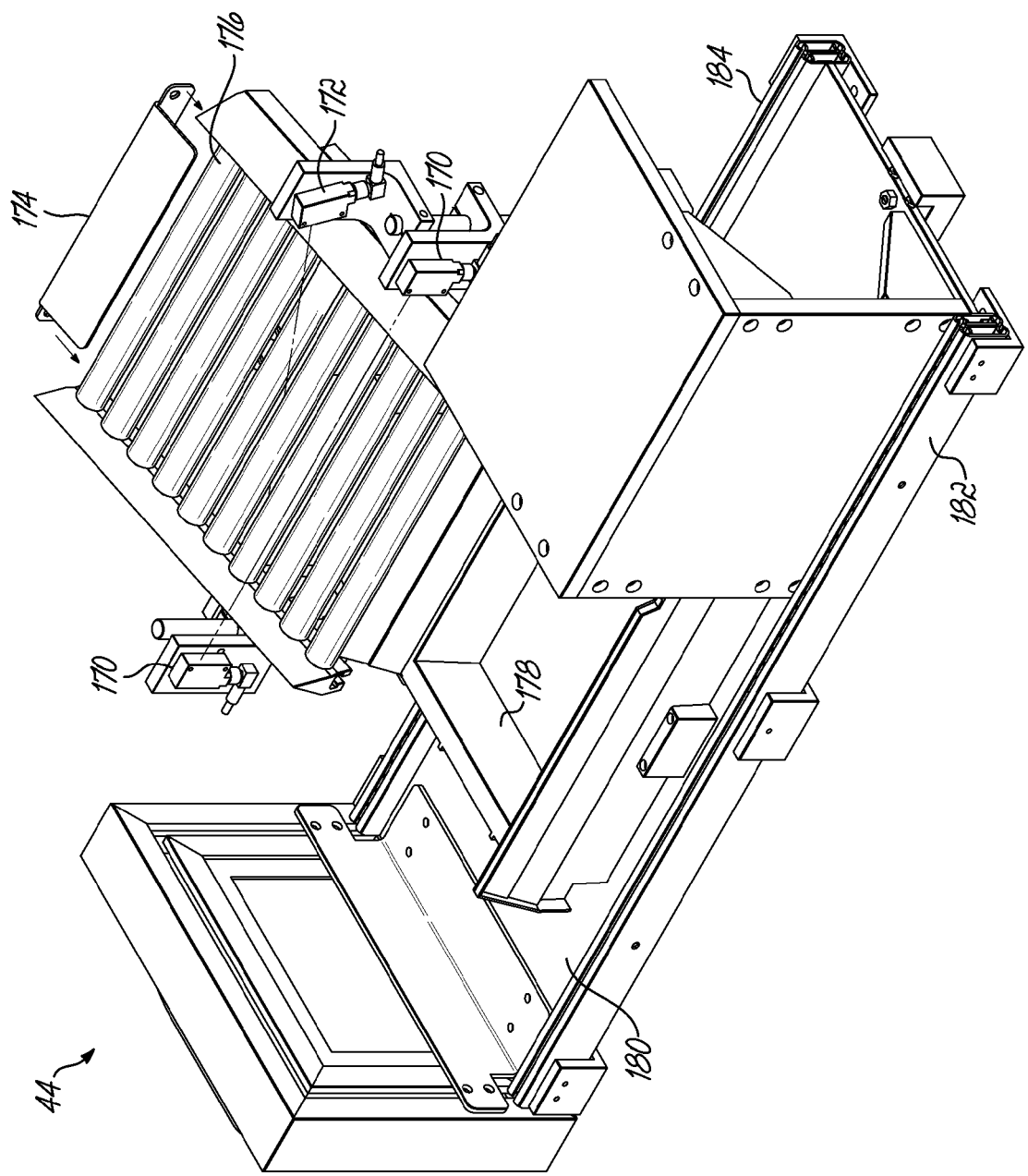
FIG. 16 is a perspective view of a reject bin of the ALV machine that receives products with a rejected product barcode.
Figure 17:
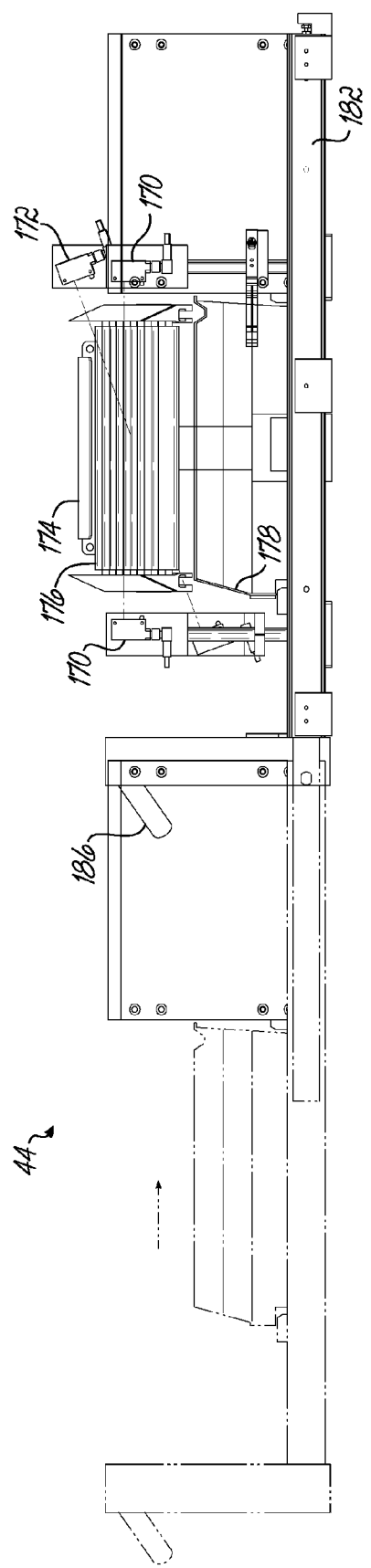
FIG. 17 is a side elevation view of the reject bin of FIG. 16.
Figure 18:
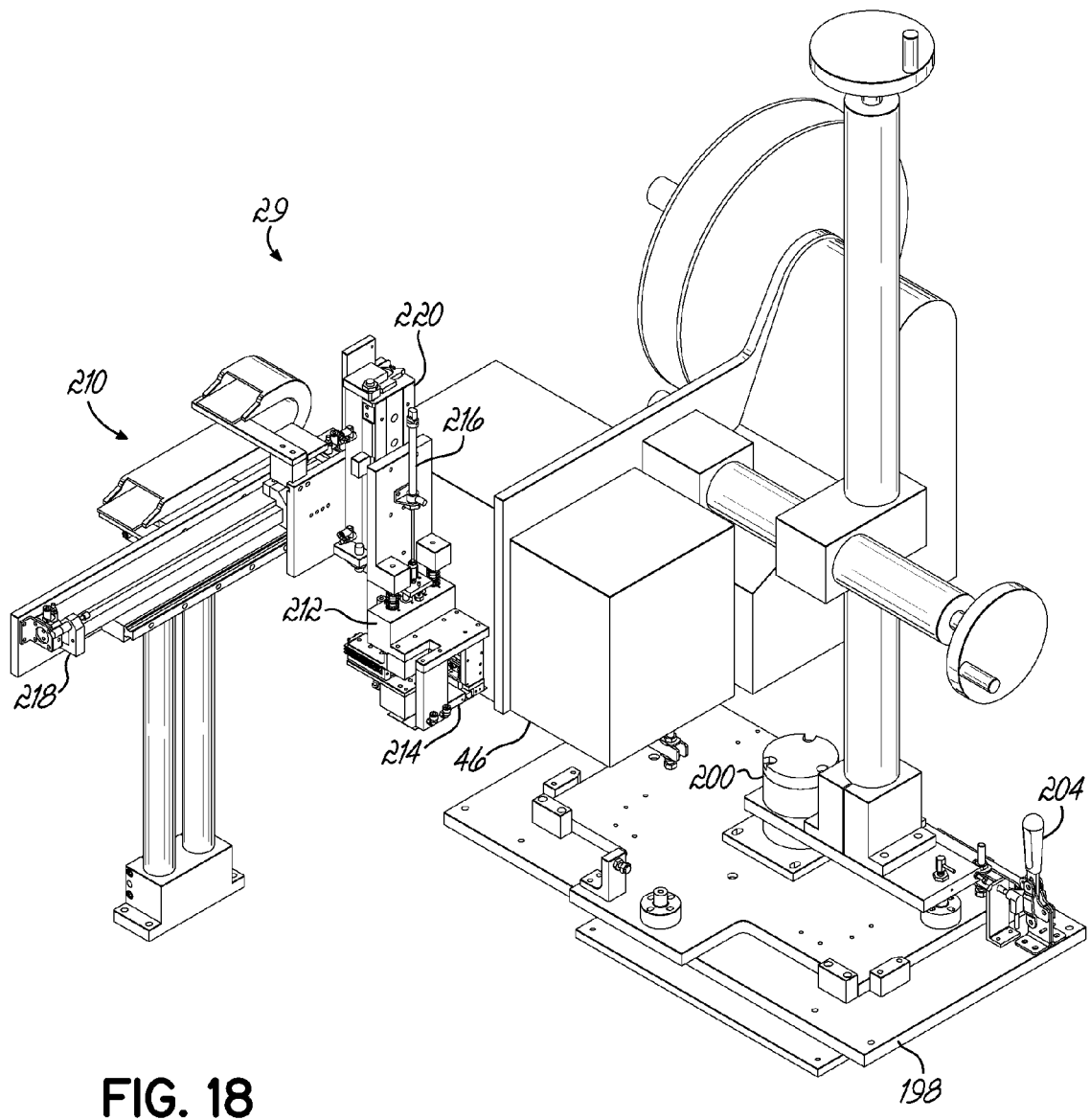
FIG. 18 is a perspective view of a label print, verify, and apply station of the ALV machine.
Figure 19:
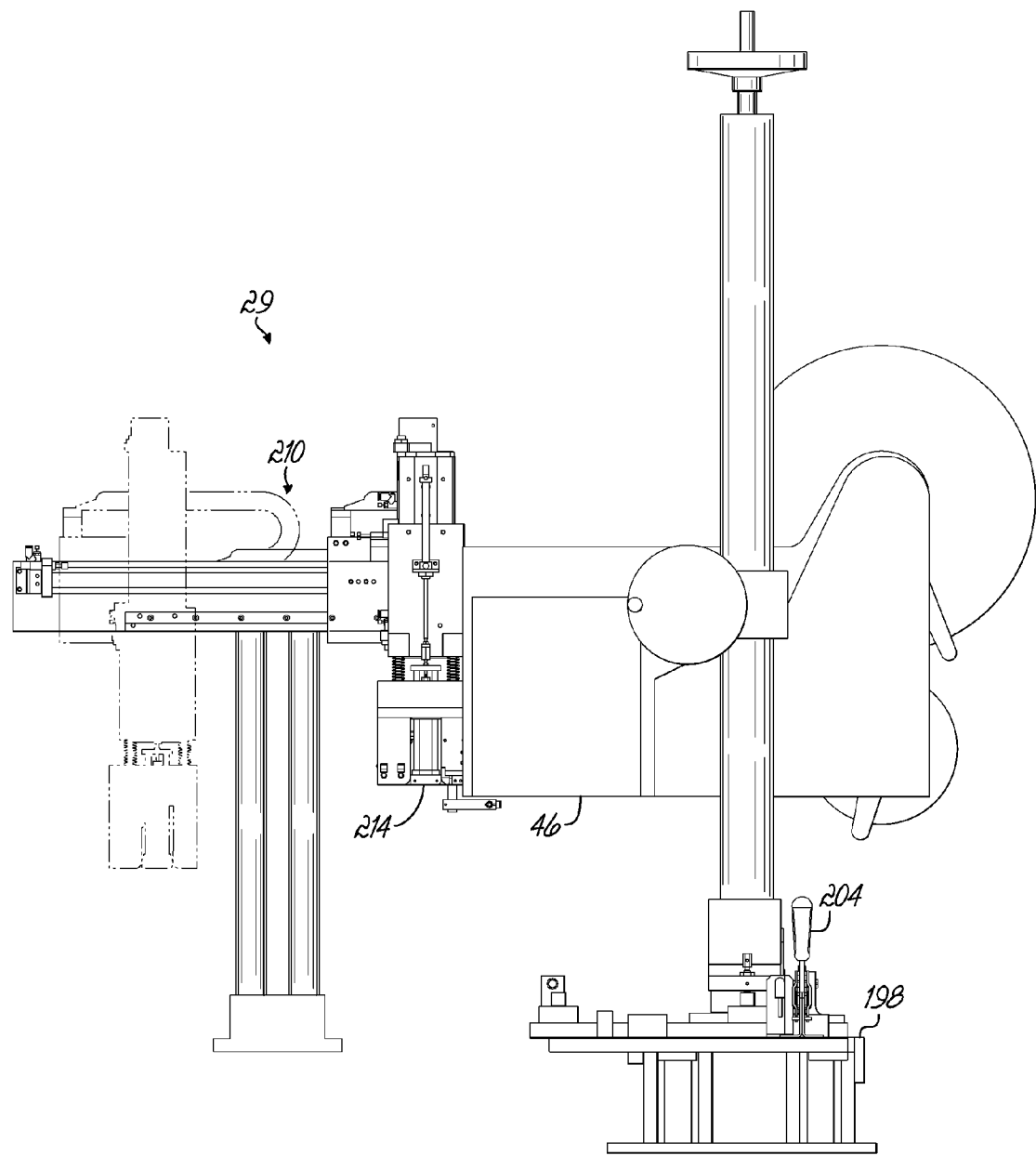
FIG. 19 is an end elevation view of the label print, verify, and apply station of FIG. 18.
Figure 20:
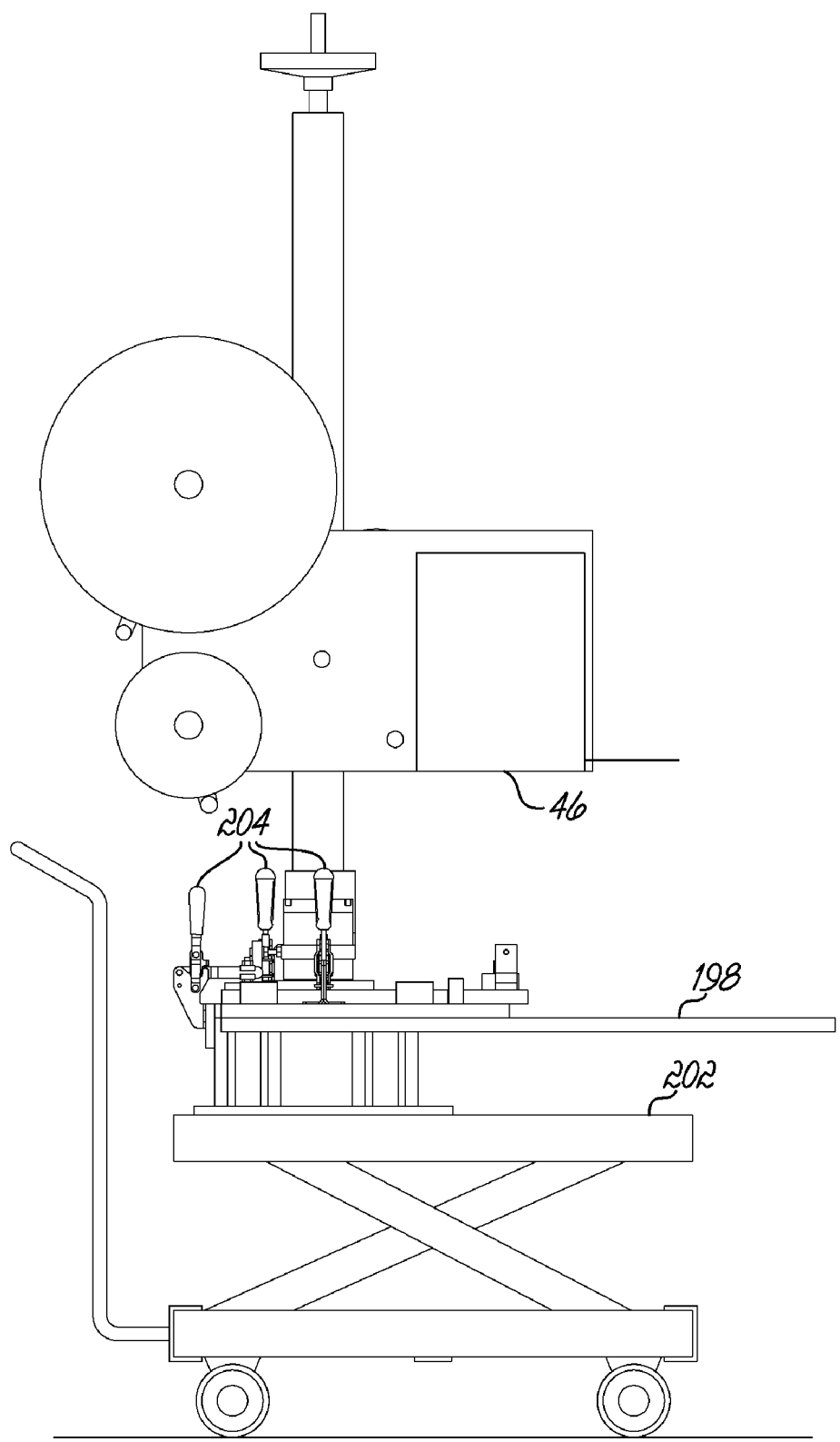
FIG. 20 is a side elevation view of a fixturing, label printer, and cart in the label print, verify, and apply station of FIGS. 18 and 19.
Figure 21:
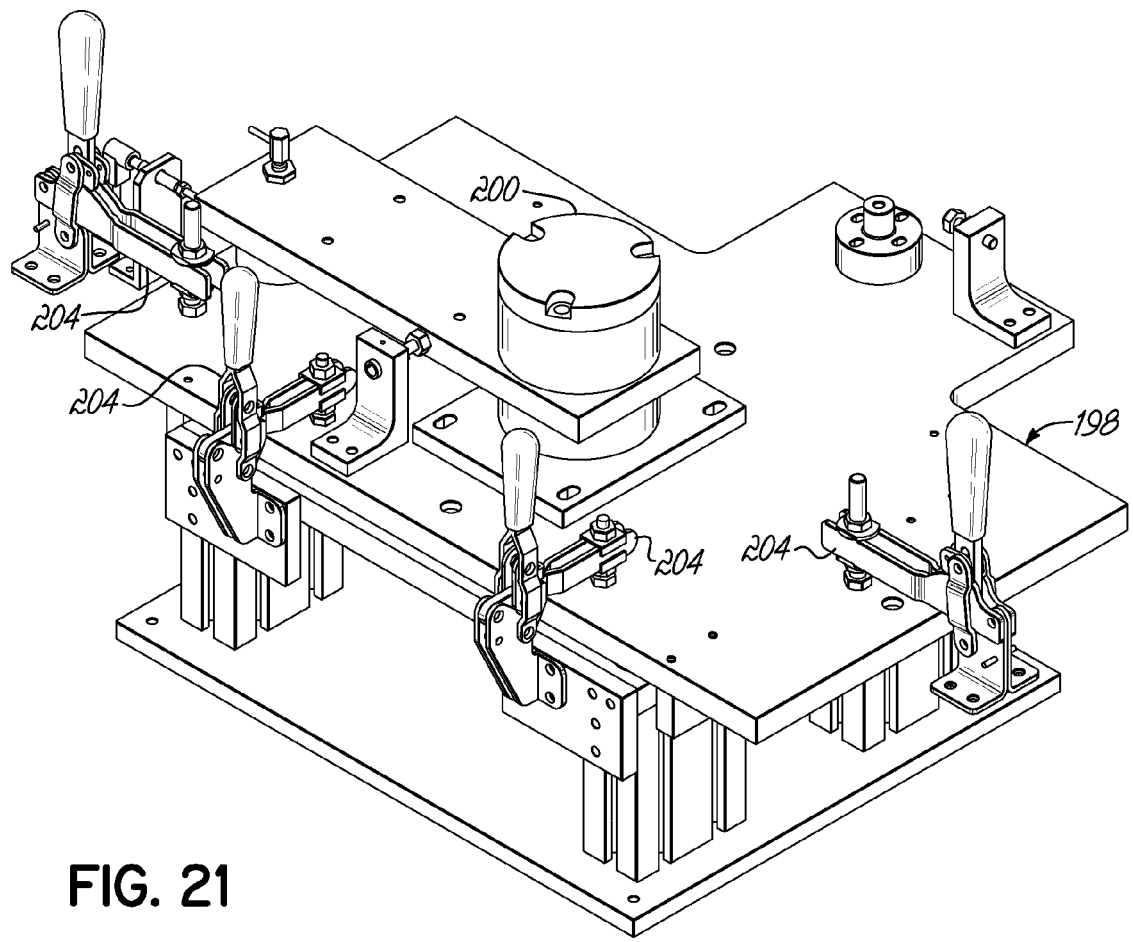
FIG. 21 is a perspective view of the fixturing of FIG. 20 that supports the label printer.
Figure 22:
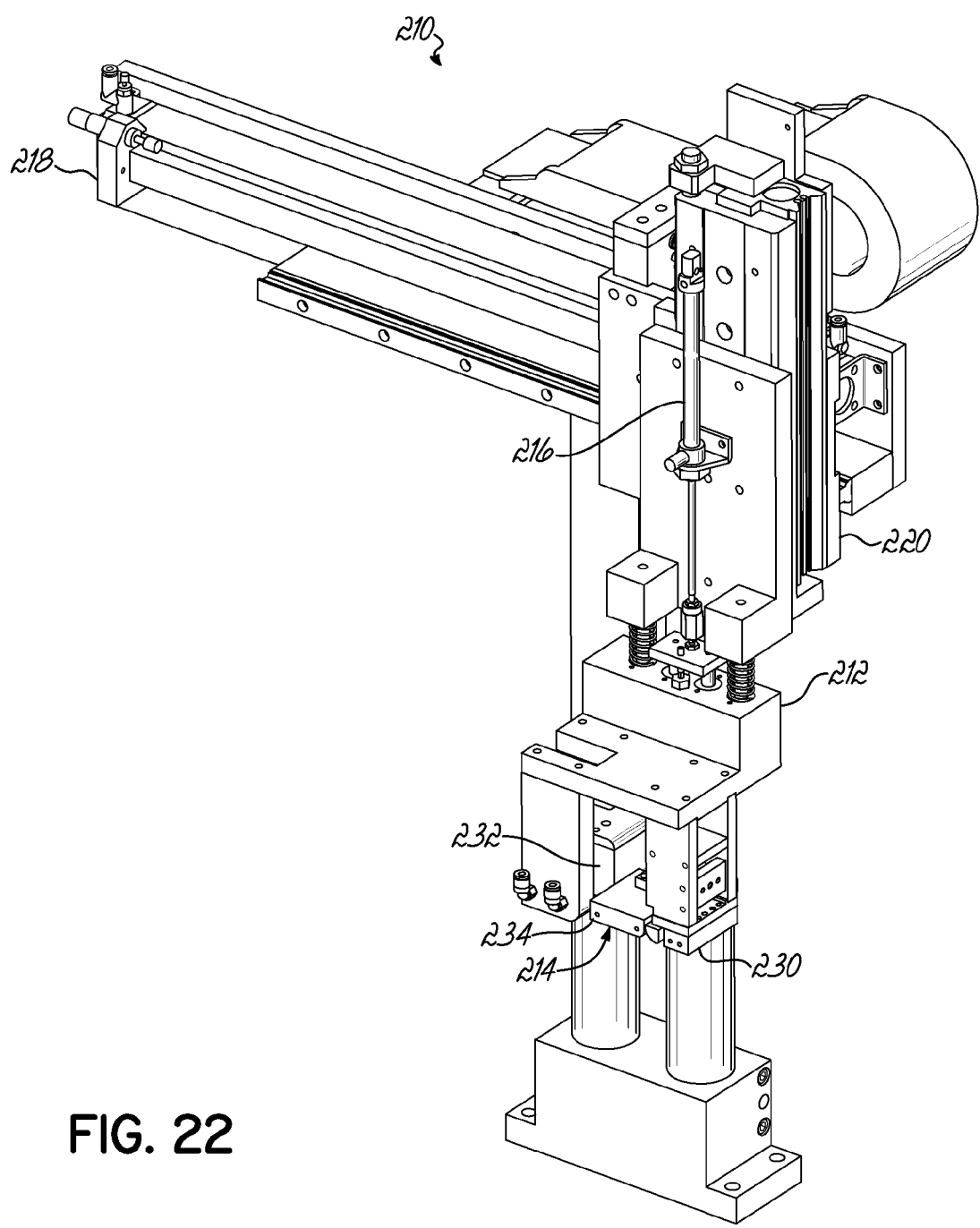
FIG. 22 is a perspective view of components of the label print, verify, and apply station of FIG. 18.

With reference to FIGS. 16 and 17, the reject bin 44 includes a support chute 174 that is coupled with the product conveyor 40, a roller conveyor 176 that is inclined downwardly away from the plane of the product conveyor 40 and the support chute 174, and a bin box 178 situated at the base of the roller conveyor 176. The support chute 174 bridges the gap between the roller conveyor 176 and product conveyor 40. The bin box 178 is carried on a drawer 180 that is mounted to rails 182, 184 for movement between an open position in which the products 14 in the bin box 178 are accessible for removal and a closed position in which the bin box 178 is positioned at the base of the roller conveyor 176. The drawer 180 includes a pull 186 for applying a force to manually move the drawer 180 between the open and closed positions. The reject bin 44 is located in the ALV machine 16 so that the operator can view any rejected products 14 residing in the bin box 178 when the drawer 180 is in the closed position. An operator can remove rejected products 14 from the bin box 178, when the drawer 180 is in the open position, without opening one of the guard doors 128 in the enclosure 126. Rejected products 14 removed from the bin box 178 of the reject bin 44 are available for reuse into the ALV system 10.

Rejected products 14 moving down the roller conveyor 176 move under the momentum imparted by the side shift arm 144 and the influence of gravity due to the elevation change. The reject bin 44 includes sensors 170 that detect the presence and passage of rejected products 14 with the box form factor and another sensor 172 that detects the presence and passage of rejected products 14 having the card form factor. The sensors 170, 172 are supported on respective brackets that serve to orient the sensor's output light beam relative to the plane of the roller conveyor 176. The controller 15 receives electrical signals from the sensors 170, 172 that are used by the controller 15 to confirm the arrival of products 14 in the bin box 178 of the reject bin 44. In one embodiment, the sensors 170, 172 are conventional through beam photoelectric sensors.

The reject bin 44, as well as the PVR1 station 26 and its side shift arm 144, are configured to handle products 14 having either of the form factors and without any reconfiguration or alteration to the machine 16. In particular, the same machine components are used to displace and collect rejected products 14 independent of form factor.

With reference to FIGS. 3 and 18-22, the LPVA station 29 is located downstream of the PVR1 station 26 in the direction of movement of products 14 along the product conveyor 40 and upstream from the PVR2 station 34. Products 14 bearing verified product barcodes 28 and released from the PVR1 station 26 are transported downstream by the product conveyor 40 to the LPVA station 29.

The LPVA station 29 includes the guide tooling 50 (FIGS. 25-27), which in turn includes a barcode reader 194 for reading the barcode 32 on patient labels 30 printed by the label printer 46 before application to the product 14. Product stop 134 (FIG. 11), upon receipt of instructions from the controller 15, stages each of the products 14 to be fed one at a time to the LPVA station 29. Barcode reader 194, which may comprise a machine vision camera electrically coupled with the controller 15, is oriented by a support bracket to have a field of view suitable for reading the barcode on each patient label 30 printed by the label printer 46 and before the patient label 30 is applied to the product 14. A lighting device 196, which is suspended from a support bracket over the product conveyor 40, is oriented to illuminate the patient labels 30 to supplement ambient lighting and thereby promote the ability of the barcode reader 194 to read the patient barcode 32 printed on the patient label 30.

The label printer 46 is disposed on a multi-level table 198 that includes stop mounts 200 for reproducibly exchanging the label printer 46 for a spare label printer (not shown). The label printer 46, which may comprise any commercial type of label printer 46, may include a large capacity label feed roll and a large capacity backing take-up roll. The label printer 46 and table 198 are disposed on a cart 202, which supports the weight of the label printer 46 and adds mobility to the label printer 46 without physical lifting. Releasable clamp mechanisms 204 fix the table 198 in position on the cart 202.

The label printer 46 features a 'Plug-and-Play' design so that, in the event of a printer failure or malfunction, the label printer 46 can be easily and quickly replaced with a spare label printer. The electrical connections for the label printer 46 with the ALV machine 16 feature releasable connectors (not shown) that promote the rapid replacement. If the label printer 46 fails or malfunctions, the operator first engages the cart 202, releases the clamp mechanisms 204, unplugs the electrical connectors, and wheels the failed label printer 46 away from the ALV machine 16 on the cart 202.

The label applicator 210 of the LPVA station 29 includes a head 212, a vacuum tamp pad 214 carried on the head 212, a linear actuator 216 that moves the vacuum tamp pad 214 relative to the head 212, and a pair of linear actuators 218, 220 that are operative to move the entire head 212. The vacuum tamp pad 214 temporarily captures each patient label 30 printed by the label printer 46 and the linear actuator 216 causes the vacuum tamp pad 214 to press the captured patient label 30 onto the product 14. Linear actuator 218 moves the head 212 laterally between a first position in which the patient label 30 can be pressed by cooperation between the vacuum tamp pad 214 and linear actuator 216 onto the product 14 and a second position in which the vacuum tamp pad 214 is displaced laterally to hover over the faulty label platen 48 (FIGS. 23, 24). Linear actuator 220 moves the head 212 of the label applicator 210 vertically for transferring faulty patient labels 30 from the vacuum tamp pad 214 to the faulty label platen 48.

In a representative embodiment, linear actuator 216 may consist of a pneumatic cylinder and a solenoid valve electrically coupled with the controller 15 for applying and venting air pressure to the pneumatic cylinder. Linear actuator 218 may consist of a rodless cylinder, and linear actuator 220 may have the construction of an air slide table with a motor electrically coupled with the controller 15.

The vacuum tamp pad 214 is configured to apply suction to the non-adhesive side of the patient label 30 while the vacuum tamp pad 214 manipulates the patient label 30 bearing the barcode 32 with the adhesive side facing downward toward the product 14. To that end, a vacuum line couples a suction source with vacuum inlets (not shown) on the vacuum tamp pad 214. A vacuum sensor, which is disposed in the vacuum line, is configured to detect whether or not the patient label 30 is fully captured and held on the vacuum tamp pad 214 such that the vacuum inlets are blocked.

The vacuum tamp pad 214 is configured to label products 14 having either the box form factor or the card form factor and, furthermore, is designed not to damage or crush products 14 with either box or card form factor. The flexibility of the construction of the vacuum tamp pad 214 to conform adaptively to the two different form factors for the products 14 is accomplished without any reconfiguration or alteration to the machine 16.

To that end, the vacuum tamp pad 214 includes peripheral sections 230, 232 and a central section 234 located between the peripheral sections 230, 232. The peripheral sections 230, 232 have a hinged, pivoting attachment with the central section 234 so that each of the peripheral sections 230, 232 can fold about a respective pivot axis toward the central section 234. When the patient label 30 is carried on the vacuum tamp pad 214, the fold lines 68, 70 of the patient label 30 generally coincide with the lines of pivoting action between the central section 234 and peripheral sections 230, 232.

When applying one of the patient labels 30 to one of the products 14 having the box form factor, the linear actuator 216 moves the vacuum tamp pad 214 toward the product 14 until contact is established between the portion of the patient label 30 carried on the central section 234 and the product 14. The central section 234 presses the adhesive side of the patient label 30 to adhesively bond the portion of the patient label 30 between the fold lines 68, 70 to the box. The peripheral sections 230, 232 of the vacuum tamp pad 214 wrap around the sides of the box 66 until the adhesive side of the patient label 30 contacts the box sides and is pressed against the box sides to generate an adhesive bond. The ability of the vacuum tamp pad 214 to adaptively wrap about the box sides minimizes the potential for ripping or damaging the label 30, creating wrinkles or creases in the patient label 30, and general damage to the box 66. This is performed in a relieved compliance nature.

Similarly, the linear actuator 216 moves the vacuum tamp pad 214 vertically to press the patient label 30 against products 14 of the card form factor with a force sufficient to establish an adhesive bond. In this instance, the peripheral sections 230, 232 do not have to pivot relative to the central section 234 to conform to a package form factor because the landing zone on the products 14 of the card form factor contacted by the central section 234 and peripheral section 230, 232 are substantially coplanar.

With specific reference to FIGS. 23 and 24, the faulty label platen 48 is housed inside a drawer 240, which is in turn supported on a pedestal adjacent to the LPVA station 29. The drawer 240 is mounted on guide rails 242 such that the drawer 240 can be moved between closed and open positions. In the closed position, the faulty label platen 48 is disposed spatially within the range of movement of the vacuum tamp pad 214, after it is moved laterally by the linear actuator 218, for receiving faulty patient labels 30. In the open position, the faulty label platen 48 is accessible for extracting faulty patient labels 30 for destruction and disposal. A sensor 244 is disposed with a detection beam overlying the faulty label platen 48, which may include a key lock 246 for controlling access to the faulty label platen 48.

With specific reference to FIGS. 3 and 25-27, the guide tooling 50 of the LPVA station 29 includes a pair of linear actuators 250, 252 that are located on opposite sides of the product conveyor 40, a pair of levers or fingers 254, 256 that are actuated by the output of a respective one of the linear actuators 250, 252 to grip products 14 of the card form factor, another pair of linear actuators 258, 260 that are located with a spaced apart relationship generally suspended above the product conveyor 40, and a pair of heads 262, 264 that are moved by the output of the respective one of the linear actuators 258, 260 to contact and grip products 14 of the box form factor. A pair of product stops 266, 268, each mechanically coupled with the output of a respective one of a pair of linear actuators 270, 272, are extended under the control of the controller 15 to stop the forward motion of products 14 of the card form factor so that the fingers 254, 256 can be actuated. In the representative embodiment, the linear actuators 250, 252, 258, 260, 270, 272 may comprise pneumatic cylinders each having a solenoid valve electrically coupled with the controller 15 for applying and venting air pressure.

Each of the linear actuators 250, 252 includes a rotatable shaft 278 coupled with a respective one of the fingers 254, 256 and a rack and pinion transmission 276 coupling an actuator output with the rotatable shaft 278 so that motion of the output of the linear actuators 250, 252 can drive the rotation of the rotatable shaft 278. Specifically, the rack and pinion transmission 276 converts the linear output of each of the linear actuators 250, 252 to a rotary motion of the respective rotatable shaft 278 with a rotation direction contingent upon whether the linear output is extending or retracting.

Linear actuator 258 is located upstream from the suspended location of the vacuum tamp pad 214 (FIGS. 18, 19) over the product conveyor 40. Linear actuator 260 is located downstream from the location of the vacuum tamp pad 214 so that the vacuum tamp pad 214 is located between the heads 262, 264. Each of the linear actuators 258, 260 includes a proximity sensor associated with the respective head 262, 264.

In use and with reference to FIGS. 11 and 18-27, the controller 15 instructs the linear actuator 136 to cause the product stop 134 to contact and capture the arriving product 14. When the preceding product 14 is released from the LPVA station 29, the controller 15 instructs the linear actuator 136 to withdraw the product stop 134, which releases the product 14 for continued transport on the product conveyor 40 toward the vacuum tamp pad 214. If the product 14 has the box form factor, the controller 15 instructs the linear actuators 258, 260 to extend the heads 262, 264 in a sequence appropriate to grip the box. If the product 14 has the card form factor, the controller 15 instructs the linear actuators 270, 272 to extend the product stops 266, 268 to stop the forward motion of the product 14 and the linear actuators 250, 252 to pivot the fingers 254, 256 to grip the card.

The controller 15 may communicate patient label information, format, and other commands for use in printing the patient label 30 while the product 14 is in transit to the product stops 152, 156. Under these circumstances, the throughput of the LPVA station 29 is not affected by the data transfer rate from the controller 15 to the label printer 46.

Patient labels 30 are printed by the label printer 46 and fed from a feed slot beneath a vacuum tamp pad 214, which applies suction to the non-adhesive side of the patient label 30 and is manipulated to move the patient label 30 toward the product 14 with the adhesive side facing downward toward the product 14. If vacuum sensor detects that the patient label 30, or any part of the patient label 30, is dropped by the vacuum tamp pad 214, the ALV machine 16 stops and triggers an alarm which prevents a patient label 30 from being accidentally applied to the product 14.

When the patient label 30 is securely held by suction on the vacuum tamp pad 214, the patient label 30 is scanned by the barcode reader 194. The electrical signals representing the read barcode 32 are communicated to the controller 15, which verifies the read barcode 32 against the tracking data. If the controller 15 determines that the read barcode 32 matches the information in the tracking data for positive verification, the product 14 is designated as ready for labeling and the controller 15 commands the vacuum tamp pad 214 to lower and press the patient label 30 onto the product 14. Products 14 of the box form factor with successfully read barcodes 32 that match the tracking data are aligned by the heads 262, 264 to ensure the position of the product 14 for the application of the patient label 30. Products 14 of the card form factor with successfully read barcodes 28 that match the tracking data are aligned by the fingers 254, 256 to ensure the position of the product 14 for the application of the patient label 30.

The controller 15 rejects the patient label 30 if the barcode reader 194 fails to read the barcode 32 within a reasonable time or if the controller 15 determines that the barcode 32 does not correlate with the value from the tracking data. The vacuum tamp pad 214 transfers rejected patient labels 30 to the faulty label platen 48, where the patient label 30 is removed from the vacuum tamp pad 214 by discontinuing the suction and optionally applying air pressure to the non-adhesive side of the patient label 30 to assist in releasing it. Rejected products 14 are released from the LPVA station 29 without being labeled with one of the patient labels 30, which permits optional restocking in the pick-to-light racks 12. The patient label 30 printed for a rejected product 14 is also rejected. This act will be repeated for a configurable number of attempts to attempt to label the product 14, at which time a major fault is triggered.

Rejected patient labels 30 are discarded by the ALV machine 16. To that end, the controller 15 commands linear actuator 216 to advance the vacuum tamp pad 214 away from the label printer 46 and then commands linear actuator to lower the vacuum tamp pad 214 to apply the rejected patient label 30 to the faulty label platen 48. The vacuum sensor in the line supplying suction to the vacuum tamp pad 214 is used to detect that the patient label 30 has been dropped and is no longer carried on the vacuum tamp pad 214. The ALV machine 16 stops with an alarm in the event that the patient label 30 is unexpectedly detected by the sensor on the vacuum tamp pad 214. If the patient label 30 is rejected, the corresponding unlabeled product 14 is released from the LPVA station 29.

When the controller 15 commands the product stop 134 to release one of the products 14 with the box form factor for application of the patient label 30, the controller 15 instructs the downstream linear actuator 258 to extend the head 262 into the travel path of the oncoming box. The front or leading end of the product 14 contacts the head 262, which halts the forward or downstream motion of the product 14. The controller 15 then instructs the upstream linear actuator 260 to extend head 264 to contact the rear or trailing end of the product 14. As a result, the product 14 is captured between the heads 262, 264. The barcode reader 194 reads the barcode on the patient label 30 and the vacuum tamp pad 214 applies the patient label 30 while the product 14 is secured and centered in this fixed position.

When the controller 15 commands the product stop 134 to release one of the products 14 with the card form factor for application of the patient label 30, the controller 15 instructs the linear actuators 250, 252 to operate so that the output causes each rack to rotate the pinion of the rack and pinion transmission and, as a consequence, the fingers 254, 256 to pivot toward the card. Contact between the fingers 254, 256 and the product 14 centers the product 14 and holds the product 14 stationary for application of the patient label 30. The vacuum tamp pad 214 applies the patient label 30 while the product 14 is secured and centered by the fingers 254, 256 in this fixed position.

After the patient label 30 has been successfully applied to one of the products 14, the suction to the vacuum tamp pad 214 is switched off to release the attractive force temporarily applied to the patient label 30 and the vacuum tamp pad 214 is raised by the linear actuator to a position to accept the successive patient label 30 printed by the label printer 46. After labeling, each product 14 carries one of the patient labels 30, which bears a validated product barcode 28 that can be used to electronically verify the contents of the product 14.

After label application, the controller 15 instructs the linear actuators 258, 260 to retract the heads 262, 264 if the product 14 has the box form factor. Alternatively, the controller 15 instructs the linear actuators 250, 252 to move the fingers 254, 256 and the linear actuators 270, 272 to withdraw the product stops 266, 268 in a manner that releases their grip on products 14 of the card form factor. The labeled products 14 are released for transport on the product conveyor 40 to the PVR2 station 34.

Figure 28:
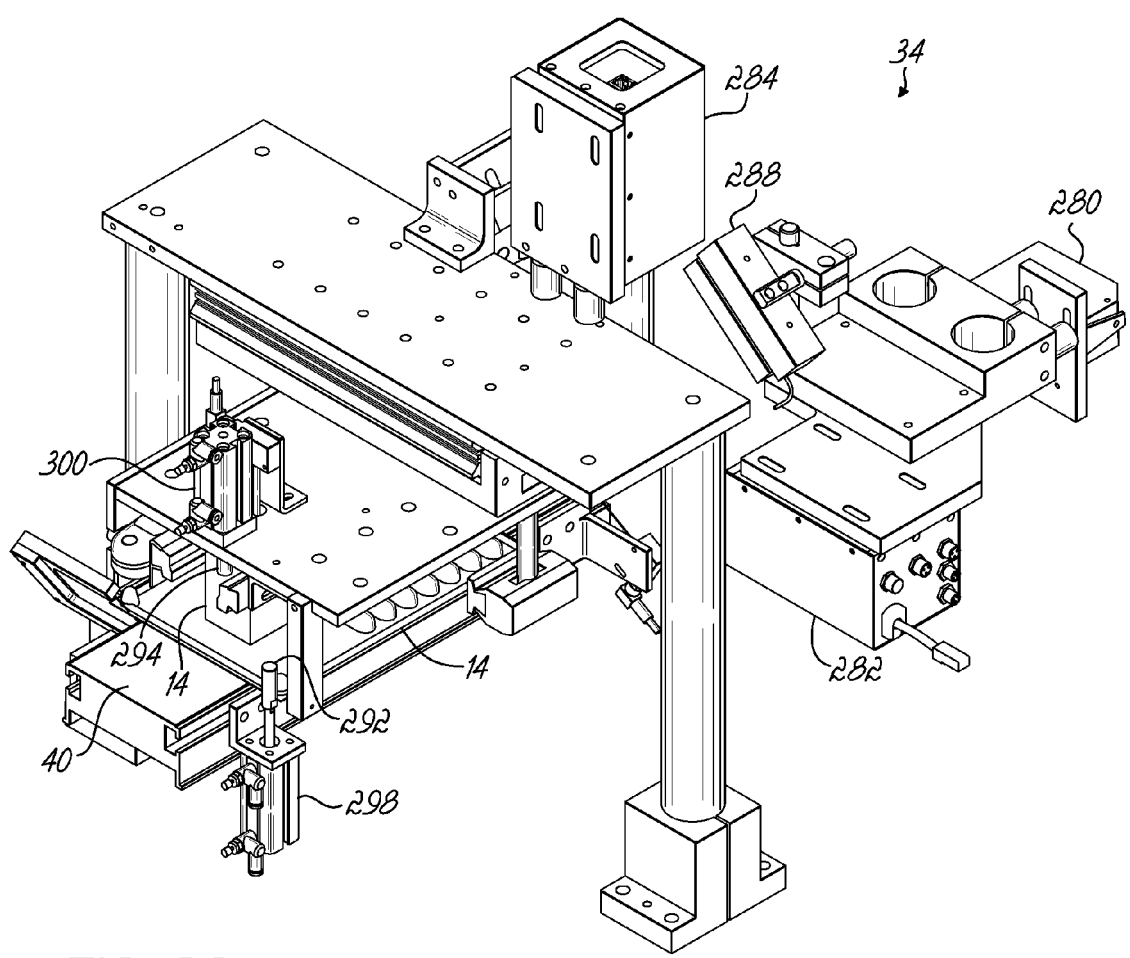
FIG. 28 is a perspective view of a second product verification and rejection station of the ALV machine.
Figure 29:
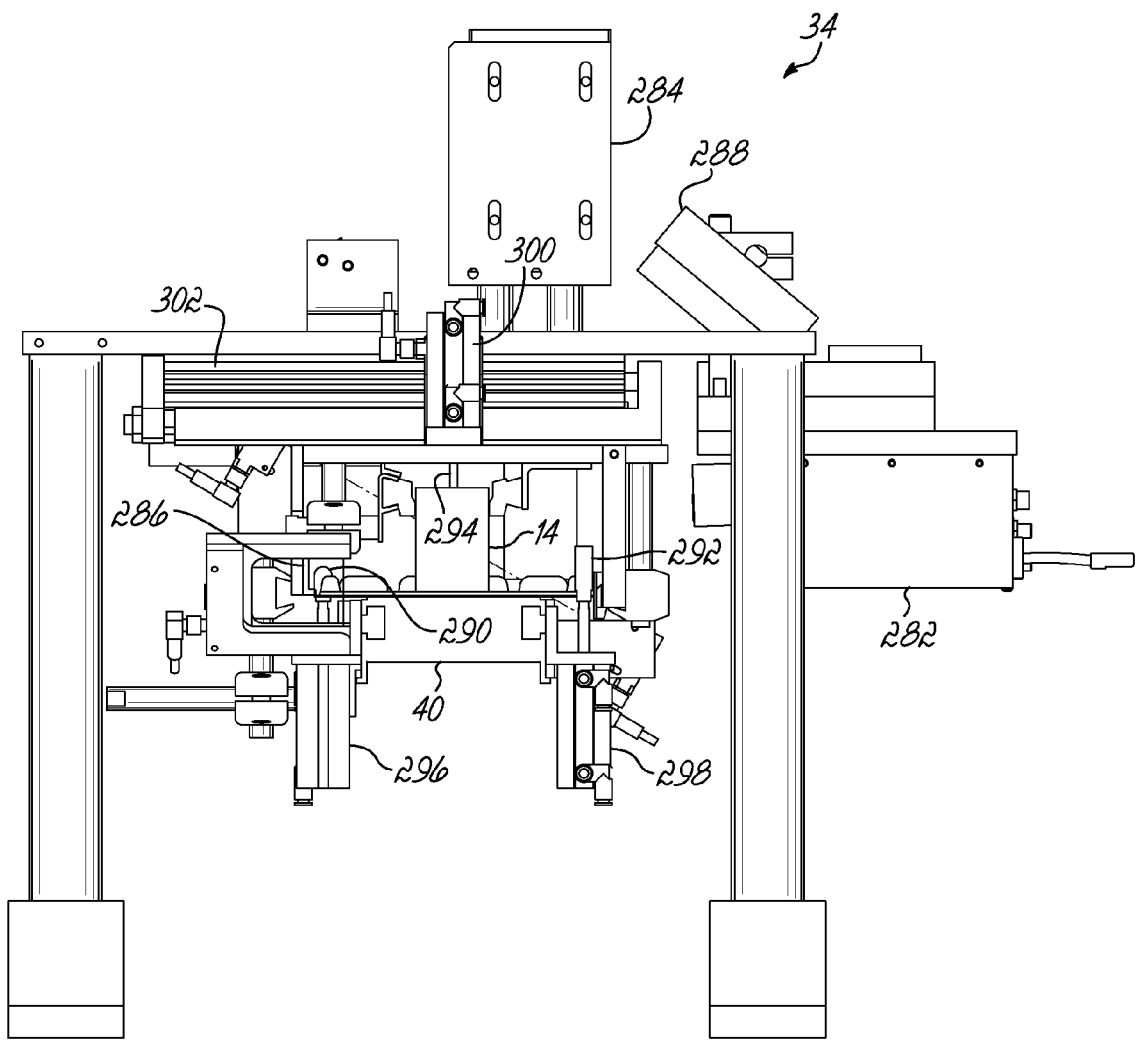
FIG. 29 is an end elevation view of the second product verification and rejection station of FIG. 28.
Figure 30:
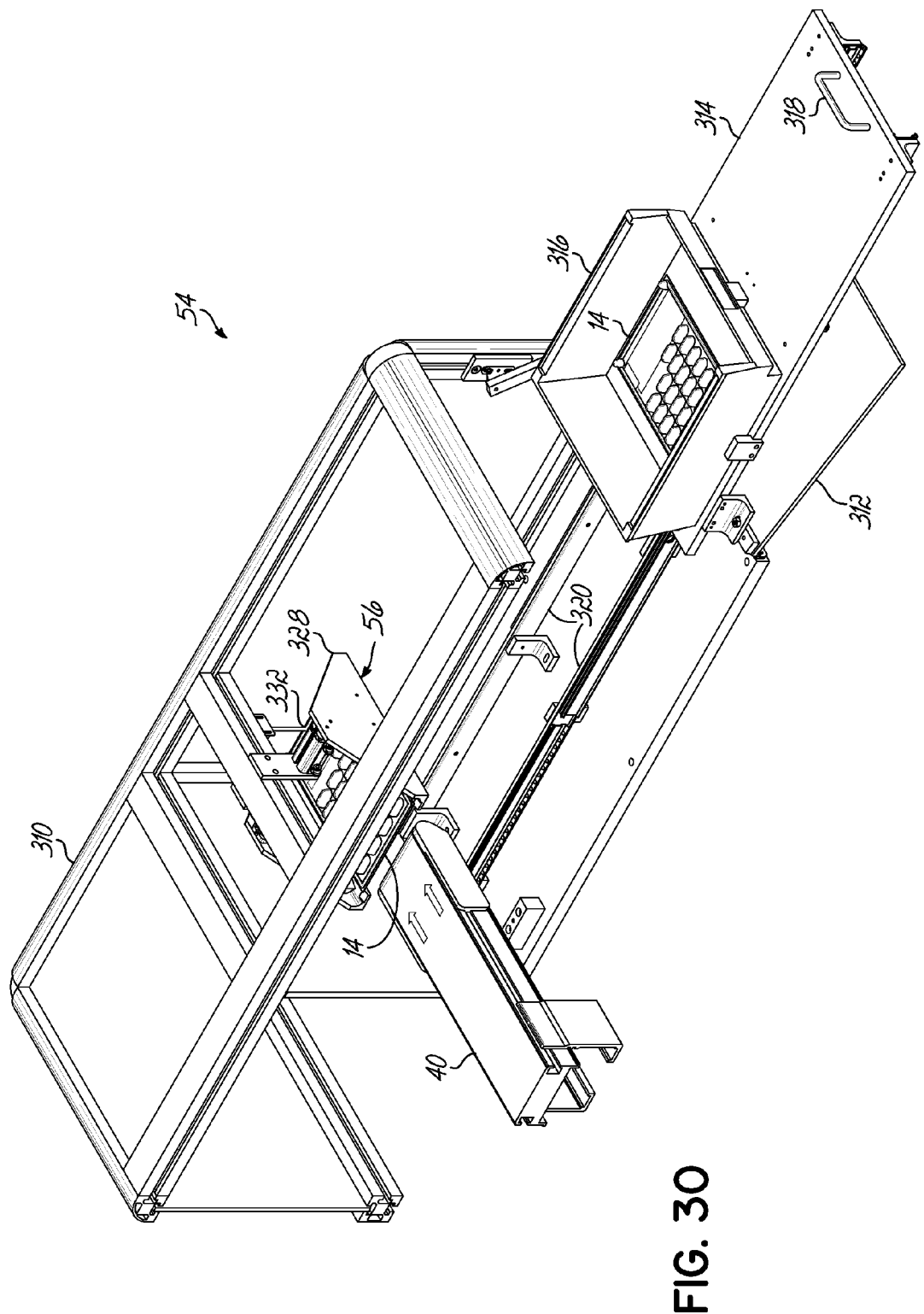
FIG. 30 is a perspective view of a reject bin associated with the second product verification and rejection station in the ALV machine that receives products carrying patient or product barcodes that fail to match with tracking data.
Figure 31:
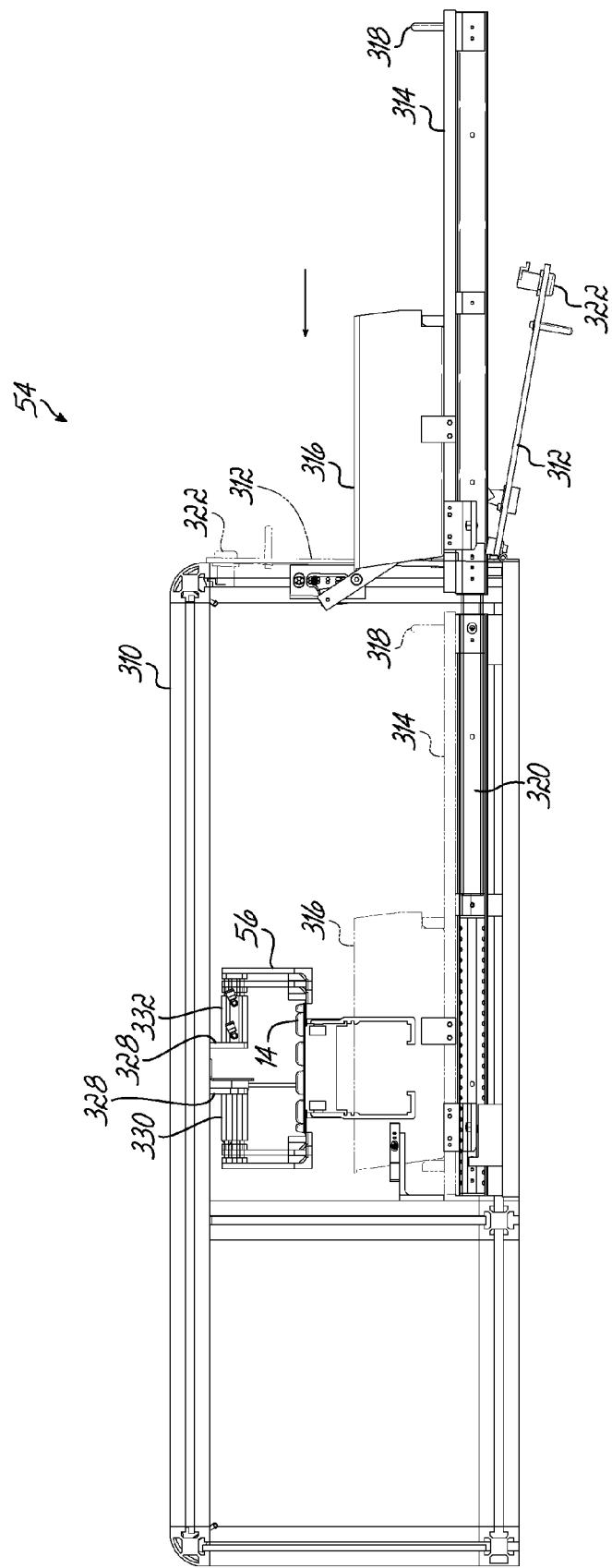
FIG. 31 is a side elevation view of the reject bin of FIG. 30.

With reference to FIGS. 3, 28, and 29, the PVR2 station 34 is located downstream of the LPVA station 29 in the direction of movement of products 14 along the product conveyor 40 and upstream from the reject bin 54 and escape 58. Products 14 with proper patient labels 30 are released from the LPVA station 29 and transported by the product conveyor 40 to the PVR2 station 34. The PVR2 station 34 is configured to handle products 14 having either the box form factor or the card form factor without any reconfiguration or alteration to the ALV machine 16.

The PVR2 station 34 includes a first barcode reader 280, a second barcode reader 282, a third barcode reader 284, and a side shift arm 286 that, under the control of the controller 15, shifts or pushes rejected products 14 laterally from the product conveyor 40 to the reject bin 44. The barcode readers 280, 282, 284 are electrically coupled with the controller 15. The first barcode reader 280 is oriented by a support bracket for reading the product barcode 28 on products 14 having the box form factor as the product 14 moves past the field of view of barcode reader 280 on product conveyor 40. The second barcode reader 282 is oriented by a support bracket for reading the patient barcode 32 on products 14 having the box form factor. The first and second barcode readers 280, 282 are aimed laterally relative to the product conveyor 40 with respective fields of view that can view the product barcode 28 and patient barcode 32 on products 14 of the box form factor.

The third barcode reader 284 is suspended above the product conveyor 40 by a support bracket for reading the product and patient barcodes 28, 32 on products 14 having the card form factor. The third barcode reader 284 is aimed with a field of view that can view the product and patient barcodes 28, 32 carried on products 14 of the card form factor. A lighting device 288, which is suspended by a support bracket in an overlying relationship with the product conveyor 40, is oriented to illuminate products 14 to supplement ambient lighting to promote the ability of the third barcode reader 284 to read the product and patient barcodes 28, 32 on the products 14.

The PVR2 station 34 includes a first product stop 290, a second product stop 292 spaced apart along the product conveyor 40 from the first product stop 290, a product stop 294 for regulating the forward movement of products 14 of the box form factor on product conveyor 40, and a sensor. The sensor is located and oriented relative to the product conveyor 40 for detecting the arrival of one of the products 14 at a location appropriate for triggering the first and second barcode readers 280, 282 to read the product and patient label barcodes 28, 32 on the arriving product 14 of the box form factor, or for triggering the third bar code reader 284 to read the product and patient label barcodes 28, 32 on the arriving product 14 of the card form factor. The product stops 290, 292, 294 are mechanically coupled with a respective one of linear actuators 296, 298, 300, which may comprise pneumatic cylinders, that actuates an output to move each of the product stops 290, 292, 294 between an extended position to contact products 14 moving on the product conveyor 40 and a retracted position physically out of the travel path of products 14 on the product conveyor 40. In the extended position, physical contact with a respective one of the product stops 290, 292, 294 holds the product 14 stationary relative to the underlying moving belt 106 of the product conveyor 40.

The barcode readers 280, 282, 284 may comprise cameras or laser scanners aimed with an appropriate field of view at the PVR2 station 34. In the former embodiment, the controller 15 may implement machine vision to analyze one or more images of the product barcode 28 communicated from the barcode readers 280, 282, 284. In the latter embodiment, the controller 15 analyzes electrical signals encoding a string of characters contained in the product barcode 28 communicated from the barcode readers 280, 282, 284.

In use, singulated products 14 arrive on the product conveyor 40 at the PVR2 station 34 from the LPVA station 29. For products 14 of the box form factor, barcode reader 280 reads the product barcode 28 as the package 14 moves on the conveyor 40 through its field of view. The controller 15 extends product stop 294 to halt the forward motion of each arriving product 14 of the box form factor at a location appropriate for imaging the patient barcode 32 using barcode reader 282. For products 14 of the card form factor, the controller 15 extends first product stop 290 to stop the forward motion of the package 14 so that barcode reader 284 can image the product and patient barcodes 28, 32. The controller 15 withdraws second product stop 292 to release the package 14 of the card form factor and extends product stop 294 to halt the forward motion of each arriving product 14 at a location appropriate for acquiring an image of the product and patient barcodes 28, 32 using barcode reader 284.

Electrical signals either from barcode readers 280, 282 or from barcode reader 284, dependent on form factor of the product 14, are communicated to the controller 15 and decoded into data representative of the barcode symbols. The controller 15 extends the second product stop 292 to contact the product 14 arriving on the product conveyor 40 after release by the first product stop 290, which again fixes the arriving product 14 in a stationary position. While the second product stop 292 temporarily halts the motion of the product 14, the controller 15 verifies the barcodes 28, 32 against the barcode information stored in the tracking data. In this fixed position and as instructed by the controller 15, the product 14 is staged either for release by retracting the second product stop 292, in which instance the product 14 continues to move on the product conveyor 40 toward the reject bin 54, or for lateral shifting by the side shift arm 286 from the product conveyor 40 to the escape 58.

If the controller 15 determines that the barcodes 28, 32 match with the tracking data, the controller 15 instructs a linear actuator 302 to move side shift arm 286 in a manner effective to displace the current product 14 from the product conveyor 40 to the escape 58 for subsequent transfer by the escape 58 to the container 20. Before initiating this action, the controller 15 verifies the successful completion of the previous operation of the side shift arm 286.

If the controller 15 determines that the barcode readers 280, 282, 284 could not read the barcodes 28, 32 or if the barcode values read by the barcode readers 280, 282, 284 fail to match the tracking data, the product 14 is rejected. Following release by retraction of the second product stop 292 or product stop 294, rejected products 14 are transported by the product conveyor 40 directly to the reject bin 54. The rejected products 14 drop, or are dropped in a controlled manner, off the end of the product conveyor 40 and into the reject bin 54. If the rejected product 14 is not detected by a sensor as entering the reject bin 54, the ALV machine 16 stops its operations and sounds an alarm.

If the controller 15 detects that either of the product stops 290, 292 at the PVR2 station 34 has failed, any products 14 inadvertently released from the LPVA station 29 are directed by normal operation of the product conveyor 40 to the reject bin 54 instead of the container 20.

With reference to FIGS. 30-33, the reject bin 54 for the PVR2 station 34 includes a protective housing 310 with an access door 312, a shelf 314, a bin box 316 residing on the shelf 314, a pull 318 on the shelf 314, and slidepacks 320, each consisting of nested pairs of extensible slides, disposed on opposite sides of the shelf 314. The shelf 314, which is mounted by brackets to the slidepacks 320 for movement relative to the protective housing 310, has a closed position in which the shelf 314 is housed inside the protective housing 310. When the shelf 314 is in the closed position, the bin box 316 is located on the shelf 314 to receive rejected products 14 dropped from the end of the product conveyor 40. In the closed position, the bin box 316 is positioned relative to the protective housing 310 so that the operator can see any rejected products 14 therein. The shelf 314 has an open position in which the shelf 314 is extended from the protective housing 310 such that the bin box 316 is accessible for removal of rejected products 14.

The access door 312 includes a physical lock 322 for control of human access to the rejected products 14 residing in the bin box 316. The access door 312 is not directly interlocked to machine control so that the ALV machine 16 continues to run normally when the access door 312 is opened to remove rejected products 14 and control is compromised. If the bin box 316 is not properly placed at the end of the product conveyor 40 for catching reject products 14 dropping from the end of the product conveyor 40, the controller 15 halts the operation of the ALV machine 16 coinciding with the arrival of a subsequent reject product 14.

The package drop 56 of reject bin 54 captures and drops rejected products 14 of the card form factor into the bin box 316, which promotes orderly stacking. The package drop 56 includes a pair of movable arms 326, 328 and a pair of linear motion mechanisms in the form of linear actuators 330, 332 that are electrically coupled with, and controlled by, the controller 15. The linear actuators 330, 332 are configured to move the respective arms 326, 328 inwardly and outwardly relative to each other between a first position having a relatively narrow separation that supports the card side edges and a second position characterized by a relatively wide separation such that a clearance exists between the card width and the arms 326, 328. Products 14 of the box form factor drop from the product conveyor 40 into the bin box 316 of the reject bin 54 between the arms 326, 328 and unhindered by the presence of the package drop 56. Products 14 of the box format factor fall into the bin box 316 with a trajectory governed at least in part by the forward momentum imparted by the velocity of the product conveyor 40. Sensors (not shown) are provided that detect the presence of rejected products 14 arriving on the product conveyor 40 and supported on the arms 326, 328.

In use, the controller 15 instructs the linear actuators 330, 332 to place the arms 326, 308 in the first position to catch arriving products 14 of the card form factor. Momentum imparted by the product conveyor 40 transports the arriving product 14 onto the arms 326, 328. After the controller 15 receives an indication from a sensor that the product 14 is supported on the arms 326, 328, the controller 15 commands the linear actuators 330, 332 to separate the arms 326, 328, which drops the product 14. The dropped product 14 falls substantially vertically into the bin box 316 independent of the momentum from the product conveyor 40 that otherwise would impart a trajectory to the motion of the rejected product 14 of the card format into the bin box 316. The orderly dropping reduces forces that, if not mitigated by the operation of the package drop 56, could cause the orientation of the products 14 of the card form factor to change during the drop so that the collected products 14 are not orderly stacked in the bin box 316.

Figure 33:
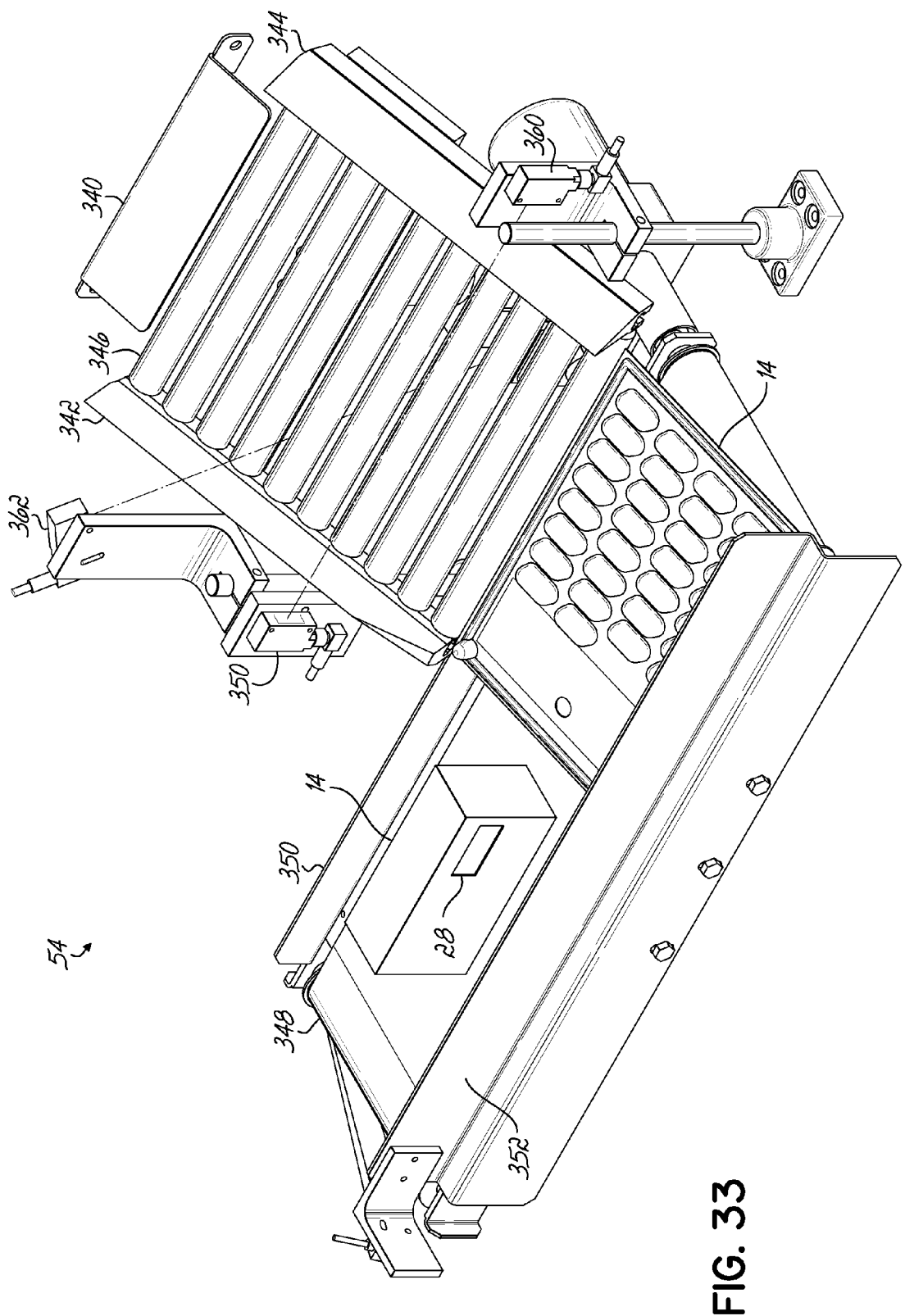
FIG. 33 is a top perspective view of an escape of the ALV machine for transferring verified and labeled products from the second product verification and rejection station to a container.

With reference to FIGS. 3 and 33, the escape 58 of the ALV machine 16 functions to transfer verified and labeled products 14 from the PVR2 station 34 to a stationary container 20 sitting on the conveyor 18. Specifically, the escape 58 directs products 14 displaced by the side shift arm 286 of the PVR2 station 34 from the product conveyor 40 to the container 20. The escape 58 includes a support chute 340 that is mounted to the side of the product conveyor 40, a pair of side guides 342, 344, a roller conveyor 346 between the side guides 342, 344, a motorized return conveyor 348 that receives products 14 from the roller conveyor 346, and another pair of side guides 350, 352 that flank opposite sides of the motorized return conveyor 348. The support chute 340 bridges the gap between the roller conveyor 346 and the product conveyor 40. The roller conveyor 346 is declined downwardly away from the plane of the product conveyor 40 toward the plane of the motorized return conveyor 348.

The escape 58 includes a sensor 360 that detects the presence and passage of products 14 with the box form factor and another sensor 362 that detects the presence and passage of products 14 having the card form factor. The sensors 360, 362 are supported on respective brackets that serve to orient the sensor's output light beam relative to the plane of the roller conveyor 346. The controller 15 receives electrical signals from the sensors 360, 362 that are used by the controller 15 to confirm the arrival of products 14 in the container 20. In one embodiment, the sensors 360, 362 are conventional throughbeam photoelectric sensors.

Figure 34:
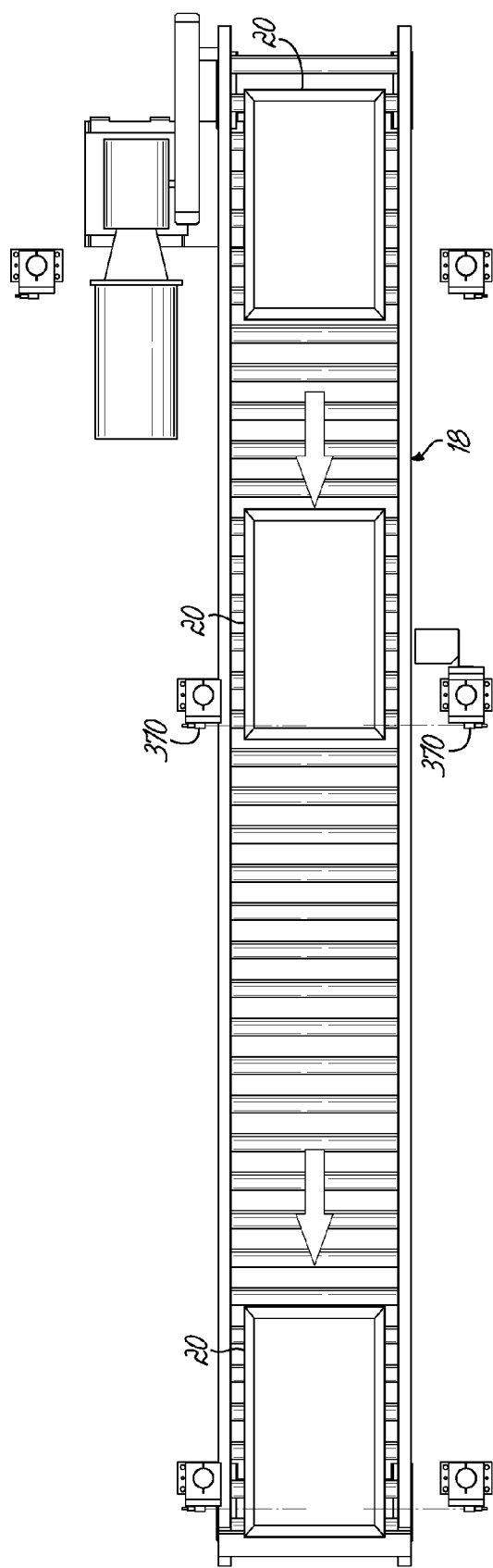
FIGS. 34 and 35 are top plan and side elevation views, respectively, of a roller conveyor for containers used to receive verified and labeled products processed by the ALV machine.
Figure 35:
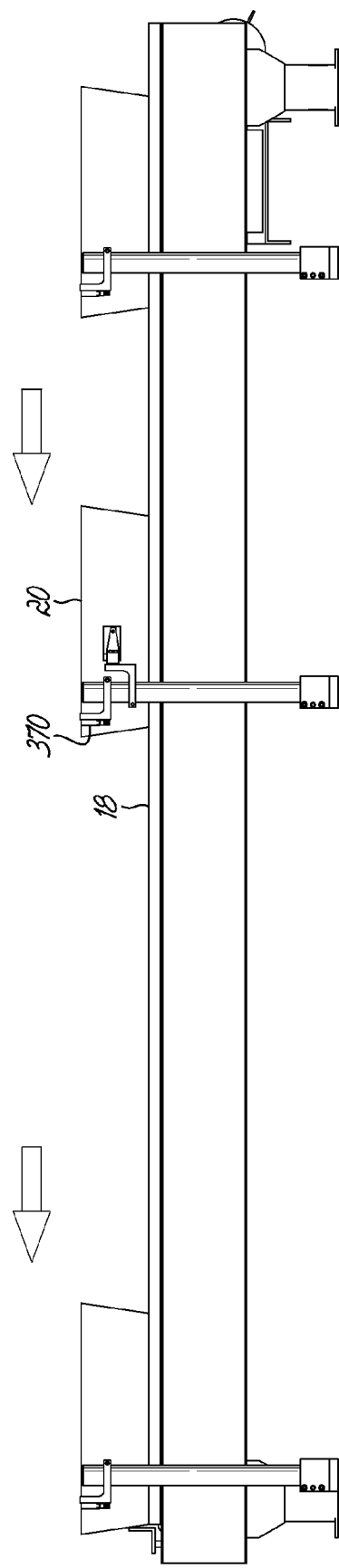

With reference to FIGS. 1, 34, and 35, the conveyor 18 that transfers containers 20 or sorting is located adjacent to an end of the ALV machine 16 opposite to the end having the product induction magazines 22, 24. The conveyor 18 includes one or more bar code readers (not shown) and one or more photoelectric sensors 370 that supply electrical signals to the controller 15 for use in controlling the movement of containers 20 on the conveyor 18. The conveyor 18 is instructed by the controller 15 to hold one of the containers 20 at a fixed position appropriate to receive labeled and verified products 14 from the motorized return conveyor 348 of the escape 58 and to transfer containers 20 away from the drop location of the motorized return conveyor 348 of the escape 58.

The products 14 of each container 20 may ultimately be transferred into a shipping tote (not shown) representing patient order destined for delivery to pharmacy customers. The containers 20 may remain inside the pharmacy and be reused by the ALV system 10.

The AOM, which is introduced above, executes various core functions of the ALV system 10. The AOM interfaces and communicates with the pharmacy host for orders and pick request. The AOM optimizes and prioritizes orders and picks into pick tickets and pick batches. The AOM monitors real time inventory and communicates the real time inventory to the pharmacy host. The AOM also manages and tracks the status of the various containers 20 matriculating through the ALV system 10. If the ALV system 10 includes multiple ALV machines like ALV machine 16, the AOM may also communicate with the various different ALV machines 16.

The pharmacy host computer supplies pick data to the AOM database for picks that can be dispensed by the ALV machine 16. Picks may be supplied from the pharmacy host computer to the AOM as a single record in a database table. The pick data includes the order number, drug SKU, order quantity, priority, destination, bulk label data, and other information used by the ALV machine 16 to print prescription labels as well as header information used to execute customized and configurable sortation and prioritization algorithms for each pharmacy where used.

The AOM communicates both verified and unprocessed orders/picks back to the pharmacy host. The AOM monitors pick status as they are completed and verified by the ALV machine 16. Once the products 14 are picked from the pick-to-light racks 12 system and verified by the ALV system 10, the updated pick data is communicated from the AOM back to the pharmacy host. Any products 14 shorted during the picking process, or rejected by the ALV system 10, forces the AOM to reissue the pick with a high priority status.

The AOM optimizes and prioritizes the picks into pick batches and pick tickets via sortation and prioritization algorithms. The AOM manages inventory within the ALV system 10. The AOM checks the inventory to find the products 14 required to complete the order. If the necessary products 14 cannot be found to complete the order, the AOM issues a replenishment request for the missing products. The order is placed on hold at the AOM until the replenishment for those inventory locations in the pick-to-light racks 12 have been made. Once the replenishment has been made for the needed inventory locations, the order is released to the ALV machine 16 upon request.

The AOM relies on one or more tote database tables, which reside on the AOM database, to modify the status of one of the containers 20. The AOM updates the tote status as products 14 are loaded to the container 20, and the container 20 is released to the pharmacy. The AOM inserts a record into an outgoing tote table every time the AOM modifies the tote status. Once the container 20 is emptied into a shipping tote, the pharmacy host inserts a record into the tote incoming table indicating that the container 20 is empty and available for loading new products 14.

Computer screens supply operator interface to the individual computers of the AOM. The computer screens may be used for system setup, pick mode selection, communication for the pharmacy host and ALV machine 16, and set-up of various parameters. Permission to make changes to these parameters via the computer screens may be restricted to authorized users.

The pick server executes the AOM software applications, communicates pick batch order information to the PickPC over a communications link, such as an Ethernet network over which information is transferred via TCP/IP socket communication. Pick information also resides in a customer supplied database resident on the AOM. The pick server manages a wide range of functions for the pick-to-light racks 12. The pick server monitors critical connections, sends and receives data from the pharmacy host, sends and receives data from the ALV machine 16, and provides web-based interfaces to system functionality for system configuration, order management, and statistics/productivity/reporting.

The pick-to-light racks 12 and ALV machine 16 are coupled by a communication link, such as a TCP\IP interface, that is configured to permit the exchange of real time transactions. The ALV machine 16 initiates the picking process by requesting new picks from the AOM, which in turn prompts the corresponding PickPC to light the necessary locations at the pick-to-light racks 12 for the new pick batch.

The pick server maintains the common log file used for transaction logging by the ALV system 10, including the ALV machine 16 and the controller 15. The pick server acts as a master time clock time server for all AOM computers, and ALV PCs and PLCs. Thus, all entries in the log files for the various ALV machine systems are synchronized.

The PickPC of the AOM parses orders in a pending server database, used internally by the pick-to-light racks 12. Order information is grouped and sorted based on the order prioritization and sortation rules. Authorized users are allowed to change the order priority of any pending order.

The real time PickPC of the AOM receives order data from the pick server and presents it to the individual pick-to-light modules in the pick-to-light racks 12 for lighting the indication lights on the different pick faces in conjunction with the content of the pick batch. The PickPC may use a Pick-to-Light interface controller with a TCP/IP interface to communicate with the bay controllers of the pick-to-light racks 12, which handle the direct communication with the pick modules.

The Pick PC of the AOM monitors and maintains the inventory levels of the ALV system 10, which includes all lot tracking and inventories at the pick face of the pick-to-light modules. The Pick PC of the AOM initiates pick face replenishment requests by adding the drug SKU to a replenishment list as the inventory levels reach replenishment trigger points. The replenishment list is then included in a replenishment report.

The StatPC of the AOM collects and displays statistics information about the operation of the pick-to-light racks 12. A statistics collection and display module of the StatPC monitors the picking process, collects system data, and displays the data in a variety of accessible formats. Other modules of the StatPC implement their functionality by using some subset of data collected by the statistics collection and display module. A SKU planning module of the StatPC uses statistics collected about the number of lines picked for each SKU over a period of time from the pick-to-light racks 12. The SKU planning module optimizes the drug SKU placement and suggests moves that would make the picking more efficient. The SKU planning module also allows for optimization with drug SKUs planned for insertion into the inventory locations in the pick-to-light racks 12. A workload status module uses statistics collected about the pickers, as well as information from the database and the Pick PC, to determine if a shift is going to complete the released orders or batches of orders on time.

The order reconciliation station of the AOM is used by the ALV system 10 as an order audit station with which an operator can verify the status of products contained in an arbitrary container 20 selected for audit. Work-in-process totes or containers 20 containing verified and labeled products 14 are directed to be routed to the audit station, as required by a quality control protocol. When one of the container 20 arrives at the audit station, the operator uses the handheld barcode scanner to scan the barcode on the container 20. In response, the audit station displays the expected contents of the container 20 and their respective statuses, which includes but is not limited to the pick status, lot numbers, product numbers, and order status.

The operator is instructed by the AOM to use the handheld barcode scanner to scan the barcode on the patient label 30 for each product actually residing in the container 20. As each successive patient label barcode is scanned, the display screen of the order reconciliation station may reflect the audited product 14 by, for example, changing the displayed color of each product 14 expected in the container 20. When all verified and labeled products 14 in the container 20 are accounted for, the audit is considered to be completed. This may be either that the patient label barcode was scanned, or that the product is marked as either missing or removed from the container 20. At the end of the audit, the status of each audited container 20 is recorded into an audit log, which is maintained in the AOM database and may be routinely backed up to a pharmacy database.

The AOM includes a user interface that allows the operator to view the status of the ALV systems and to control the pick-to-light racks 12. The user interface consists of a series of screens available on each of the various AOM systems (Pick Server, PickPC, StatPC, and Order Reconciliation Station) and Web based screens available to any computer connected to the associated Ethernet network. Access to the various screens, and options on each screen may be restricted based on the configuration profile for the pharmacy and the logged in user privileges.

The AOM interface may be used to change the priority of pick requests, to view the contents of pick requests including but not limited to label information, the product to be picked, the shipping tote, and the status of picks (e.g., queued, being picked, in process at an ALV, in tote), to view the status of the various ALV systems 10 if the pharmacy is equipped with more than one ALV system 10, to view the inventory levels at an ALV system, to perform diagnostics on the pick-to-light racks 12, to configure the pick-to-light racks 12, to generate and print reports on the performance of the ALV system 10, to view the global system log, to change the pick mode for the ALV system 10, to view the status and configure of the communications interfaces for the ALV system 10, to change the pick batch optimizations (Group by destination, Group by SKU, User defined optimizations), etc.

An ALV controller application, which may be written in a high level language such as Visual C++, is used to communicate between the ALV PLC, the AOM, and the label printer 46. The ALV controller application receives pick information from the AOM. The ALV controller application then strips off all non-specific patient label information, and forwards all processing information to the ALV PLC. The ALV controller application retains the patient label information for processing upon request. When the product 14 is inducted using the product induction magazines 22, 24 and detected by the ALV machine 16, the controller 15 processes the product 14 and initiates the request that the ALV controller application print the patient label 30 for the verified product 14.

The ALV controller application interface may provide the operator with an indication of the last message sent and received from the AOM, the last acknowledge message sent and received from the AOM, and the AOM communications status, as well the ability to view and modify AOM communications settings (e.g., the AOM IP address (or PC name) and the TCP/IP port number reserved for the ALV machine 16), to view and modify the ALV PLC Ethernet IP Communication settings (e.g., the ALV PLC IP address and PLC slot number), and to view and modify the ALV controller application debug log settings (e.g., the location of the current log file, the backup location for the log file, and the number of days of log files to maintain).

Generally, the barcodes 28, 32 on the products 14 and the patient label 30 incorporate symbols capable of being read by optical techniques, such as by readers implementing scanning laser beams or CCD cameras. The resulting electrical signals from the readers are decoded into data representative of the barcode symbols for further processing. The product barcode 28 and patient label barcode 32 may have the format of any one- or two-dimensional barcode recognized by a person having ordinary skill in the art, including but not limited to a Code 128 barcode. Common symbols used in barcodes include elements, such as solid dark, parallel bars of varying width, and spaces separating nearest neighbor elements. The elements represent strings of binary ones and spaces represent binary zeros. The specific arrangement of elements in the barcode defines the character represented by the barcode symbol in accordance with a code symbology corresponding to a set of rules and definitions specific to the code.

The barcode readers 140, 142, 194, 280, 282, 284 used to read the product barcodes 28 and patient barcodes 32 may comprise either a scanner incorporating a flying-spot laser beam or machine vision systems incorporating a charge-coupled device (CCD) camera or a CMOS-based imager, which have constructions and operations understood by a person having ordinary skill in the art. The choice of technology may depend upon various different factors including, but not limited to, depth of field and distance to the object.

In connection with a scanner, the flying-spot laser beam sweeps across each target barcode 28, 32 as the product 14 or patient label 30 move through the beam and the reflected and/or refracted light from the target barcode is detected. Because the elements of the barcode have lower reflectivity than the spaces between the bars, the amount of reflected/refracted light will vary contingent upon whether the projected spot of laser beam is incident upon an element or a space. The scanner communicates a stream of electrical signals representing the read barcode to the controller 15 for processing to decode the barcode.

In connection with a machine vision system, the camera captures a series of pixilated gray-scale or color optical images of the product as it passes through the camera's field of view at a given frame rate. The images are communicated as a stream of electrical or optical signals to the controller 15, which analyzes one or more of the frames using image analysis software. The camera may optionally incorporate an image processor that process the images to some extent before communicating the processed images to the controller 15. A trigger signal may be communicated from a sensor to trigger the occurrence of an event of interest within the field of view or the controller 15 may rely on visual event detection from the frames communicated from the camera.

The sensors used to detect the presence of products 14 at various locations within the ALV machine 16 may comprise photoelectric through-beam sensors having a structure understood by a person having ordinary skill in the art and, more specifically, dark operate type photoelectric through-beam sensors for positive part presence verification. The lighting devices used to illuminate the produces 14 may comprise any illuminator compatible with machine vision systems and having a structure understood by a person having ordinary skill in the art, such as incorporating light emitting diodes that emit light with a wavelength in the visible red band of the electromagnetic spectrum.

The ALV system 10 opportunistically relies on the two common form factors, namely cards in the representative form of flat blister cards 64 (FIG. 37) of solid dosages or boxes in the representative form of boxes 66 (FIG. 38) of solid dosages, to improve efficiency and to automate the labeling and verification process. The ALV system 10 processes and optimizes pharmacy verification or post adjudicated orders/pick requests, verifies that the correct patient label 30 is placed on the correct drug product 14, and verifies that the correct drug product 14 is placed into the correct container 20, without any damage either to the drug product 14 or to the patient label 30. The labeled and verified products 14 may include any combination of box or card formats. The ALV system 10 reduces medication errors associated with manual distribution, lowers costs associated with pharmaceutical distribution, permits reductions in personnel, and improves inventory control.

Figure 1A:
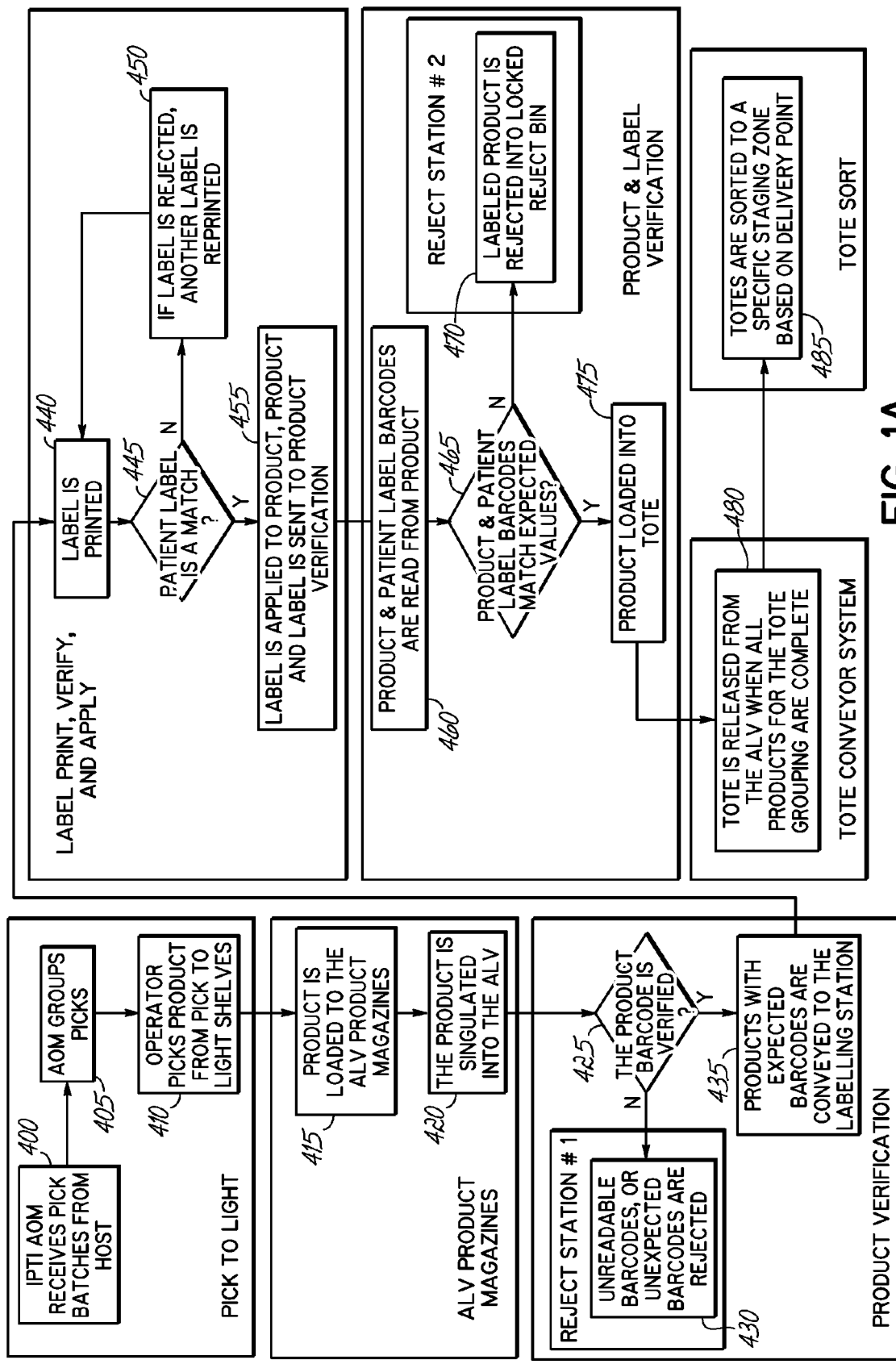
FIG. 1A is a flow chart illustrating the flow of products in the ALV system.
Figure 2:
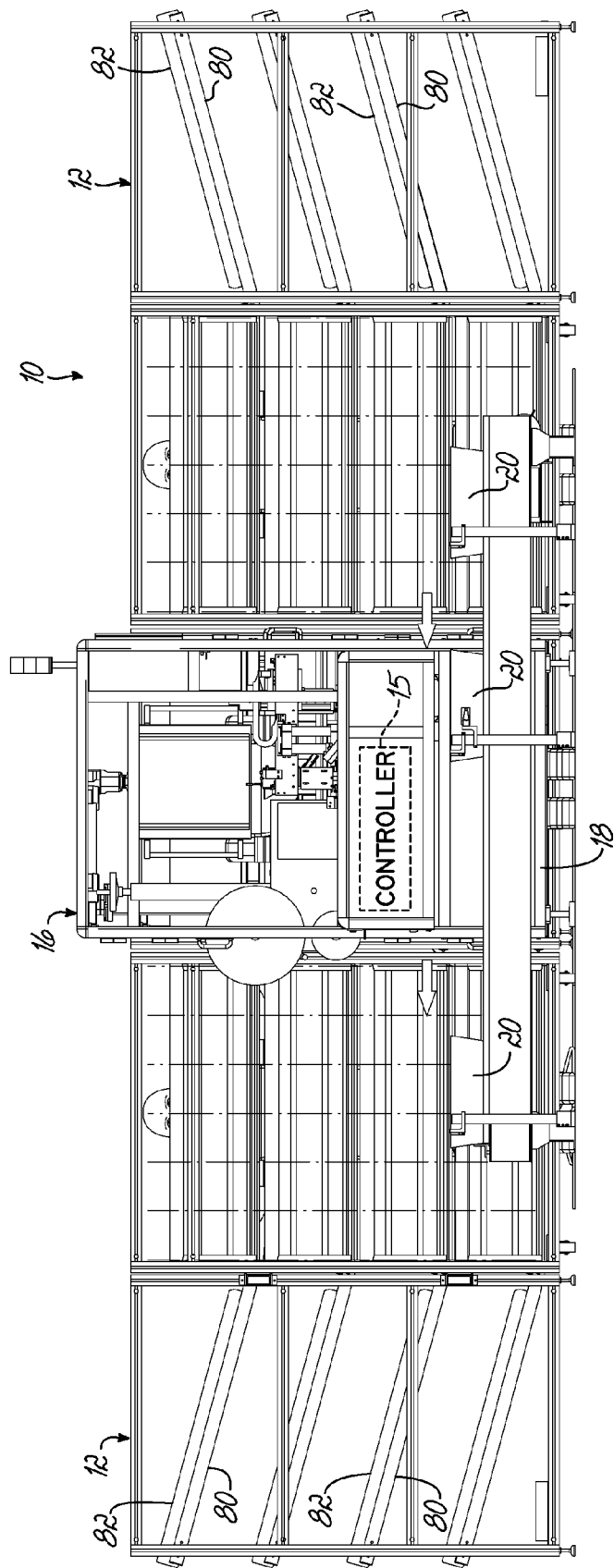

With reference to FIG. 1A and by way of general explanation of the overall operation of the ALV system 10, the AOM receives pick requests for products 14 from the pharmacy host in block 400. In block 405, the AOM groups the picks received in the pick requests communicated from the pharmacy host and, through the visual queues of the pick-to-light system 11, instructs the machine operator to pick products 14 from the shelves 80 in block 410. In block 415, the operator next loads the products 14 into the product magazines 22, 24 of the ALV machine 16. The selection of a specific one of the product magazines 22, 24 is in accordance with the form factor. In block 420, the products 14 are singulated onto the product conveyor 40 by the operation of the product magazines 22, 24.

In block 425, the product barcode 28 on each product 14 is read and verified at the PVR1 station 26. If the product barcode 28 fails to correlate with the expected product 14 (i.e., the barcode 28 is unexpected) or if the product barcode 28 is unreadable, then control is transferred from block 425 to block 430. In block 430, the product 14 is diverted to the reject bin 54 of the first reject station. If the product barcode 28 is readable and correlates with the expected product 14, then control is transferred from block 425 to block 435 in which the product 14 is permitted to be conveyed on the product conveyor 40 to the LPVA station 29.

At the LPVA station 29 of the ALV machine 16, the patient label 30 is printed using the label printer 46 in block 440. In block 445, the printed patient barcode 32 is compared with the value in the tracking data. If the patient barcode 32 printed on the patient label 30 is unreadable or fails to match the expected product 14, then the patient label 30 is rejected to the faulty label platen 48 and control is transferred from block 445 to block 450 in which the label printer 46 is instructed to print another patient label 30. The reprinted patient label 30 undergoes the verification process. If the patient barcode 32 printed on the patient label 30 is readable and matches the expected product 14, then control is transferred from block 445 to block 455 in which the patient label 30 is applied to the product 14 and the labeled product 14 is sent to the PVR2 station 34 for another verification step in block 455.

In block 460, the product barcode 28 and the patient barcode 32 are read from the product 14 at the PVR2 station 34. In block 465, the product and patient barcodes 28, 32 are compared with their the expected values. If the product and patient barcodes 28, 32 fail to match the expected values or if either barcode 28, 32 is not read, then control is transferred from block 465 to block 470. In block 470, the labeled product 14 is rejected into the locked reject bin 54 of the second reject station. If the product and patient barcodes 28, 32 match the expected value, then control is transferred from block 465 to block 475 in which the product 14 is loaded into a tote. In block 480, the tote is released from the ALV machine 16 when all products 14 for the tote grouping are complete. In block 485, the totes are sorted to a specific staging zone based on delivery point.

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art.

Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. An apparatus for filling a prescription order with a plurality of products each containing a pharmaceutical, each shaped with either a card form factor or a box form factor, and each marked with a product barcode, the apparatus comprising:
a conveyor configured to move the products along a workflow path;
a first verification station in the workflow path of the conveyor and configured to verify that the product barcode on each product belongs in the prescription order being filled;
a label application station in the workflow path of the conveyor and configured to print and apply a patient label onto each of the products; and
a second verification station in the workflow path of the conveyor and configured to independently verify that the product barcode on each of the products matches a patient barcode on the patient label after application to the product, the second verification station including a first barcode reader configured to read the product barcode and patient barcode on the products shaped with the card form factor, a second barcode reader configured to read the product barcode on the products shaped with the box form factor, and a third barcode reader configured to read the patient barcode on the products shaped with the box form factor.

2. The apparatus of claim 1 further comprising:
a first product feed device configured to receive and singulate batches of the products.

3. The apparatus of claim 2 wherein the first product feed device comprises:
a feed chute configured to receive a stack of the products;
a landing plate defining a bottom of the feed chute and configured to support the stack of the products; and
a gripping device movable relative to the landing plate, the gripping device configured to cooperate with the feed chute to successively singulate each of the products from the stack.

4. An apparatus for filling a prescription order with a plurality of products each containing a pharmaceutical, each shaped with either a card form factor or a box form factor, and each marked with a product barcode, the apparatus comprising:
a conveyor configured to move the products along a workflow path;
a first verification station in the workflow path of the conveyor and configured to verify that the product barcode belongs in the prescription order being filled;
a label application station in the workflow path of the conveyor and configured to print and apply a patient label onto each of the products;
a second verification station in the workflow path of the conveyor and configured to independently verify that the product barcode on each of the products matches a patient barcode on the patient label after application to the product,
a first product feed device configured to receive and singulate batches of the products with the card form factor; and
a second product feed device configured to receive and singulate batches of products shaped with the box form factor.

5. The apparatus of claim 1 further comprising:
a reject bin positioned adjacent the conveyor, the reject bin configured to receive the products determined by the first verification station to fail verification.

6. The apparatus of claim 1 wherein the second verification station includes a transfer arm configured to move laterally across the workflow path of the conveyor, and the apparatus further comprises:
an escape including a chute positioned adjacent to the conveyor, the transfer arm configured to push the products laterally from the conveyor onto the chute of the escape for transfer to a container.

7. The apparatus of claim 1 wherein the label application station is configured to independently verify the patient barcode on the patient label before the patient label is applied to one of the products.

8. The apparatus of claim 1 wherein the label application station comprises:
a label printer configured to print information on each of the patient labels;
an applicator configured to temporarily capture one of the patient labels from the label printer and move the patient label along a path of motion toward the product being processed by the label application station; and
a reject plate selectively movable between a first position in the path of motion of the applicator and a second position out of the path of motion,
wherein the applicator is configured to apply each of the patient labels to one of the products or to the reject plate.

9. The apparatus of claim 8 the applicator is configured to apply each of the patient labels to the products of the card form factor and the products of the box form factor.

10. The apparatus of claim 6 further comprising:
a tote handling system configured to handle the container.

11. The apparatus of claim 1 further comprising:
a controller operatively coupled with the conveyor, the first verification station, the label application station, and the second verification station, the controller configured to control the filling of the prescription order.

12. The apparatus of claim 1 wherein the workflow path of the conveyor is linear.

13. The apparatus of claim 2 wherein the first product feed device is configured to receive and singulate batches of products shaped with a card form factor, and the apparatus further comprising:
a second product feed device configured to receive and singulate batches of products shaped with a box form factor.

14. The apparatus of claim 13 wherein the second product feed device comprises:
a feed chute configured to receive a stack of the products;
a landing plate defining a bottom of the feed chute and configured to support the stack of the products; and
a gripping device movable relative to the landing plate, the gripping device configured to cooperate with the feed chute to successively singulate each of the products from the stack.

15. The apparatus of claim 5 wherein the first verification station includes a transfer arm configured to move laterally across the workflow path of the conveyor, and the transfer arm is configured to push the products laterally from the conveyor into the first reject bin.

16. The apparatus of claim 4 further comprising:
a reject bin positioned adjacent the conveyor, the reject bin configured to receive the products determined by the first verification station to fail verification.

17. The apparatus of claim 16 wherein the first verification station includes a transfer arm configured to move laterally across the workflow path of the conveyor, and the transfer arm is configured to push the products laterally from the conveyor into the reject bin.

18. The apparatus of claim 4 wherein the second verification station includes a transfer arm configured to move laterally across the workflow path of the conveyor, and the apparatus further comprises:
an escape including a chute positioned adjacent to the conveyor, the transfer arm configured to push the products laterally from the conveyor onto the chute of the escape for transfer to a container.

19. The apparatus of claim 18 further comprising:
a tote handling system configured to handle the container.

20. The apparatus of claim 4 wherein the label application station is configured to independently verify the patient barcode on the patient label before the patient label is applied to one of the products.

21. The apparatus of claim 4 wherein the label application station comprises:
a label printer configured to print information on each of the patient labels;
an applicator configured to temporarily capture one of the patient labels from the label printer and move the patient label along a path of motion toward the product being processed by the label application station; and
a reject plate selectively movable between a first position in the path of motion of the applicator and a second position out of the path of motion,
wherein the applicator is configured to apply each of the patient labels to one of the products or to the reject plate.

22. The apparatus of claim 21 wherein the applicator is configured to apply each of the patient labels to the products of the card form factor and the products of the box form factor.

23. The apparatus of claim 4 further comprising:
a controller operatively coupled with the conveyor, the first verification station, the label application station, and the second verification station, the controller configured to control the filling of the prescription order.

24. The apparatus of claim 4 wherein the first product feed device comprises:
a feed chute configured to receive a stack of the products;
a landing plate defining a bottom of the feed chute and configured to support the stack of the products; and
a gripping device movable relative to the landing plate, the gripping device configured to cooperate with the feed chute to successively singulate each of the products from the stack.

25. The apparatus of claim 4 wherein the second product feed device comprises:
a feed chute configured to receive a stack of the products;
a landing plate defining a bottom of the feed chute and configured to support the stack of the products; and
a gripping device movable relative to the landing plate, the gripping device configured to cooperate with the feed chute to successively singulate each of the products from the stack.

* * * * *

UNITED STATES PATENT AND TRADEMARK OFFICE
CERTIFICATE OF CORRECTION

| | | |
|---|---|---|
| PATENT NO. | : 8,262,842 B2 | Page 1 of 2 |
| APPLICATION NO. | : 12/234985 | |
| DATED | : September 11, 2012 | |
| INVENTOR(S) | : Michael J. Szesko et al. | |

It is certified that error appears in the above-identified patent and that said Letters Patent is hereby corrected as shown below:

Col. 4, last line, to Col. 5, line 1
"product barcode 28 the patient barcode 32" should be -- product barcode 28 or the patient barcode 32 --

Col. 5, line approx. 58
"representing or more" should be -- representing one or more --

Col. 7, line approx. 16
"barcode 32 is resides on one" should be -- barcode 32 resides on one --

Col. 7, line approx. 24-25
"labeled product 14 placed by" should be -- labeled product 14 is placed by --

Col. 8, line approx. 11-12
"setup and control" should be -- set up and control --

Col. 9, line approx. 3-4
"may have another configuration maybe chosen" should be -- may have another configuration chosen --

Col. 11, line approx. 27
"downstream toward to a" should be -- downstream to a --

Col. 13, line approx. 43
"rejection as to maintain" should be -- rejection so as to maintain --

Col. 20, line 1-3
"are extended under" should be -- is extended under --

Signed and Sealed this
Eighth Day of January, 2013

David J. Kappos
*Director of the United States Patent and Trademark Office*

CERTIFICATE OF CORRECTION (continued)
U.S. Pat. No. 8,262,842 B2

Col. 25, line approx. 42
"containers 20 or sorting" should be -- containers 20 for sorting --

Col. 25, line approx. 61-62
"for orders and pick request" should be -- for orders and pick requests --

Col. 26, line approx. 29-30
"replenishment for ... have been" should be -- replenishment for ... has been --

Col. 27, line approx. 56
"container 20 arrives" should be -- containers 20 arrives --

Col. 28, line approx. 32
"status and configure" should be -- status and configuration --

Col. 30, line approx. 50
"their the expected values" should be -- their expected values --

CLAIM 9, Col. 32, line 33
"claim 8 the applicator is" should be -- claim 8 wherein the applicator is --